(12) United States Patent
Cherkasov et al.

(10) Patent No.: US 9,035,035 B2
(45) Date of Patent: *May 19, 2015

(54) MACROMOLECULAR NUCLEOTIDE COMPOUNDS AND METHODS FOR USING THE SAME

(75) Inventors: Dmitry Cherkasov, Marburg (DE); Englbert Bäuml, Gross Grönau (DE)

(73) Assignee: GENOVOXX GMBH, Lubeck (DE)

( * ) Notice: Subject to any disclaimer, the term of this patent is extended or adjusted under 35 U.S.C. 154(b) by 673 days.

This patent is subject to a terminal disclaimer.

(21) Appl. No.: 11/886,518

(22) PCT Filed: Mar. 17, 2006

(86) PCT No.: PCT/EP2006/002461
§ 371 (c)(1),
(2), (4) Date: Mar. 16, 2009

(87) PCT Pub. No.: WO2006/097320
PCT Pub. Date: Sep. 21, 2006

(65) Prior Publication Data
US 2010/0093992 A1 Apr. 15, 2010

Related U.S. Application Data

(63) Continuation-in-part of application No. 10/578,313, filed as application No. PCT/EP2004/012556 on Nov. 5, 2004, now Pat. No. 8,637,650.

(30) Foreign Application Priority Data

Mar. 17, 2005 (DE) .......................... 10 2005 012 301

(51) Int. Cl.
| | | |
|---|---|---|
| C07H 21/04 | (2006.01) | |
| C07H 21/00 | (2006.01) | |
| C07H 19/06 | (2006.01) | |
| C07H 19/16 | (2006.01) | |
| C12Q 1/68 | (2006.01) | |

(52) U.S. Cl.
CPC .............. *C07H 21/00* (2013.01); *C07H 19/06* (2013.01); *C07H 19/16* (2013.01); *C12Q 1/6869* (2013.01)

(58) Field of Classification Search
CPC ........ C07H 19/06; C07H 19/16; C07H 21/00; C12Q 1/6869; C12Q 2537/143; C12Q 2525/179
See application file for complete search history.

(56) References Cited

U.S. PATENT DOCUMENTS

| | | | |
|---|---|---|---|
| 5,256,535 A | 10/1993 | Ylikoski et al. | |
| 7,220,847 B2 * | 5/2007 | Bodepudi et al. | ............ 536/23.1 |
| 7,456,266 B2 * | 11/2008 | Bodepudi et al. | .............. 536/4.1 |
| 2003/0054396 A1 | 3/2003 | Weiner | |
| 2003/0207300 A1 | 11/2003 | Matray et al. | |
| 2004/0248150 A1 | 12/2004 | Singh et al. | |
| 2007/0208169 A1 * | 9/2007 | Bodepudi et al. | ............ 536/26.1 |

FOREIGN PATENT DOCUMENTS

| | | |
|---|---|---|
| WO | WO 88/02784 | 4/1988 |
| WO | WO 03/020968 A3 | 3/2003 |
| WO | WO 03/048178 A2 | 6/2003 |
| WO | WO 2004/007773 A1 | 1/2004 |
| WO | WO 2004/092331 A2 | 10/2004 |
| WO | WO 2005-044836 A2 | 5/2005 |
| WO | WO 2006/097320 A2 | 9/2006 |

OTHER PUBLICATIONS

International Search Report issued in International Patent Application No. PCT/EP2006/002461 dated on Dec. 29, 2006.
International Search Report issued in International Patent Application No. PCT/EP2007/008198, dated Apr. 17, 2009.
International Search Report, with its partial English translation, issued in International Patent Application No. PCT/EP2004/012556, dated May 19, 2005.
Lemaitre M et al., "Biological Activities of Oligonucleotides linked to Poly(L-Lysine)", Nucleosides, Nucleotides and Nucleic Acids, 1987, pp. 311-315, vol. 6 No. 1&2, Marcel Dekker, Inc, New York.
Jaeschke, A et al., "Hybridization-based affinity partitioning of nucleic acids using PEG-coupled oligonucleotides", Nucleic Acids Research, 1994, vol. 22 No. 10, pp. 1880-1884, Oxford University Press.
United States Office Action issued in U.S. Appl. No. 10/578,313, mailed Mar. 16, 2011.
U.S. Office Action issued in U.S. Appl. No. 10/578,313, dated Dec. 8, 2011.
Untied States Patent and Trademark Office Action for U.S. Appl. No. 10/578,313 dated Mar. 7, 2013.

* cited by examiner

*Primary Examiner* — Lawrence E Crane
(74) *Attorney, Agent, or Firm* — McDermott Will & Emery LLP

(57) ABSTRACT

The invention describes new structures of the nucleotide conjugates (nuc-macromolecules) comprising at lease one nucleotide moiety coupled to at least one macromolecular compound via a short linker. These conjugates can be used as substrates for various kinds of polymerizing enzymes in the enzymatic synthesis of nucleic acids. In particular, these compounds can be used for labeling nucleic acids.

43 Claims, 51 Drawing Sheets

A)

B)

A)

B)

C)

D)

LEGEND:

|  |  |  |  |
|---|---|---|---|
| NUC-COMPONENT | LINKER-COMPONENT | CORE COMPONENT | MARKER UNIT WITH A LINKER |

A)

MARKER

B)

MARKER

LEGEND:

NUC-COMPONENT   LINKER COMPONENT   SIGNAL GIVING MARKER UNIT

A)

B)

NUCLEIC ACID AS A CORE COMPONENT

C)

LEGEND:

NUC-COMPONENT    LINKER COMPONENT    SIGNAL GIVING MARKER UNIT    NUCLEIC ACID WITH ONE SIGNAL GIVING MARKER UNIT

A)

B)

LEGEND:

NUC-COMPONENT    LINKER COMPONENT    SIGNAL GIVING MARKER UNIT    BRANCHED POLYMER AS A CORE COMPONENT E.G. DENDRIMER

A)

B)

LEGEND:

NUC-COMPONENT   LINKER COMPONENT   MARKER COMPONENT
                WITH A CLEAVABLE
                COMPOUND

A)

B)

A)

B)

C)

A)

B)

C)

A)

B)

C)

A)

B)

C)

LEGEND:

dUTP AS A NUC-COMPONENT

STREPAVIDIN AS A
MARKER COMPONENT

FLUORESCENT DYE

LINKER COMPONENT

LEGEND:

dUTP AS A NUC-COMPONENT

LINKER COMPONENT

STREPAVIDIN-ENZYME CONJUGATE
AS A MARKER COMPONENT

LEGEND:

dUTP AS A NUC-COMPONENT

LINKER COMPONENT

STREPAVIDIN ATTACHED TO
QUANTUM DOT

A)

B)

POLY-dA AS A CORE COMPONENT

LEGEND:

dUTP AS A NUC-COMPONENT

STREPAVIDIN-OLIGONUCLEOTIDE
AS A MARKER COMPONENT

FLUORESCENT DYE

LINKER COMPONENT

LABELED OLIGONUCLEOTIDE
AS A MARKER UNIT

LEGEND:

dUTP AS A NUC-COMPONENT

STREPAVIDIN
AS A MARKER COMPONENT

FLUORESCENT DYE

LINKER COMPONENT WITH A
CLEAVABLE COMPOUND

A)

B)

NUCLEIC ACID AS A CORE COMPONENT

C)

NUCLEIC ACID AS A CORE COMPONENT

LEGEND:

dCTP AS A NUC-COMPONENT   OLIGONUCLEOTIDE dT30   LINKER COMPONENT

MACROMOLECULAR NUCLEOTIDE COMPOUNDS AND METHODS FOR USING THE SAME

RELATED APPLICATIONS

This application is a U.S. National Phase under 35 U.S.C. §371 of international Application No. PCT/EP2006/002461, filed on Mar. 17, 2006, which in turn claims the benefit of German Patent Application No. DE 10 2005 012 301.5, filed on Mar. 17, 2005, the disclosures of which Applications are incorporated by reference herein.

This application is also a continuation-in-part and claims the benefit of U.S. application Ser. No. 10/578,313, filed on May 3, 2006, which is a U.S. National Phase under 35 U.S.C. §371 of International Application No. PCT/EP2004/012556, filed on Nov. 5, 2004, which in turn claims the benefit of German Patent Application No. DE 103 51 636.0, filed on Nov. 5, 2003 and DE 103 56 837.9, filed on Dec. 5, 2003, the disclosures of which Applications are incorporated by reference herein.

DESCRIPTION OF THE INVENTION

1. Introduction 1.1. Technical Field

One aspect of the invention relates to the structure, the manufacturing and the application of modified nucleotide and nucleoside components, hereinafter called "nuc-macromolecules".

1.2. State of the Art

Substances with low molecular weight play an important role in living organisms. They act for example as building blocks of polymers, as messengers and as energy carriers. They are used in the field of diagnostics for analysis of parameters with medical relevance. In such procedures, these substances are often labeled with signal carriers. One example for said substances are nucleotides and nucleosides with low molecular weight.

They also play a central role in different metabolic processes in living organisms. ("Biochemie and Pathobiochemie", G. Löffler, 2003) and represent compounds often used in modern biotechnology ("Molecular-Cloning", J. Sambrook, Volume 1-3, 2001, ISBN 0-87969-576-5), for example in artificial detection systems ("DNA Microarrays", Bowtell, 2003, ISBN 0-87969-624-9, "Microarray-Biochip Technology" M Schena, 2000, ISBN 1-881299-37-6). For these reasons, modified nucleotides and nucleotide-analogs are used in various fields of biotechnology, medicine and pharmacology ("Nucleotide Analogs" Scheit, 1980, ISBN 0-471-04854-2, "Nucleoside and Nucleic Acid Chemistry", Kisakürek 2000, "Anti-HIV Nucleosides" Mitsuya, 1997, "Nucleoside Analogs in cancer therapy", Cheson, 1997).

One of the important fields of modern life-science is the analysis of nucleic acids. One large part of this field is dedicated to the detection of nucleic acids and their components in biological samples. In many cases, labeled reaction components, which can react with the nucleic acid to be analyzed, are used. Different labeling procedures for the labeling of nucleic acids are known to the person skilled in the art. On the one hand, individual building blocks of the nucleic acids, i.e. nucleotides or nucleosides, can be modified, on the other hand, short fragments of nucleic acids, oligonucleotides or polynucleotides, can be used for the detection.

Conventionally modified nucleotides are disclosed for example in Lee et al. Nucleic acid research 1992, v. 20, p. 2471; Augustin et. al. J. Biotechnology 2001 v. 86, p. 289-301; U.S. Pat. No. 4,828,979; Held et al. Nucleic acid research, 2002, v. 30, p. 3857. Such modified nucleotides may include a detectable part of low molecular weight that can be detected directly (e.g. fluorescent dye molecule) or indirectly (e.g. biotin molecule that can be detected only after coupling to a streptavidin-dye conjugate). Such nucleotides represent examples of the state-of-the-art modifications of the nucleotides. Many modified nucleotides can be purchased, e.g. from NEN Life Science Products (Biotin-11-dUTP, DNP-11-dATP, Fluorescein-12-dCTP), Amersham Bioscience (dCTP-Cy3, dCTP-Cy5) or Roche (Biotin-16-dUTP). Corresponding detection reagents, e.g. labeled streptavidin and labeled antibodies, can be purchased from the same suppliers.

For the clearness and simplification of the description, focus will be placed on modified nucleotides. To a person skilled in the art, it should be obvious that modified nucleosides can also be used in enzymatic and non-enzymatic synthesis reactions (conventional modified nucleosides can be purchased from Trilink Biotechnologies or Eurogentec). Conventionally modified nucleotides have an aquimolar ratio between the nucleotide component and the low-molecular-weight detectable part, e.g. fluorescent dye or biotin molecule. A linker with an averaged length of 5 to 30 atoms connects both parts. Such nucleotides can be incorporated into the growing strand of nucleic acids by polymerases, introducing a signal-carrying molecule (e.g. dye) or signal-transmitting molecule (e.g. biotin or digoxigenin) into the nucleic acid chain. Signal detection can take place directly after incorporation of dye modified nucleotides or after incubation with a secondary signal-carrying molecule (e.g. streptavidin dye conjugate in the case of biotin). Frequently, the yield of the subsequent coupling of signal-carrying molecules, like streptavidin, is insufficient (20-60%).

Signal multiplication steps are often used in the labeling procedures of nucleic acids. These steps can be applied in different stages of the analysis. Material amplification (e.g. PCR), multiple incorporation of labeled nucleotides or multistep subsequent labeling of biotin nucleotides are examples for signal multiplication ("Molecular-Cloning", J. Sambrook, Volumes 1-3, 2001, ISBN 0-87969-576-5). Such procedures may lead to distortion of the signals, because such procedures imply multiple, often insufficiently controlled steps with different yields, and may be influenced by many factors.

Certain procedures, described for example in Seeger WO 0018956 and Kartalov WO 02072892, rely on the detection of signals from single nucleotide molecules. When conventional nucleotides are used, several phenomena, e.g. bleaching or blinking, affect the results of the single molecule detection. An increase in signal strength and intensity could be important in lowering the error rate for such methods.

There is a demand for modified nucleotides or nucleosides with a better signal-giving or signal-transmitting features, especially in the field of labeling nucleic acids for the analysis.

SUMMARY OF THE INVENTION

One object of the invention is therefore to provide modified nucleotides or nucleosides that retain their substrate properties towards polymerases or other enzymes and have improved signal intensity after being incorporation into the nucleic acids.

Another object of the invention is to provide methods for the labeling of nucleic acids with nucleotides modified according to the invention.

The present invention discloses, in one embodiment, a new class of modified nucleotides, called "nuc-macromolecules". Nuc-macromolecules are characterized in that the one or several nucleotide-components are attached to one or several signal-giving or signal-transmitting macromolecular components (markers) via a linker. Individual nuc-components retain their substrate properties in a nuc-macromolecule towards enzymes. A signal-giving macromolecular component carries several dye molecules, for example.

Nuc-macromolecules can be used like conventional modified nucleotides in different areas of biotechnology or medicine. For the purpose of demonstration, methods for labeling nucleic acids are provided. Other applications of modified nucleotides are already known to the person skilled in the art, as described above.

BRIEF DESCRIPTION OF THE DRAWINGS

In FIG. 8B the polymers are modified with marker units.

DETAILED DESCRIPTION OF THE INVENTION 1.3 Terms and Definitions 1.3.1 Macromolecular compound—a molecule or complex of molecules or a nanocrystal or nanoparticle, which has a molecular weight between 2 kDa and 20 kDa, 2 kDa and 50 kDa, 2 kDa and 100 kDa, 100 kDa and 200 kDa, 200 kDa and 1000 kDa or 1 MDa and 100 MDa or 100 MDa and 100 Gda. Examples of macromolecular compounds are nucleic acids, e.g. oligonucleotides with a length of more than 10 nucleotides, polynucleotides, polypeptides, proteins or enzymes, quantum dots, polymers like PEG, Mowiol, dextran, polyacrylate, nanogold particles and complexes comprising several macromolecules.

1.3.2 Low-molecular compound—a molecule or a molecule complex, which has a mass smaller than 2000 Da (2 kDa), e.g. biotin, natural nucleotides, dATP, dUTP, many dyes, like Cy3, rhodamine, fluorescein and conventionally modified nucleotides, like biotin-16-dUTP.

Figure 1:
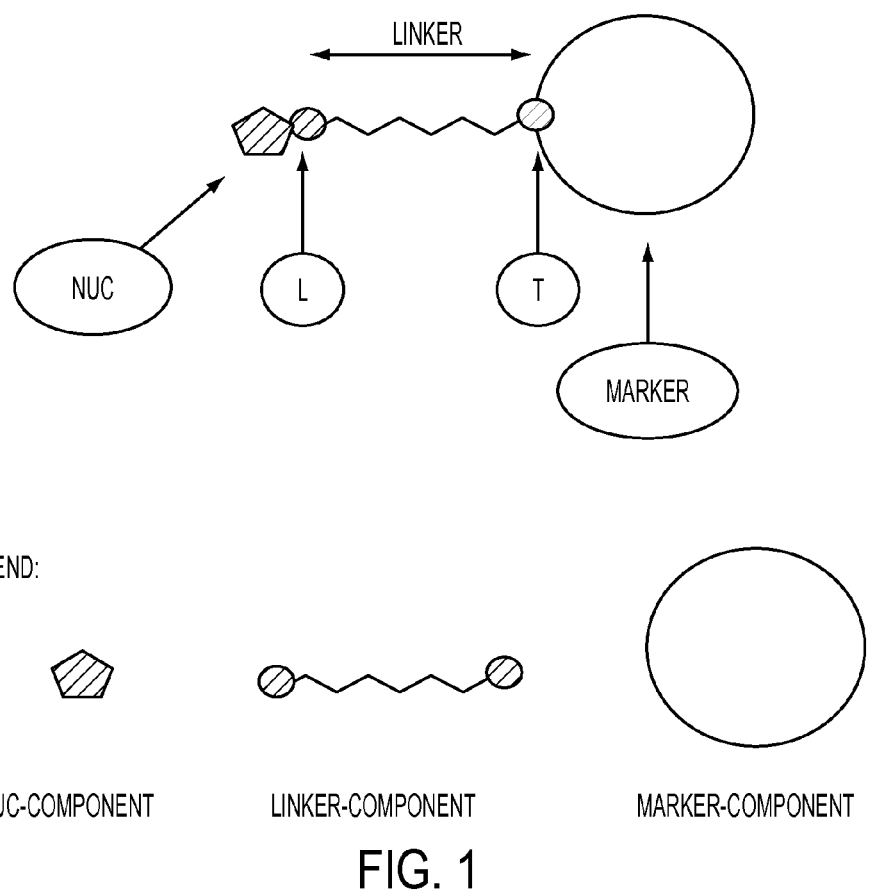
FIG. 1 is the chemical structure of a nuc-macromolecule of the invention.
Figure 2:
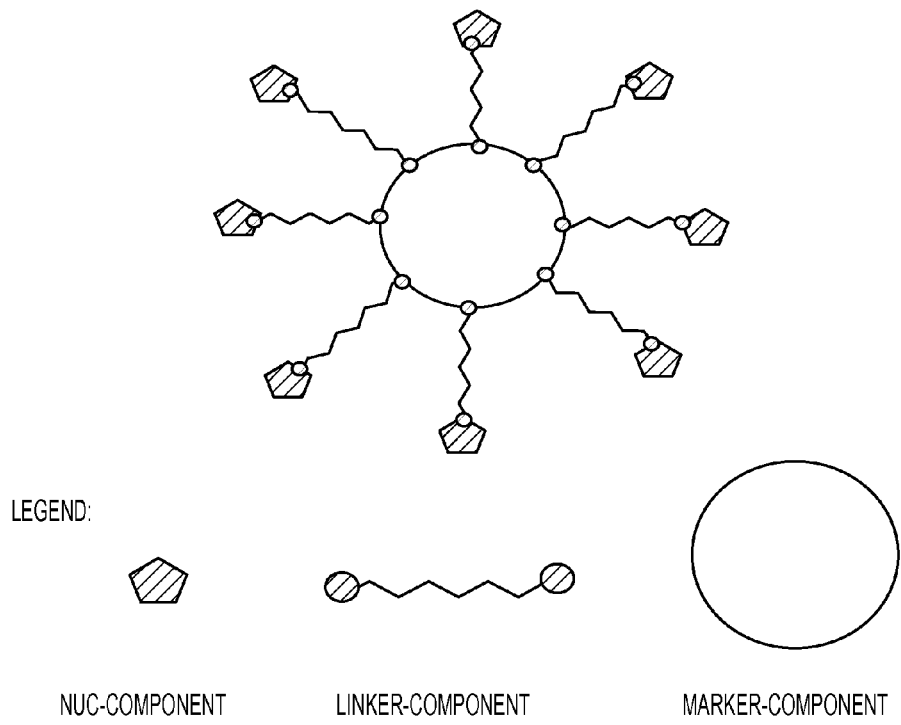
FIG. 2 is the structure of a nuc-macromolecule of the invention comprising multiple nuc-components, multiple linker components and a marker component.

1.3.3 A nuc-macromolecule within the meaning of this application is a chemical structure, which comprises one or more nuc-components, one or more linker components, and a marker component, FIG. 1 or 2:

(Nuc-Linker)$_n$-Marker wherein:
Nuc—is a nuc-component
Linker—is a linker component
Marker—is a marker component
n—is a positive integer from 1 to 1000

In one embodiment of the invention, the linker is water-soluble. Its composition is not restricted as long as substrate properties of the nucleotides are not lost. Its length ranges between 2 and 100,000 atoms.

In a further embodiment, the linker component comprises a coupling unit (L) for coupling the linker to the nuc-component, a water soluble polymer and a coupling unit (T) for coupling the linker to the marker component. In this preferred embodiment, a nuc-macromolecule has the following structure, FIG. 1 or 2:

(Nuc-L-Polymer-T)$_n$-Marker where:
Nuc—is a nucleotide monomer or a nucleoside monomer (nuc-component)
L—is a part of the linker that represents a linkage between nuc and the rest of the linker (coupling unit L)
T—is a part of the linker that represents a linkage between the rest of the linker and the marker (coupling unit T)
Polymer—is a part of the linker that is a water-soluble polymer with an average length between 5 and 100,000 atoms. (In this embodiment, the coupling unit (L), the polymer and the coupling unit (T) are combined as the linker component)
Marker—is a marker component
n—is a positive integer from 1 to 1000, wherein (n) can represent an average number.

Nuc-macromolecules are defined by a combination of one or more nuc-component, respectively, one or more long linker component and one marker component.

1.3.3.1 Nuc-Component

A nuc-component can represent a nucleotide as well as a nucleoside. In the following, nucleotides will be described. For a person skilled in the art it may occur obvious that nucleosides can also be modified in a corresponding manner and used in corresponding reactions.

In one embodiment, the nuc-component is a nucleotide monomer or a nucleoside monomer, which is coupled to the linker component. In principle, all conventional nucleotide variants that are suitable as a substrate for nucleotide-accepting enzymes can serve as nuc-component of the nuc-macromolecule so that naturally occurring nucleotides as well as modified nucleotides (nucleotide analogs) can be considered for the nuc-component. Modified nucleotides comprise base-, sugar- or phosphate-modified nucleotide analogs, FIG. 3. Many examples are known to the person skilled in the art ("Advanced organic chemistry of nucleic acids", 1994, Shabarova, ISBN 3-527-29021-4, "Nucleotide Analogs" Scheit, 1980, ISBN 0-471-04854-2, "Nucleoside and Nucleic Acid Chemistry", Kisakürek 2000, "Anti-HIV Nucleosides" Mitsuya, 1997, "Nucleoside Analogs in cancer therapy", Cheson, 1997); further examples for modifications of the nucleotides will also be cited in the text.

The nuc-component preferably comprises a base part (base), a sugar part (sugar) and optionally a phosphate part (phosphate). Base, sugar and phosphate can be modified, i.e. the basic structure resembles the natural occurring nucleotides, but comprises e.g. additional chemical groups. Examples for combinations of different nucleotide components are known to the person skilled in the art. Such nuc-components can be used in a variety of enzymatic and chemical reactions (G. Wright et al. Pharmac. Ther. 1990, v. 47, p. 447-).

In another embodiment, the nuc-component is coupled with other nucleotides, e.g. in a nucleic acid chain. In this embodiment, the nuc-component acts as a monomer of a polymer.

1.3.3.1.1 Variations of the Phosphate

In one embodiment the nuc-component is a nucleoside. In another embodiment the nuc-component represents a nucleoside-monophosphate. In another embodiment the nuc-component represents a nucleoside-diphosphate. In another embodiment the nuc-component is a nucleoside-triphosphate. Still higher numbers of phosphate groups in a nucleotide (e.g. tetraphosphate etc.) can be used.

The said phosphate modifications can be located at the 5'-position of the sugar, like nucleoside-triphosphates, or also at other positions of the sugar part of the nucleotide, e.g. at the 3'-position.

Optionally, the phosphate part of the nucleotide can comprise modifications, in one embodiment such modifications comprising a linker, for example (D. Jameson et al. Methods in Enzymology 1997, v. 278, p. 363-, A. Draganescu et al. J. Biol. Chem. 2000 v. 275, p. 4555-). In another embodiment of the invention, the phosphate part of the nuc-component comprises thiotriphosphate derivates (Burges et al. PNAS 1978 v. 75, p. 4798-).

In another embodiment of the invention, the phosphate part of the nuc-component comprises protected phosphate groups (e.g. phosphoroamidites).

In one embodiment, the phosphate part represents a linkage between the nuc-component and the linker component of the nuc-macromolecule.

1.3.3.1.2 Variations of the Base

The nuc-component can be natural nucleotide or nucleoside occurring in the nucleic acids in nature or their analogs, preferably participating at the Watson-Crick base-pairing, e.g. adenine, guanine, thymine, cytosine, uracil, inosine or modified bases like 7-deazaadenine, 7-deazaguanine, 6-thioadenine (as referred above). Optionally, the base comprises modifications. In one embodiment, such modifications comprise for example a linker, e.g. amino-propargyl-linker or amino-allyl-linker. Further examples of linkers are known (Ward et al. U.S. Pat. No. 4,711,955, G. Wright et al. Pharmac. Ther. 1990, v. 47, p. 447-, Hobbs et al. U.S. Pat. No. 5,047,519 or other linkers e.g. Klevan U.S. Pat. No. 4,828,979, Seela U.S. Pat. No. 6,211,158, U.S. Pat. No. 4,804,748, EP 0286028, Hanna M. Method in Enzymology 1996 v. 274, p. 403, Zhu et al. NAR 1994 v. 22 p. 3418, Jameson et al. Method in Enzymology, 1997, v. 278, p. 363-, Held et al. Nucleic acid research, 2002, v. 30 p. 3857-, Held et al. Nucleosides, nucleotides & nucleic acids, 2003, v. 22, p. 391, Short U.S. Pat. No. 6,579,704, Odedra WO 0192284). In one embodiment, a linker coupled to the base represents a connection part between the nuc-component and the linker component of the nuc-macromolecule. Further modifications of the base are described for example in the catalogue of Trilink Biotechnologies, Inc. San Diego, USA, Issue 2003, page 38.

1.3.3.1.3 Variations of the Sugar

Different variations of the sugar part of the nucleotides, which are used e.g. in the diagnostics, therapy or research, are known to the person skilled in the art. Such variations comprise ribose, 2'-deoxyribose or 2',3'-dideoxyribose. Optionally, the sugar part comprises modifications (M. Metzker et al. Nucleic Acid Research 1994, v. 22, p. 4259-, Tsien WO 91/06678). In one embodiment, such modifications comprise for example a linker. The modifying group can be optionally be reversibly coupled to the sugar part (Hovinen et al. J. Chem. Soc. Prking Trans. 1994, s. 211-, Canard U.S. Pat. No. 5,798,210, Kwiatkowski U.S. Pat. No. 6,255,475, Kwiatkowski WO 01/25247, Ju et al. U.S. Pat. No. 6,664,079, Fahnestock et al. WO 91066678, Cheeseman U.S. Pat. No. 5,302,509, Parce et al. WO 0050642, Milton et al. WO 2004018493, Milton et al. 2004018497).

In one embodiment, the linker coupled to the sugar part represents the connection between the nuc-component and the linker component of the nuc-macromolecules.

In another embodiment, the sugar part comprises for example the following modifications: optionally the 3'—OH-Group or the 2'—OH-Group can be substituted by the following atoms or groups: halogen atoms, hydrogen atoms, amino- or mercapto- or azido groups (Beabealashvilli et al. Biochem Biophys Acta 1986, v. 868, p. 136-, Yuzhanov et al. FEBS Lett. 1992 v. 306, p. 185-).

In another embodiment, the nuc-component comprises acyclic nucleotide or nucleoside modifications (A. Holy Current Pharmaceutical Design 2003 v. 9, p. 2567-, G. Wright et al. Pharmac. Ther. 1990, v. 47, p. 447-). In another embodiment, the sugar part comprises a double bond.

In this application, the following abbreviations will be used for 2'-deoxynucleotides: dUTP for 2'-deoxyuridine-triphosphate, dCTP for 2'-deoxycytidine-triphosphate, dATP for 2'-deoxyadenosine-triphosphate, dGTP for 2'-deoxyguanosine-triphosphate.

1.3.3.1.4 Linking of the Nucleotide and Linker

The nuc-component is linked to the linker at a coupling position. This coupling position of the linker on the nuc-component can be located on the base, on the sugar (e.g. ribose or deoxyribose) or on the phosphate part.

The linkage between the linker component and the nuc-component is preferably covalent.

If the coupling position is on the base, then the following positions are preferable: position 4 or 5 for pyrimidine bases and positions 6, 7, 8 for purine bases. (Ward et al. U.S. Pat. No. 4,711,955, G. Wright et al. Pharmac. Ther. 1990, V. 47, S. 447-, Hobbs et al. U.S. Pat. No. 5,047,519 oder andere Linker z. B. Klevan U.S. Pat. No. 4,828,979, Seela U.S. Pat. No. 6,211,158, U.S. Pat. No. 4,804,748, EP 0286028, Hanna M. Method in Enzymology 1996 v. 274, S.403, Zhu et al. NAR 1994 v. 22 S.3418, Jameson et al. Method in Enzymology, 1997, v. 278, S. 363-, Held et al. Nucleic acid research, 2002, v. 30 3857-, Held et al. Nucleosides, nucleotides & nucleic acids, 2003, v. 22, S. 391, Short U.S. Pat. No. 6,579,704, Odedra WO 0192284). On sugar, positions 2', 3', 4' or 5' can serve as coupling positions. The coupling to the phosphate groups can proceed via alpha, beta, or gamma phosphate groups. Examples for coupling positions on the base are described in Short WO 9949082, Balasubramanian WO 03048387, Tcherkassov WO 02088382 (also see commercially available nucleotides e.g. from Amersham or Roche), on the ribose in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Parce WO 0050642, on phosphate groups in Jameson et al. Method in Enzymology, 1997, v. 278, p. 363.

The location of the coupling position depends on the area of application of the nuc-macromolecules. For example, coupling positions on the sugar or on the base are preferable in cases where the marker is intended to stay coupled to the nucleic acid strand. The coupling to the gamma or beta phosphate groups can be used for example in cases where the marker has to be separated during the incorporation of the nuc-macromolecule.

The linking between the nuc-component and the linker component results for example via a coupling unit (L) that is a part of the linker component.

In one embodiment, the linkage between the nuc-component and the linker is stable, e.g. resistant to temperatures up to 130° C., pH-ranges from 1 to 14 and/or resistant to hydrolytical enzymes (e.g. proteases or esterases). In another embodiment of the invention, this linkage between the nuc-component and the linker component is cleavable under mild conditions.

This cleavable linkage allows removal of the linker components and the marker components. This can be advantageous for example for methods of sequencing by synthesis, like pyrosequencing, BASS (base addition sequencing schema) (Canard et al.

U.S. Pat. No. 5,798,210, Rasolonjatovo Nucleosides & Nucleotides 1999, v. 18, p. 1021, Metzker et al. NAR 1994, v. 22, p. 4259, Welch et al. Nucleosides & Nucleotides 1999, v. 18, p. 19, Milton et al. WO 2004018493, Odedra at al. WO 0192284) or single molecule sequencing Tcherkassov WO 02088382. The choice of the cleavable linkage is not restricted insofar as it remains stable under conditions of enzymatic reaction, does not result in irreversible damage of the enzyme (e.g. polymerase) and is cleavable under mild conditions. "Mild conditions" is understood to mean conditions that do not result in damage of nucleic acid-primer complexes wherein, for example, the pH-range is preferably between 3 and 11 and the temperature is between 0° C. and the temperature value (x). This temperature value (x) is dependent upon the Tm of the nucleic acid-primer complex (where Tm is the melting temperature) and is calculated for example as Tm (nucleic acid primer complex) minus 5° C. (e.g. Tm is 47° C., then the (x)-value is 42° C.; ester, thioester, acetales, phosphoester, disulfide linkages and photolabile compounds are suitable as cleavable linkages under these conditions).

Preferably, the said cleavable linkage comprises chemical or enzymatic cleavable linkages or photolabile compounds. Ester, thioester, disulfide and acetal linkages are preferred as examples of chemical cleavable groups (Short WO 9949082, "Chemistry of protein conjugation and crosslinking" Shan S. Wong 1993 CRC Press Inc., Herman et al. Method in Enzymology 1990 v. 184 p. 584, Lomant et al. J. Mol. Biol. 1976 v. 104 243, "Chemistry of carboxylic add and esters" S. Patai 1969 Interscience Publ.). Examples for photolabile compounds are described in Rothschild WO 9531429, "Protective groups in organic synthesis" 1991 John Wiley & Sons, Inc., V. Pillai Synthesis 1980 p. 1, V. Pillai Org. Photochem. 1987 v. 9 p. 225, Dissertation "Neue photolabile Schutzgruppen für die lichtgesteuerte Oligonucleotidsynthese" H. Giegrich, 1996, Konstanz, Dissertation "Neue photolabile Schutzgruppen für die lichtgesteuerte Oligonucleotidsynthese" S. M. Bühler, 1999, Konstanz).

1.3.3.1.5 Number of the Linked Nuc-Components

In one embodiment of the invention, only one nuc-component is coupled per nuc-macromolecule. In another embodiment of the invention, several nuc-components are coupled per nuc-macromolecule. If several nuc-components are coupled, they can be identical or different, whereas the average number of the nuc-components per nuc-macromolecule can range for example from 2 to 5, 5 to 10, 10 to 25, 25 to 50, 50 to 100, 100 to 250, 250 to 500, 500 to 1000.

1.3.3.2 Linker Component

The terms "linker" and "linker component" will be used synonymously in this application and comprise the whole structural part of the nuc-macromolecule between the nuc-component and the marker component.

The linker is preferably water-soluble. The precise linker composition is not limited and can vary. In a preferred embodiment, nuc-macromolecules have a short linker. Its length is between 2 and 30 chain atoms. Such linkers can carry functional groups, as for example amino, carboxy, mercapto and hydroxy groups. Further molecules, e.g., macromolecules, like water-soluble polymers, can be coupled to these groups. Examples of short linkers coupled to the nucleotides are known to the person skilled in the art. (Ward et al. U.S. Pat. No. 4,711,955, G. Wright et al. Pharmac. Ther. 1990, V. 47, S. 447-, Hobbs et al. U.S. Pat. No. 5,047,519 or other linkers e.g. Klevan U.S. Pat. No. 4,828,979, Seela U.S. Pat. No. 6,211,158, U.S. Pat. No. 4,804,748, EP 0286028, Hanna M. Method in Enzymology 1996 v. 274, S. 403, Zhu et al. NAR 1994 v. 22 S. 3418, Jameson et al. Method in Enzymology, 1997, v. 278, S. 363-, Held et al. Nucleic acid research, 2002, v. 30 3857-, Held et al. Nucleosides, nucleotides & nucleic acids, 2003, v. 22, S. 391, Short U.S. Pat. No. 6,579,704, Odedra WO 0192284). The linker can contain one or several units of water-soluble polymers, as for example amino acids, sugars, PEG units or carboxylic acids. The coupling unit (L) of a long linker can serve as further examples of short linkers (see below). Linkers with the length between 2 and 20 atoms are preferably used in nuc-macromolecules whose marker component comprises linear water-soluble polymers. In another preferred embodiment of the invention, a long linker having a length of more than 30 chain atoms is used.

Examples for the composition of the linker will now be presented below.

1.3.3.2.1 Parts of the Linker

The linker is a part of the nuc-macromolecule between the corresponding nuc-component and marker component.

The linker comprises for example the following parts in its structure:

1) coupling unit (L)
2) water soluble polymer
3) coupling unit (T)

The subdivision of the linker in separate parts is purely functional and should serve merely for better understanding of the structure. Depending on the approach, particular structures can be considered as one functional part or as another.

The coupling unit (L) has the function of linking the linker component and the nuc-component. Short, non-branched compounds from 1 to 20 atoms in length are preferred. The particular structure of the coupling unit (L) depends on the coupling position of the linker to the nucleotide and on the particular polymer of the linker. Several examples of coupling units (L) are shown in examples 1 to 33 of this application. Many conventionally modified nucleotides comprise a short linker; these short linkers are further examples of coupling units (L), e.g. short linker on the base: Short WO 9949082, Balasubramanian WO 03048387, Tcherkassov WO 02088382 (see also commercially available nucleotides from e.g. Amersham or Roche), short linker on the ribose as described in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Ju et al. U.S. Pat. No. 6,664,079, Parce WO 0050642, and short linker on phosphate groups as described in Jameson et al. Method in Enzymology, 1997, v. 278, p. 363.

Still further examples for the coupling unit (L) are presented in the following:

$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—$R_7$, $R_6$—(CH$_2$)$_n$—$R_7$, $R_6$-A-(CH$_2$)$_n$—$R_7$, $R_6$—(CH$_2$)$_n$—B—$R_7$, $R_6$—(CH=CH—)$_n$—$R_7$, $R_6$-(A-CH=CH—)$_n$—$R_7$, $R_6$—(CH=CH—B—)$_n$—$R_7$, $R_6$-A-CH=CH—(CH$_2$—)$_n$—$R_7$, $R_6$—(—CH=CH—CH$_2$)$_n$—B—$R_7$, $R_6$—(—CH=CH—CH$_2$—CH$_2$)$_n$—B—$R_7$, $R_6$—(C≡C—)$_n$—$R_7$, $R_6$-(A-C≡C—)$_n$—$R_7$, $R_6$—(C≡C—B—)$_n$—$R_7$, $R_6$-A-C≡C—(CH$_2$—)$_n$—$R_7$, $R_6$—(—C≡C—CH$_2$)$_n$—B—$R_7$, $R_6$—(—C≡C—CH$_2$—CH$_2$)$_n$—B—$R_7$, where $R_6$ is the nuc-component; $R_7$ is a polymer; A and B comprises the following structural elements: —NH—, —O—, —S—, —SS—, —CO—NH—, —NH—CO—, —CO—O—, —O—CO—, —CO—S—, —S—CO—, —P(O)$_2$—, —Si—, —(CH$_2$)$_n$—, a photolabile group; (n) is a number from 1 to 5

The coupling unit L is linked to the nuc-component on the one side and to the polymer on the other. The character of the linkage with the polymer depends on the kind of polymer. In a preferred embodiment, the ends of the polymer comprises reactive groups, for example NH2 (amino), OH (hydroxy), SH (mercapto), COOH (carboxy), CHO (aldehyde), acrylic, maleimide or halogen groups. Such polymers are commercially available (e.g. Fluka). Some examples for the coupling of polymers to the coupling unit are shown in the examples 1 to 33.

In a preferred embodiment, the water-soluble polymer represents the major part of the linker component. It is a polymer, preferably hydrophilic, consisting of the same or different monomers.

Examples of suitable polymers are polyethylene-glycol (PEG), polyamides (e.g. polypeptides), polysaccharides and their derivates, dextran and its derivates, polyphosphates, polyacetates, poly(alkyleneglycols), copolymers with ethyleneglycol und propyleneglycol, poly(olefinic alcohols), poly(vinylpyrrolidones), poly(hydroxyalkylmethacrylamides), poly(hydroxyalkylmethacrylates), poly(x-hydroxy acids), polyacrylic acid and their derivates, poly-acrylamide and its derivates, poly(vinylalcohol), polylactic acid, polyglycolic acid, poly(epsilon-caprolactones), poly(beta-hydroxybutyrates), poly(beta-hydroxyvalerate), polydioxanones, poly(ethylene terephthalates), poly(malic acid), poly(tartronic acid), poly(ortho esters), polyanhydrides, polycyanoacrylates, poly(phosphoesters), polyphosphazenes, hyaluronidate, and polysulfones.

In one embodiment, the polymer-part comprises branched polymers. In an other embodiment, the polymer-part comprises non-branched or linear polymers. The polymer can consist of several parts of different length, each part consisting of the same monomers with the monomers in different parts being different. To a person skilled in the art, it should seem obvious that for a macromolecular linker, it is often possible to determine only an average mass, so that the data regarding the mole masses represent an average ("Makromoleküle, Chemische Struktur und Synthesen", Volume 1, 4, H. Elias, 1999, ISBN 3-527-29872-X). For this reason, often there is no exact mass information for nuc-macromolecules.

In one preferred embodiment, the linker component comprises a linear, non-branched polymer that is not modified with further sterically demanding chemical structures such as dyes, fluorescent dyes, or ligands. Such linker components lead to a low sterical hindrance, e.g. in an enzymatic recognition of the nuc-components.

In another preferred embodiment, the polymer of the linker component is linear but the linker component is modified with one or several sterically demanding chemical groups, for example dyes. The presence of the sterically demanding group allows for a control of the enzymatic reaction in some analytic processes (Tcherkassov WO 02088382). Further examples of sterically demanding groups are shown in the paragraph 1.3.19.

Sterically demanding ligands or structures can be coupled to different linker parts. The average number of the sterically demanding ligands coupled to the linker can vary and amounts, for instance, between 1 and 3, 3 and 5, 5 and 20, 20 and 50. In the coupling of sterically demanding groups, it is necessary to take into consideration that a space-demanding structure coupled in the direct proximity of nucleotide-component can lead to the loss of the substrate properties (see example 25). Sterically demanding ligands can be coupled uniformly or randomly over the entire length of the linker, or they can be coupled to the linker at a certain distance from the nuc-component. The distance between the nuc-component and the steric hindrance amounts, for instance, to 10 to 15, to 15 to 20, 20 to 25, 25 to 30, 30 to 35, 35 to 40, 40 to 45, 45 to 50, 50 to 55, 55 to 60, 60 to 70, 70 to 80, 80 to 90, 90 to 100, 100 to 200, 200 to 1000, 1000 to 5000 chain atoms. The sterically demanding group can be considered as a part of the linker or as a part of the marker. Which way to consider it can depend, for instance, on whether or not the sterically demanding group possesses certain signal properties.

1.3.3.2.2 Linker Length

An average linker length amounts to between 2 to 5, 5 to 10, 10 to 20, 20 to 30, 30 to 40, 40 to 50, 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 atoms (chain atoms), so that an average linker length amounts to between 2 to 5, 5 to 10, 10 to 20, to 30, 30 to 40, 40 to 50, 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 angstroms (measured on a molecule potentially stretched-out as much as possible).

If a nuc-macromolecule comprises several linker components, these linker components can be of the same or different lengths relative to each other.

Some parts of the linkers can comprise rigid areas and other parts can comprise flexible areas.

1.3.3.2.3 Linker Coupling in a Nuc-Macromolecule

The linker is connected to the nuc-component on one side and to the marker component on the other side. The linker can have coupling units at his ends which fulfill this connecting function. The connection to the nuc-component was discussed above. The connection between the linker and the marker components is provided by coupling unit T. Short, non-branched connections no more than 20 atoms in the length are preferred. The respective structure of the coupling unit T depends upon the coupling position on the marker component and upon the respective polymer of the linker.

The coupling unit T is covalently connected to the polymer. The kind of the coupling depends on the kind of the polymer. In a preferred embodiment, the polymer has reactive groups, such as NH2 (amino), OH (hydroxy), SH (mercapto), COOH (carboxy), CHO (aldehyde), acrylic, maleimide or halogen groups, at its ends. Such polymers are commercially available (e.g. Fluka). Some examples of the coupling units L are shown in examples 1 to 33. For further examples of the chemical and affine connections please refer to the literature: "Chemistry of protein conjugation and crosslinking" Shan S. Wong in 1993, "Bioconjugation protein coupling techniques for the biomedical sciences", M. Aslam, in 1996.

Figure 9:
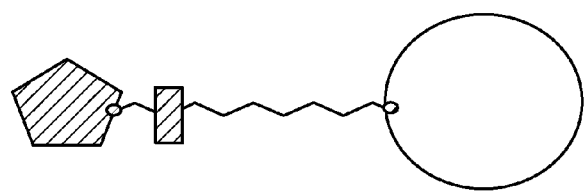
FIGS. 9A and B show embodiments of the invention where the linker comprises other functional groups or parts, for example one or several groups that are cleavable under mild conditions.
Figure 9:
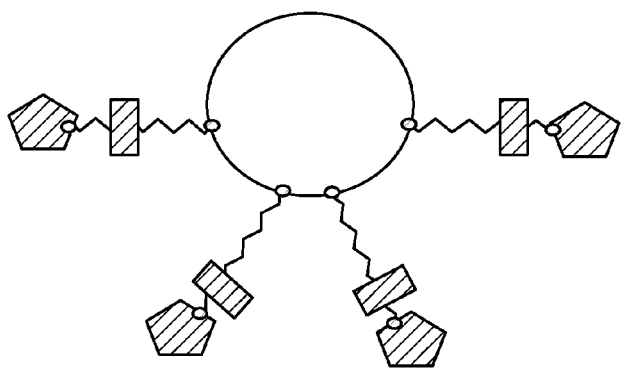
Figure 9:
Figure 9:
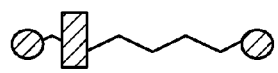
Figure 9:
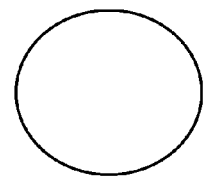

The linker can also comprise other functional groups or parts, for example one or several groups that are cleavable under mild conditions (FIG. 9), see examples 22, 23, 24, 31.

A cleavable group within the linker allows the removal of a part of the linker and the marker component. After a cleavage reaction, a linker residue remains coupled to the nuc-component. Examples of cleavable groups are shown in Section 1.3.3.1.4.

1.3.3.3 Marker Component

The marker component can comprise different structures. The structures individually are not limited, as long as they do not destroy the substrate properties of the nuc-components for enzymes. In preferred embodiments, such structures have a signal-giving or a signal-transmitting function. The marker can also comprise other functions, for instance, structural, anti-toxic or affine function (for instance, as part of medicines or medical preparations).

1.3.3.3.1 The Composition of the Marker Component (Marker)

In one embodiment, the marker comprises a low-molecular marker unit. In an other embodiment, the marker comprises a macromolecular marker unit. In a still further embodiment, the marker comprises several low-molecular marker units. In a still further embodiment, the marker comprises several macromolecular marker units. In a still further embodiment, the marker comprises a combination of low-molecular and macromolecular units. The marker units can have a signal-giving or signal-transmitting function.

These units can be molecules with low molecular mass, e.g. less than 2000 Da, or they can be also macromolecules. The number of the signal-giving or signal-transmitting units, which are combined into one marker component, comprises the following ranges: 1 and 2, 2 to 5, 5 to 20, 20 to 50, 50 to 100, 100 to 500, 500 to 1000, 1000 to 10000, 10000 to 100000.

Figure 4:
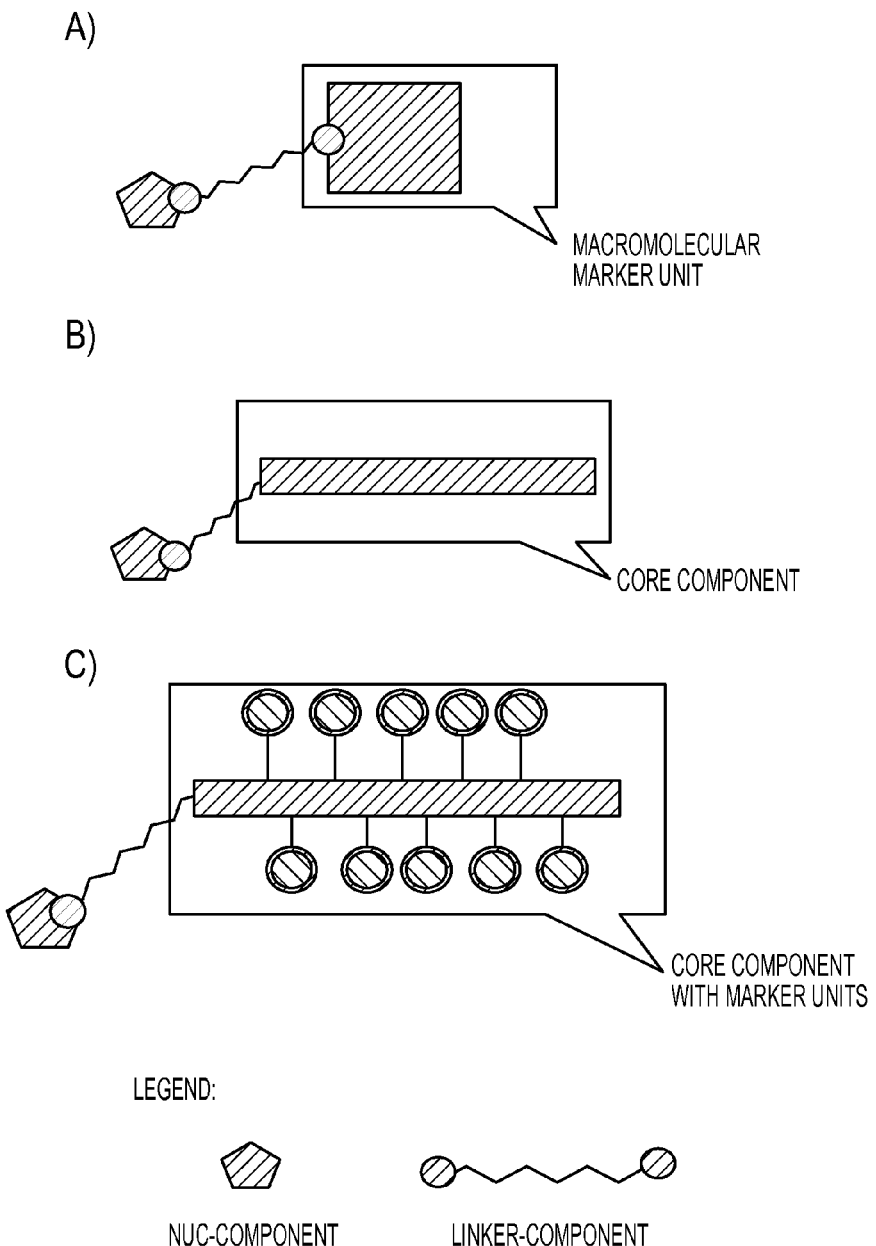
FIGS. 4A, 4B and 4C show an embodiment of the invention where several marker units are combined into one marker component (FIG. 4A); the units are bound to a framework, the core component of the marker (FIGS. 4B, 4C).
Figure 5:
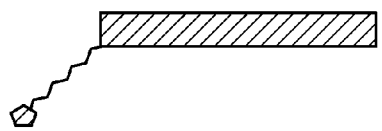
FIGS. 5A-D depict embodiments of the invention where the core component provides the connection to one or several nuc-linker components.
Figure 5:
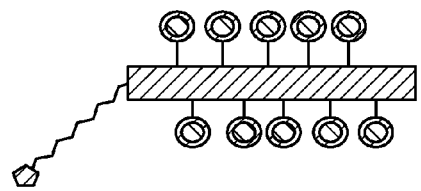
Figure 5:
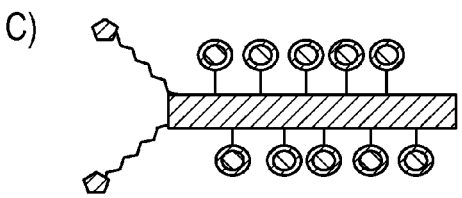
Figure 5:
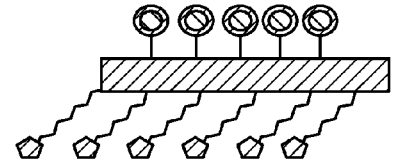
Figure 5:
Figure 5:
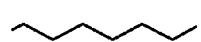
Figure 5:
Figure 5:

If several marker units are combined into one marker component, then in one embodiment these units are bound to a framework, the core component of the marker (FIGS. 4b, c). This core component connects the units together. The core component can provide the connection to one or several nuc-linker components (FIG. 5). The core component comprises low-molecular or macromolecular compounds.

1.3.3.3.2 Structure of the Signal-Giving or the Signal-Transmitting Units of the Marker The structural marker units comprise the following groups:
1.3.3.3.2.1 Structures with Low Molar Mass:

Biotin molecules, hapten molecules (e.g. digoxigenin), radioactive isotopes (e.g., $P^{32}$, $J^{131}$), or their derivatives, rare earth elements, dyes, fluorescent dyes, quencher of the fluorescence (e.g. dabsyl) (many of these molecules are commercially available, e.g., from Molecular Probes, Inc or from Sigma-Aldrich) with the same or different spectral properties, groups of dyes undergoing FRET. Thermochromatic, photochromatic or chemoluminescent substances are available for example from Sigma-Aldrich, chromogenic substances are described for example as substrates for peptidases in "Proteolytic enzymes Tools and Targets", E. Sterchi, 1999, ISBN 3-540-61233-5).

Figure 6:
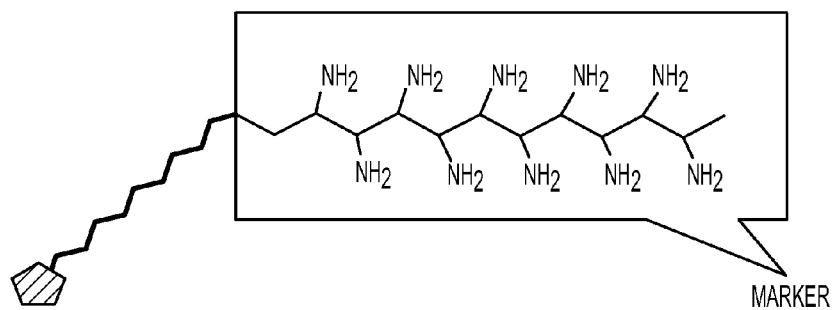
FIG. 6A depicts an embodiment of the invention where reactive amino groups serve as signal-transmitting structural units.
FIG. 6B shows an embodiment of the invention where the reactive groups are modified with signal-giving elements, such as dyes with suitable reactive groups (for instance, NHS esters, mercapto-, amino groups), e.g., after incorporation of nuc-macromolecules.
Figure 6:
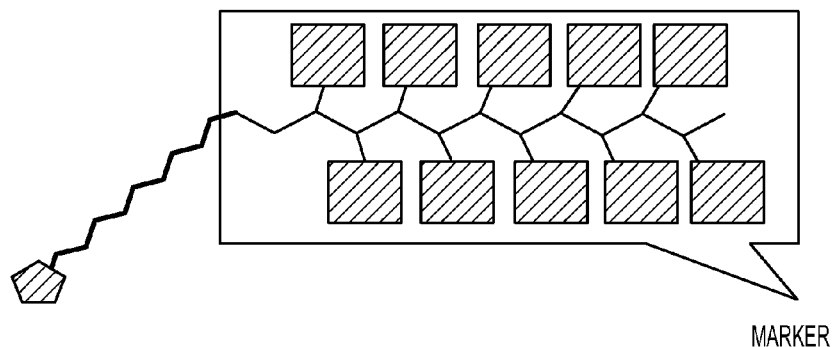
Figure 6:
Figure 6:
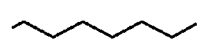
Figure 6:

Also chemically reactive groups, as for example amino-, carboxy-, merkapto-, aldehyde, iodine acetate, acrylic, dithio-, thioester-groups, can serve as signal-transmitting structural units (FIG. 6a). These reactive groups can be modified with signal-giving elements, such as dyes with suitable reactive groups (for instance, NHS esters, mercapto-, amino groups) (FIG. 6b), e.g. after incorporation of nuc-macromolecules. General rules for the choice of a suitable pair of reactive groups are shown In "Chemistry of protein conjugation and crosslinking" Shan S. Wong 1993.

In a special embodiment, a combination comprising one nuc-component, one macromolecular linker component and one marker component with a low molecular weight already fulfils the requirements of the present invention. Such compounds are also subject matter of this invention. They can be used both as intermediate compounds for the chemical synthesis of nuc-macromolecules with one macromolecular marker, e.g., dUTP-PEG-biotin, and as independent compounds for enzymatic reactions, as, for example, nucleotides labeled with only one dye.

Different fluorescent dyes can be used, and their choice is not limited as long as their influence of the enzymatic reaction is not substantial. Examples of such dyes are Rhodamine (Rhodamine 110, Tetramethylrhodamine, available from Fluka-Sigma), cyanine dyes (Cy2, Cy3, Cy3.5, Cy5, Cy5.5, Cy7 available from Amersham Bioscience), coumarine, Bodipy, fluorescein, Alexa Dyes: e.g., Alexa 532, Alexa 548, Alexa 555 (Molecular Probes). Many dyes are commercially available, for instance, from Molecular Probes Europe, Leiden, the Netherlands (hereinafter called Molecular Probes) or from Sigma-Aid rich-Fluka (Taufkirchen, Germany).

Examples of the synthesis of a nuc-macromolecule with a low-molecular marker are given in examples 19, 20, 23, 36, 37, 38.

Figure 7:
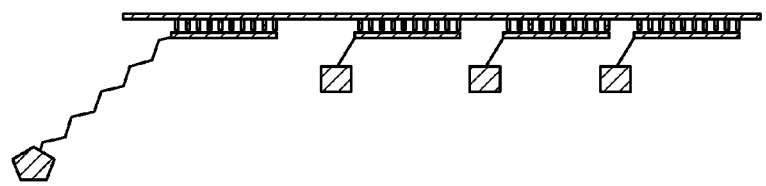
FIGS. 7A-C show embodiments of the invention where nucleic acid chains, including oligonucleotides (modified and non-modified), act as marker units. The nucleic acid chains can carry additional modifications, such as, for example, free amino groups, dyes and other signal-giving molecules, e.g. macromolecular substances, enzymes or nanocrystals (FIGS. 7A, C).
Figure 7:
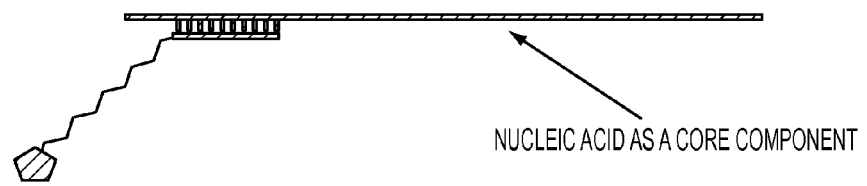
Figure 7:
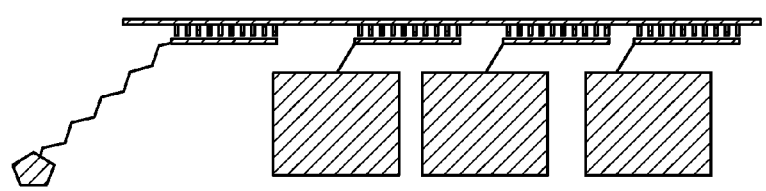
Figure 7:
Figure 7:
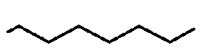
Figure 7:
Figure 7:
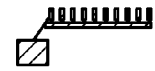

In one embodiment, the marker comprises several marker units. These marker units can have the same or different properties. For instance, fluorescent dyes with different spectral qualities can be used. In one embodiment, the fluorescent dyes that can form FRET pairs are selected.
1.3.3.3.2.2 Structures with High Mass (Macromolecules)
1.3.3.3.2.2.1 Nanocrystals Nanocrystals, e.g. quantum dots, can serve as marker units. Quantum dots with the same or different spectral qualities can be used within the same marker component. Examples of quantum dots are presented in U.S. Pat. No. 6,322,901, U.S. Pat. No. 6,423,551, U.S. Pat. No. 6,251,303, U.S. Pat. No. 5,990,479.
1.3.3.3.2.2.2 Nano- or Micro-Particles Nano- or micro-particles can serve as marker units. The diameters of these particles can range from 1 nm to 2 nm, from 2 nm to 5 nm, from 5 nm to 10 nm, from 10 nm to 20 nm, from 20 nm to 50 nm, from 50 nm to 100 nm, from 100 nm to 200 nm, from 200 nm to 500 nm, from 500 nm to 1000 nm, from 1000 nm to 5000 nm. The material of these particles can, for instance, be pure metals such as gold, silver, aluminum (as instances of particles capable of surface plasmon resonance), Protein-gold_conjugates: J. Anal. Chem. 1998; v. 70, p. 5177-, Nucleic acid-gold_conjugates: J. Am. Chem. Soc. 2001; v. 123, p. 5164-, J. Am. Chem. Soc. 2000; v. 122, p. 9071-, Biochem. Biophys. Res. Commun 2000; v. 274, p. 817-, Anal. Chem. 2001; v. 73, p. 4450-, latex (e.g., Latex-Nano-particles), Anal. Chem. 2000; v. 72, p. 1979-, plastic (Polystyrene), paramagnetic compounds: Zhi Z L et al. Anal. Biochem, 2003; v. 318 (2): p. 236-43, Dressman D et al. Proc Natl Acad Sci U.S.A. 2003, v. 100 (15): p. 8817-22, metal particles, magnetic compounds: Jain K K. Expert Rev Mol Diagn. 2003; v. 3 (2): p. 153-61, Patolsky F et al. Angew Chem Int Ed Engl 2003; v. 42 (21), p. 2372-2376, Zhao X et al. Anal Chem. 2003; v. 75 (14): p. 3144-51, Xu H et al. J Biomed Mater Res. 2003 Sep. 15; v. 66A(4): p. 870-9, Josephson U.S. Patent No. 2003092029, Kliche WO0119405.
1.3.3.3.2.2.3 Protein Molecules Protein molecules can serve as marker units. The proteins comprise the following groups:

enzymes (e.g. peroxidase, alkaline phosphotase, urease, beta-galactosidase, peptidases), fluorescing proteins (e.g. from GFP-family or phycobiliproteins (e.g. Phycoerythrin, Phycocyanin) available e.g. from Molecular Probes Inc.), antigen-binding proteins (e.g. antibodies, tetramers, affibodies (Nord et. al Nature Biotechnology, 1997, v. 15, p. 772-) or their components (e.g. Fab fragments), nucleic acid-binding proteins (e.g. transcription factors).
1.3.3.3.2.2.4 Nucleic Acid Chains Nucleic acid chains, including oligonucleotides (modified and non-modified), can act as marker units. The length of these nucleic acid chains should fall preferably within the following ranges (number of nucleotide monomers in a chain): 10 to 20, 20 to 50, 50 to 100, 100 to 200, 200 to 500, 500 to 1000, 1000 to 5000, 5000 to 10000, 10000 to 100000. DNA, RNA, PNA molecules can be used. Nucleic acid chains can carry additional modifications, such as, for example, free amino groups, dyes and other signal-giving molecules, e.g. macromolecular substances, enzymes or nanocrystals (FIGS. 7a, c). Modified nucleic acid chains are also commercially available, e.g. from MWG-Biotech. Further examples of macromolecules or macromolecular complexes which can be used, according to the scope of the present invention, as a marker or marker units in the marker component are described in the U.S. Pat. No. 4,882,269, the U.S. Pat. No. 4,687,732, WO 8903849, the U.S. Pat. No. 6,017,707, the U.S. Pat. No. 6,627,469. Also other marker units can be used, like lectines, growth factors, hormones, receptor molecules.

1.3.3.3.3 Core Component of the Marker

The core component has the function of connecting several structural elements of the nuc-macromolecules. For instance, the core component connects several marker units together. In a further embodiment, linker components can be bound to the core component (FIG. 5). The term "core-component" is functional and serves for illustration of possible structures of nuc-macromolecules. Different chemical structures that connect linker and marker-units can be called core-component. Examples for constituents of the core component will now be presented.

1.3.3.3.3.1 Constituents of the Core Component

In one embodiment, the core component consists of one or several low molecular compounds. They have the function of connecting the marker units together. A connection between the core component and the marker units can be covalent or affine. With covalent bonding, for instance, compounds with the general structural formula $(F)_m-R-(H)_n$ can act as a precursor, where (F) and (H) are reactive groups and (R) a connecting component. The number of such groups and their assembly can vary considerably. Many examples are known to the expert in the field, e.g. connections from the group of crosslinkers ("Chemistry of protein conjugation and crosslinking" Shan S. Wong in 1993 CRC Press Inc). The structure is not limited. It is preferably water-soluble. For instance, parts (F) and (H) comprise independently the following groups: NH2 (amino), OH (hydroxy), SH (mercapto), COOH (carboxy), CHO (aldehyde), acrylic or maleimide. Water-soluble polymers like PEG or polypeptide chains or short aliphatic chains represent examples for (R).

In a further embodiment, the core component consists of a water-soluble polymer, whereby the said polymer can consist of the same or different monomers.

Figure 8:
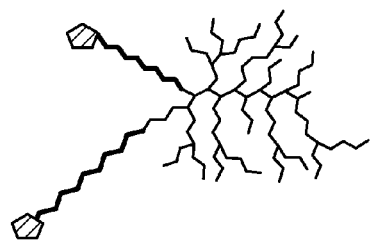
FIGS. 8A and 8B show embodiments of the invention where the core component consists of a water-soluble polymer, whereby the polymer can consist of the same or different monomers.
Figure 8:
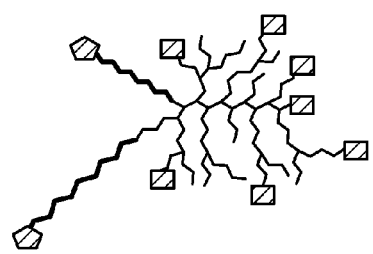
Figure 8:
Figure 8:
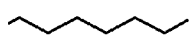
Figure 8:
Figure 8:
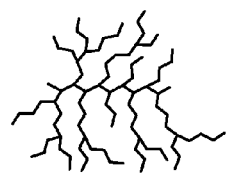

The following polymers and their derivates are examples of parts of the core component: polyamides (e.g. polypeptide like polyglutamin or polyglutamic acid) and their derivates, polyacrylic acid and its derivates, natural or synthetic polysaccharides (e.g. starch, hydroxy-ethyl-starch), dextran and its derivates (e.g. aminodextran, carboxydextran), dextrin, polyacrylamides and their derivates (e.g. N-(2-hydroxypropyl)-methacrylamide), polyvinyl alcohols and their derivates, nucleic acids, proteins. These polymers can be linear, globular, e.g. streptavidin or avidin, or can be branched, e.g. dendrimers (FIG. 8a). Also, cross-connected, soluble polymers, for instance, crosslinked polyacrylamides (crosslinker bisacrylamide in combination with polyacrylamide), are suitable.

Since the linker component as well as the marker component can contain water-soluble polymers, in one embodiment such a polymer can serve as a linker as well as a core component. In this case, one part of such a polymer can be considered as a linker, another part as core component.

In a preferred embodiment of the invention, linear polymers or polymers containing few branches are used as core components, for instance, polyamides (e.g., polypeptides), poly-acrylic acid, polysaccharides, dextran, poly(acrylamides), polyvinyl alcohols. The polymer can consist of identical or different monomers. Especially in this embodiment, the linker component can have less than 50 chain atoms. Thus, linker lengths of approx. 5 to 10, 10 to 20 or 20 to 50 chain atoms can be sufficient to preserve the substrate properties of the nuc-macromolecules for enzymes. Such a core component of the marker fulfils the function of the linker component: it creates spatial distance between sterically demanding marker units and active centers of the respective enzymes.

The water-soluble polymers preferably have an average chain length of 20 to 1,000,000 chain atoms. For instance, an average chain length will be between 20 and 100, 100 and 500, 500 and 5000, 5000 and 100000, 100000 and 1000000 chain atoms.

In one embodiment, the polymer generally has a neutral form when dissolved in watery phase with a pH between 4 and 10 (e.g., dextran or polyacrylamide). In another embodiment, the polymer is charged if dissolved in a watery phase with a pH between 4 and 10. It can carry positive (e.g., polylysine) or negative charges (e.g., polyacrylic acid).

The coupling of marker units to a water-soluble polymer depends on the kind of the polymer. The reactive groups necessary for the coupling can already be present in the polymer (e.g., polylysine or polyacrylic acid) or can be introduced into the polymer in a separate step. For instance, many different variants for introducing reactive groups and chemical couplings are known for dextran. (Molteni L. Methods in Enzymology 1985, v. 112, 285, Rogovin A. Z. et al. J. Macromol Sci. 1972, A6, 569, Axen R. et al. Nature 1967, v. 214, 1302, Bethell G. S. et al. J. Biol. Chem. 1979, v. 254, 2572, Lahm O. et al. Carbohydrate Res. 1977, v. 58, 249, WO 93/01498, WO 98/22620, WO 00/07019).

The core component has in a favored application several coupling positions to which further elements can be bound, e.g. structural marker units or nuc-linker-components.

For instance, polylysine molecules have multiple free amino groups to which several dye molecules, biotin molecules, hapten molecules or nucleic acid chains can be coupled. Polylysines of different molecular mass are commercially available (e.g. 1000-2000 Da, 2000-10000 Da, 10000-50000 Da).

Nucleic acid strands constitute a further example of the core component and these chains have the following length ranges (number of nucleotide monomeres in a chain): 10 to 20, to 50, 50 to 100, 100 to 200, 200 to 500, 500 to 1000, 1000 to 5000, 5000 to 10000. These nucleic acids act as a binding partner for sequence complementary marker-units (FIG. 7b).

In a further embodiment, the core component consists of a dendrimer, e.g. polypropyleneimine or polyaminoamine. Examples of other dendrimers are known: Cientifica "Dendrimers", in 2003, Technology white papers No. 6, Klajnert et al. Acta Biochimica Polonica, 2001, v. 48; p 199-, Manduchi et al. Physiol. Genomics 2002, v. 10; p 169-, Sharma et al. Electrophoresis. 2003, v. 24; p 2733-, Morgan et al. Curr Opin drug Discov Devel. 2002; v. 5 (6); p 966-73, Benters et al. Nucleic Acids Res. 2002, v. 30 (2): pE10, Nils et al. J Theor Biol. 1997; v. 187 (2): p 273-84. Many dendrimers are commercially available (Genisphere, www.genisphere.com, Chimera Biotech GmbH).

Further combinations for the core component from the constituents described above are obvious to the specialist.

1.3.3.3.3.2 Coupling of the Marker Units

Marker units can be bound to the core component or to the linker component by a covalent bond, for example, via a crosslinker (Chemistry of protein conjugation and cross linking, S. Wang, 1993, ISBN 0-8493-5886-8, "Bioconjugation: protein coupling techniques for the biomedical sciences", M. Aslam, 1996, ISBN 0-333-58375-2), or via an affine bond, for example, biotin-streptavidin connection or hybridizing of nucleic acid chains or antigen-antibody interaction ("Bioconjugation: protein coupling techniques for the biomedical sciences", M. Aslam, in 1996, ISBN 0-333-58375-2).

In one embodiment, the coupling of the marker units to the core component is conducted already during the synthesis of the nuc-macromolecules.

In another embodiment, the chemically synthesized nuc-macromolecules comprise a marker component consisting only of a core component without marker units. The coupling of marker units to the core component is conducted after the nuc-macromolecules have been incorporated in the nucleic acid chain. Due to the large number of potential binding positions within the core component, the probability of the coupling of the marker units to the core component of incorporated nucleotides is therefore substantially larger in comparison to conventional nucleotide structures. The coupling chemistry depends in detail on the structure of the marker units and the structure of the core component.

Covalent coupling: In one embodiment, the connection between the marker units and the core component can be resistant (example 33), e.g. to temperatures up to 100° C., to pH ranges between 3 and 12, and/or resistant to hydrolytical enzymes (e.g., esterases). In another embodiment of the invention, the connection is cleavable under mild conditions.

Examples of the coupling of nucleic acids to dendrimers (this corresponds to a coupling of marker units to the core component) are described, e.g., in Shchepinov et al. Nucleic Acids Res. 1999; v. 27 (15):p 3035-41, Goh et al. Chem Commun (Camb). 2002; (24): p 2954.

1.3.3.3.3.3 Coupling Between Linker and Marker

The connection between the linker component and the marker depends on the respective structures of the marker units or the structure of the core component. In one embodiment, the linker component is bound directly to the signal-giving or signal-transmitting marker unit (FIG. 4a). The marker can consist of only one or several marker units.

In a further embodiment, one or several linker components are bound to the core component of the marker (FIG. 5d).

The connection between the linker component and the marker can be covalent as well as affine. Many examples are known to the specialist, e.g. "Bioconjugation: protein coupling techniques for the biomedical sciences", M. Aslam, in 1996, ISBN 0-333-58375-2. "Chemistry of protein conjugation and crosslinking" Shan S. Wong in 1993 CRC Press Inc).

Covalent coupling: In one embodiment, the connection between the linker component and the marker can be resistant to, e.g., temperatures up to 130° C., pH ranges between 1 and 14, and/or resistant to hydrolytic enzymes (e.g. proteases, esterases). In another embodiment, the connection is cleavable under mild conditions.

According to some embodiments of this invention, macromolecular compounds used for the labeling of nucleotides comprise water-soluble polymers (see above). The linker of the nuc-macromolecules comprises water-soluble polymers too. A person skilled in the art should recognize that assignment of individual polymers to the linker or to the marker has a descriptive character.

1.3.3.3.3.4 Ratio of Nuc-Components in a Nuc-Macromolecule

One nuc-macromolecule can comprise on average 1 to 2, 2 to 5, 5 to 10, 10 to 30, 30 to 100, 100 to 1000 nuc-components.

In one embodiment, all nuc-macromolecules have the same number of nuc-components per one nuc-macromolecule. For instance, a maximum of 4 biotin molecules can be bound per one streptavidin molecule; at a saturating concentration of nuc-linker components, a uniform population of nuc-macromolecules can be obtained.

In another embodiment, a nuc-macromolecule population has a defined average number of nuc-components per one nuc-macromolecule, however, In the population itself there is dispersion in the actual occupation of the nuc-macromolecules by nuc-components. In this case, the number of nuc-components per one nuc-macromolecule displays an average.

1.3.3.3.3.5 Ratio of Marker Units in a Nuc-Macromolecule

The number of marker units in one nuc-macromolecule falls within the following ranges: 1 and 2, 2 and 5, 5 and 20, 20 and 50, 50 and 100, 100 and 500, 500 and 1000, 1000 and 10000, 10000 and 100000. In one embodiment, nuc-macromolecules have a definite number of signal-giving units per one marker. In another embodiment, a population of nuc-macromolecules has a varying number of marker units per one nuc-macromolecule and it does not need to have a definite value for every single nuc-macromolecule in a population.

In one embodiment, all the nuc-macromolecules have the same number of marker units per one nuc-macromolecule. For instance, a maximum of 4 biotin molecules can be bound per one streptavidin molecule, see "Avidin-Biotin-Technology", Methods in Enzymology v. 184, 1990.

In another embodiment, a nuc-macromolecule population has a defined average number of marker units per one nuc-macromolecule, however, in the population itself, there is dispersion in the actual occupation of the nuc-macromolecules by marker units. An increasingly more uniform occupation of the nuc-macromolecules by marker units can be achieved by the use of saturating concentration during the synthesis of the marker component.

For instance, in cases where only qualitative detection is important, the exact number of marker units per one nuc-macromolecule has a subordinate role. In such cases the availability of a stable signal is important in itself.

To an expert in the field it should be evident that the said marker components have substantially greater molecule size and molecule measures, than the respective nuc-components themselves. Other examples of macromolecular marker components should readily suggest themselves to an expert in the field.

1.3.3.3.3.6 Substrate Properties of the Nuc-Macromolecules

The nuc-component bound to a nuc-macromolecule can serve as a substrate for different enzymes. For instance, a nucleoside triphosphate as the nuc-component serves as a substrate for a polymerase, so that the nuc-component can be incorporated in a growing strand by a polymerase and therefore the whole nuc-macromolecule is coupled covalently to the strand.

Further examples of enzymes are kinases, phosphorylases and transferases.

As the monomer part of a nucleic acid chain, nuc-macromolecules can likewise serve as substrates for enzymes, for instance, for 3'- or 5'-exonucleases or endonucleases ("Molecular cloning" in 1989, Ed. Maniatis, Cold Spring Harbor Laboratory) or for the other suitable partial activities of polymerases, as for example described for real time PCR (S. Meuer "Rapid cycle real time PCR", Springer 2004, ISBN 3-540-66736-9, T. Weissensteiner "PCR-Technology: current innovations" CRC Press 2004 ISBN 0-8493-1184-5).

The substrate properties of the nuc-component(s) determine the substrate properties of the nuc-macromolecules. Thus, the nuc-component can serve as a terminator, so that only one single nuc-macromolecule can be incorporated. In another embodiment, the nuc-component serves as a reversible terminator, which allows for an extension reaction controlled step-by-step, as described, for example, in Ju et al. the U.S. Pat. No. 6,664,079, Tcherkassov WO 02088382.

As the monomer part of a nucleic acid chain, nuc-components can determine its enzymatic properties, such as exonuclease activity. In another embodiment, not only the nuc-components of the nuc-macromolecules, but also the neighboring nucleotides, determine the enzymatic properties, e.g. in the case of endonucleases.

1.3.3.3.7 Function of the Markers

In one embodiment, the macromolecular marker component can have a signal-giving function. In another embodiment, it has a signal-transmitting function. In a further embodiment, it has a catalytic function. In a still further embodiment, it has an affine function. In a still further embodiment, the marker combines more than just one function, e.g. signal-giving as well as signal-transmitting function. Further combinations will be obvious.

In the case of signal-giving function, the marker component contains constituents coupled already during the chemical synthesis to nuc-macromolecules (see example 33).

In the case of signal-transmitting function, the marker component contains constituents that allow for reaction with signal-giving molecules, so that they can develop their signaling properties after this reaction (see example 32). For instance, a marker component consists of several biotin molecules, e.g. 100 Biotin molecules. After the incorporation of the nuc-macromolecules, a detection reaction can take place with modified streptavidin molecules. In another example, nucleic acid chains display the signal-transmitting function: after the incorporation of nuc-macromolecules, a hybridisation of uniform oligonucleotides with detectable units, e.g. fluorescent dyes (synthesized by MWG-Biotech), to the marker component can take place. In a further example, amino or mercapto groups have the signal-transmitting function, e.g. 50 amino groups per marker. After the incorporation of the nuc-macromolecules in the nucleic acid chain, a chemical modification with reactive components is conducted, e.g. with dyes, as described, for example, for incorporated allyl-amino-dUTP, Diehl et al. Nucleic Acid Research, in 2002, v. 30, No. 16 e79.

In another embodiment, the macromolecular marker component has a catalytic function (in the form of an enzyme or ribozyme). Different enzymes can be used, e.g. peroxidases or alkaline phosphatases. Due to the coupling of the particular enzyme to the nuc-component, after the incorporation of nuc-macromolecules to the nucleic acid strand, this enzyme is bonded covalently to the strand, also.

In a further embodiment, a macromolecular marker component has an affinity functionality to another molecule. Examples of such markers are streptavidin molecules, antibodies or nucleic acid chains (see example 30 or 32).

1.3.4 Low Molecular Marker

The state-of-the-art labeling of nucleotides, for instance, with one or two biotin molecules, one or two dye molecules, one or two hapten molecules (e.g., digoxigenin).

1.3.5 Conventionally modified nucleotide a nucleotide with a linker (average length between 5 and 30 atoms) and a marker. A conventionally modified nucleotide usually carries a marker with low molecular weight, e.g. one dye molecule or one biotin molecule.

1.3.6 Enzymes (Polymerases)

In one embodiment, the nuc-macromolecules can be used as substrates for enzymes. Polymerases represent frequently used enzymes, which utilize nucleotides as substrates. They will be dealt with further as representative examples of other nucleotide-utilizing enzymes. One of the central abilities of polymerases consists in covalent coupling of nucleotide monomers to a polymer. Furthermore, the synthesis can be template-dependent (as for example DNA or RNA synthesis with DNA- or RNA-dependent polymerases) as well as independent of templates, e.g. terminal transferases (J Sambrook "Molecular Cloning" 3. Ed. CSHL Press in 2001).

If RNA is used as a substrate (e.g., mRNA) in the sequencing reaction, commercially available RNA-dependent DNA polymerases can be used, e.g. AMV reverse transcriptase (Sigma), M-MLV reverse transcriptase (Sigma), HIV reverse transcriptase without RNAse activity. For certain applications, reverse transcriptases can be essentially free of RNAse activity ("Molecular cloning" in 1989, Ed. Maniatis, Cold Spring Harbor Laboratory), e.g. for use in mRNA labeling for hybridisation applications.

If DNA is used as a substrate (e.g. cDNA), all the following polymerases are suitable in principle: DNA-dependent DNA polymerases with or without 3'-5' exonuclease activity ("DNA-Replication" in 1992 Ed. A. Kornberg, Freeman and company NY), e.g. modified T7-Polymerase of the type "Sequenase version 2" (Amersham Pharmacia Biotech), Klenow fragment of the DNA-Polymerase I with or without 3'-5'exonuclease activity (Amersham Pharmacia Biotech), polymerase Beta of different origin ("Animal Cell DNA polymerases" in 1983, Fry M., CRC Press Inc, commercially available from Chimerx), thermostable polymerases such as, for example, Taq Polymerase (GibcoBRL), proHA-DNA-Polymerase (Eurogentec), Vent, Vent exo-minus, Pfu, Thermosequenase, Pwo-Polymerase etc. (Promega).

DNA-dependent RNA polymerases can also be used, e.g. E. coli RNA polymerase, T7 RNA polymerase, SP6 RNA polymerase.

Polymerases with 3'- or 5'-exonuclease activity can be used in certain applications (e.g. with real-time PCR).

In the following description, DNA-dependent DNA polymerases will be considered as examples of polymerases.

1.3.7 Cleavable Compound

A compound which is cleavable under mild conditions. This compound can represent a part in the linker and can be cleavable in one or several positions. It can be a chemically cleavable bond, such as, for example, disulfide, acetal, thioester bonds (Short WO 9949082, Tcherkassov WO 02088382). It can also be a photo-chemically cleavable compound (Rothschild WO 9531429). It can also be an enzymatically cleavable compound (for instance, a peptide or polypeptide bond, Odedra WO 0192284), cleavable by peptidases, a poly- or oligo-saccharide bond, cleavable by disaccharidases, whereas the cleavage can be achieved by a specific enzyme between certain monomers of the cleavable bonds.

Several examples of cleavable compounds are known. The synthesis of such a compound is described, for Instance, in (Tcherkassov WO 02088382, Metzker et al. Nucleic Acid Research 1994, v. 22, p. 4259-, Canard et al. Genes, 1994, v. 148, p. 1, Kwiatkowski U.S. Pat. No. 6,255,475, Kwiatkowski WO 0125247, Parce WO 0050642). A cleavable compound can be a part of the linker or can form the connecting part of the linker to the nucleotide, or the connecting part of the linker component to the marker component, or the connection between marker units and the core component.

1.3.8 DNA

Deoxyribonucleic acid of different origin and different length (e.g. oligonucleotides, polynucleotides, plasmides, genomic DNA, cDNA, ssDNA, dsDNA)

1.3.9 RNA

Ribonucleic acid

1.3.10 dNTP

2'-deoxynucleoside triphosphate, as a substrate for DNA polymerases and reverse-transcriptases, e.g. dATP, dGTP, dUTP, dTTP, dCTP.

1.3.11 NTP

Ribonucleoside triphosphate, as a substrate for RNA polymerases, UTP, CTP, ATP, GTP.

1.3.12 NT

Abbreviation "NT" is used for the description of the length of a particular nucleic acid sequence, e.g. 1000 NT. In this case "NT" means nucleoside monophosphates.

The plural is formed by the addition of the suffix "-s"; "NT" means, for example, "one nucleotide", "NTs" means "several nucleotides".

1.3.13 NAC

Nucleic acid chain (NSK abbreviation stands for German "Nukleinsäurekette"), DNA or RNA.

1.3.14 Term "the Whole Sequence"

The whole sequence is the sum of all the sequences in one experiment; it can comprise originally one or several NACs. Also, the whole sequence can display parts or equivalents of another sequence or sequence populations (e.g., mRNA, cDNA, Plasmid DNA with insert, BAC, YAC) and can originate from one species or various species.

1.3.15 NACF

The nucleic acid chains fragment (NSKF abbreviation stands for German "Nukleinsäurekettenfragment") (DNA or RNA) which corresponds to a part of the whole sequence, NACFs—the plural form—nucleic acid chain fragments. The sum of the NACFs forms an equivalent to the whole sequence. The NACFs can be, for instance, fragments of the whole sequence (DNA or RNA), which result after a fragmentation step.

1.3.16 Primer Binding Site (PBS)

A PBS is the part of the sequence in the NAC or NACF to which the primer binds.

1.3.17 Reference Sequence

A reference sequence is an already known sequence, divergences from which in the analysed sequence or sequences (e.g. whole sequence) have to be determined. Reference sequences can be found in databases, such as, for example, the NCBI database.

1.3.18 Tm

Melting temperature 1.3.19 Steric Hindrance, Sterically Demanding Group or Ligand A sterically demanding group or ligand which (by its chemical structure) changes the properties of the nucleotides coupled with this group in such a way that these nucleotides cannot be inserted successively by a polymerase in an extension reaction. One or several sterically demanding groups coupled to the nucleotide base can lead to the stop or to the impedance of further synthesis. Many of the markers, currently used in research, represents a sterical hindrance for the enzymes. Biotin, digoxigenin and fluorescent dyes like fluorescein, tetramethylrhodamine, Cy3-dye, are examples of such sterically demanding groups (Zhu et al. Cytometry in 1997, v. 28, p. 206, Zhu et al. NAR 1994, v. 22, p. 3418, Gebeyehu et al., NAR 1987, v. 15, p. 4513, Wiemann et al. Analytical Biochemistry in 1996, v. 234, p. 166, Heer et al. BioTechniques 1994 v. 16 p. 54). Further examples for sterically demanding groups can be linear or branched polymers with a compact three-dimensional structure, as for example proteins or dendrimers.

1.3.20 PNA

Peptide Nucleic Acid

2. Detailed Description

The invention describes a new class of modified nucleotides.

1. One aspect of the invention relates to macromolecular compounds with the structure:

(nuc-linker)$_n$-marker wherein:

Nuc is a nucleotide or nucleoside (nuc-component)

Linker is a linker component, which connects one nuc component and one macromolecular marker component.

Marker is a macromolecular marker component (n) is a positive integer from 1 to 1000

2. A further aspect of the invention relates to macromolecular compounds according to aspect 1, wherein the nuc-component comprises the following structures (FIG. 3A), wherein:

Base is selected independently from the group of adenine, or 7-deazaadenine, or guanine, or 7-deazaguanine, or thymine, or cytosine, or uracil, or their modifications, wherein (L) is the linkage between the nuc-component and the linker component (coupling unit L) and X is the coupling position of the coupling unit (L) to the base.

$R_1$—is H $R_2$—is selected independently from the group of H, OH, halogen, $NH_2$, SH or protected OH group $R_3$—is selected independently from the group of H, OH, halogen, $PO_3$, SH, $N_3$, $NH_2$, O—$R_{3-1}$, $P(O)_m$—$R_{3-1}$ ((m) is 1 or 2), NH—$R_{3-1}$, Si—$R_{3-1}$ wherein $R_{3-1}$ is a chemically, photochemically or enzymatically cleavable group or comprises one of the following modifications: —CO—Y, —$CH_2$—O—Y, —$CH_2$—S—Y, —$CH_2$—$N_3$—CO—O—Y, —CO—S—Y, —CO—NH—Y, —$CH_2$—CH=$CH_2$, wherein Y is an alkyl, for instance $(CH_2)_n$—$CH_3$ wherein n is a number between 0 and 4, or a substituted alkyl, for instance with halogen, hydroxy group, amino group, carboxy group.

$R_4$—is H or OH $R_5$—is selected independently from the group of OH, or a protected OH group, or a monophosphate group, or a diphosphate group, or a triphosphate group, or is an alpha thiotriphosphate group.

3. A further aspect of the invention relates to macromolecular compounds according to aspect 1, wherein the nuc-component comprises the following structures (FIG. 3B), Wherein:

Base is selected independently from the group of adenine, or 7-deazaadenine, or guanine, or 7-deazaguanine, or thymine, or cytosine, or uracil, or their modifications capable of enzymatic reactions.

$R_1$—is H $R_2$—is selected independently from the group of H, OH, halogen, $NH_2$, SH or protected OH group $R_3$—is selected independently from the group of O—$R_{3-2}$-L, $P(O)_m$—$R_{3-2}$-L and (m) is 1 or 2, NH—$R_{3-2}$-L, S—$R_{3-2}$-L, Si—$R_{3-2}$-L, wherein $R_{3-2}$ is the coupling position of the linker to the nucleotide and L is the coupling unit (L) of the linker.

$R_4$—is H or OH $R_5$—is selected independently from the group of OH, or a protected OH group, or a monophosphate group, or a diphosphate group, or a triphosphate group, or is an alpha-thiotriphosphate group.

4. A further aspect of the invention relates to macromolecular compounds according to aspect 1, wherein the nuc-component comprises the following structures (FIG. 3B), Wherein:

Base is selected independently from the group of adenine, or 7-deazaadenine, or guanine, or 7-deazaguanine, or thymine, or cytosine, or uracil, or their modifications capable of enzymatic reactions.

$R_1$—is H $R_2$—is selected independently from the group of H, OH, halogen, $NH_2$, SH or protected OH group $R_3$—is selected independently from the group of H, OH, halogen, $PO_3$, SH, $NH_2$, O—$R_{3-1}$, $P(O)_m$—$R_{3-1}$ ((m) is 1 or 2), NH—$R_{3-1}$, S—$R_{3-1}$, Si—$R_{3-1}$ wherein $R_{3-1}$ is a chemically, photochemically or enzymatically cleavable group.

$R_4$—is H or OH $R_5$—is selected independently from the group of O—$R_{5-1}$-L, or P—(O)$_3$—$R_{5-1}$-L (modified monophosphate group), or P—(O)$_3$—P—(O)$_3$—$R_{5-1}$-L (modified diphosphate group) or P—(O)$_3$—P—(O)$_3$—P—(O)$_3$—$R_{5-1}$-L (modified triphosphate group), wherein $R_{5-1}$ is the coupling position of the coupling unit (L) to the nucleotide and coupling unit (L) is a linkage between nuc-component and the rest of the linker.

5. A further aspect of the invention relates to macromolecular compounds according to aspects 1 to 4, wherein the coupling unit (L) of the linker comprises the following structural elements:
$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—$R_7$,
$R_6$—(CH$_2$)$_n$—$R_7$, $R_6$-A-(CH$_2$)$_n$—$R_7$, $R_6$—(CH$_2$)$_n$—B—$R_7$,
$R_6$—(CH=CH—)$_n$—$R_7$, $R_6$-(A-CH=CH—)$_n$—$R_7$, $R_6$—(CH=CH—B—)$_n$—$R_7$, $R_6$—(CH=CH—CH$_2$—B—)$_n$—$R_7$,
$R_7$, $R_6$-A-CH=CH—(CH$_2$—)$_n$—$R_7$, $R_6$—(—CH=CH—CH$_2$)$_n$—B—$R_7$,
$R_6$—(C≡C—)$_n$—$R_7$, $R_6$-(A-C≡C—)$_n$—$R_7$, $R_6$-(A-C≡C—CH$_2$)$_n$—$R_7$, $R_6$—(C≡C—B—)$_n$—$R_7$,
$R_6$—(C≡C—CH$_2$—B—)$_n$—$R_7$, $R_6$-A-C≡C—(CH$_2$—)$_n$—$R_7$, $R_6$—(—C≡C—CH$_2$)$_n$—B—$R_7$,
$R_6$—(—C≡C—CH$_2$—CH$_2$)$_n$—B—$R_7$
wherein $R_6$ is the nuc-component, $R_7$ is the rest of the linker, and A and B comprise independently the following structural elements: —NH—, —O—, —S—, —SS—, —CO—NH—, —NH—CO—, —CO—O—, —O—CO—, —CO—S—, —S—CO—, —P(O)$_2$—, —Si—, —(CH$_2$)$_n$—, wherein (n) ranges from 1 to 5, a photolabile group 6. A further aspect of the invention relates to macromolecular compounds according to aspects 1 to 5, wherein the linker-component comprises a water-soluble polymer.

7. A further aspect of the invention relates to macromolecular compounds according to aspect 6, wherein the linker-component comprises water-soluble polymers selected independently from the following group: polyethylene glycol (PEG), polysaccharides, dextran, polyamides, polypeptides, polyphosphates, polyacetates, polyalkyleneglycoles, copolymers from ethyleneglycol and propyleneglycol, polyolefinic alcohols, polyvinylpyrrolidones, poly(hydroxyalkylmethacrylamides), polyhydroxyalkylmethacrylates, poly(x-hydroxy) acids, polyacrylic acid, polyacrylamide, polyvinylalcohol.

8. A further aspect of the invention relates to macromolecular compounds according to aspects 1 to 7, wherein the average length of a linker component ranges between 2 to 5, 5 to 10, 10 to 20, 20 to 50, 50 to 100, 100 to 200, 200 to 500, 500 to 1000, 1000 to 2000, 2000 to 10000, 10000 to 100000, 100000 to 500000 atoms (chain atoms).

9. A further aspect of the invention relates to macromolecular compounds according to aspects 1 to 8, wherein a marker component has one of the following functions: signal-giving function, signal-transmitting function, catalytic function or affine function.

10. A further aspect of the invention relates to macromolecular compounds according to aspects 1 to 9, wherein a marker component consists of one structural marker unit.

11. A further aspect of the invention relates to macromolecular compounds according to aspects 1 to 9, wherein a marker component consists of several structural marker units bonded to a core component.

12. A further aspect of the invention relates to macromolecular compounds according to aspects 10 or 11, wherein a structural marker unit independently comprises one of the following structural elements: biotin, hapten, radioactive isotope, rare-earth atom, dye, fluorescent dye.

13. A further aspect of the invention relates to macromolecular compounds according to aspects 10 or 11, wherein a structural marker unit independently comprises one of the following elements: nanocrystals or their modifications, proteins or their modifications, nucleic acids or their modifications, particles or their modifications.

14. A further aspect of the invention relates to macromolecular compounds according to aspect 13, wherein a structural marker unit comprises one of the following proteins:
enzymes or their conjugates or modifications,
antibodies or their conjugates or modifications,
streptavidin or its conjugates or modifications,
avidin or its conjugates or modifications 15. A further aspect of the invention relates to macromolecular compounds according to aspect 13, wherein a structural marker unit comprises one of the following types of nucleic acid chains: DNA, RNA, PNA, wherein the length of nucleic acid chains ranges between 10 and 10,000 nucleotides or their equivalents.

16. A further aspect of the invention relates to macromolecular compounds according to aspects 11 to 15, wherein the core component of the marker component independently comprises one of the following elements: water-soluble polymer from the group of: polyamides (e.g. polypeptides), polyacrylic acid and its derivates, polyacrylamides and their derivates, polyvinylalcohols and their derivates, polysaccharide, dextran and its derivates, nucleic acids and their derivates, streptavidin or avidin and their derivates, dendrimeres, whereas these elements can be linear or branched or crosslinked with each other.

17. A further aspect of the invention relates to macromolecular compounds according to aspects 1 to 9, 11 to 16, wherein the linkage between several structural marker units and the core component is covalent or affine.

18. A further aspect of the invention relates to macromolecular compounds according to aspects 1 to 10, wherein the linkage between the said structural marker units and the linker is covalent or affine.

19. A further aspect of the invention relates to macromolecular compounds according to aspects 1 to 9, 11 to 17, wherein the linkage between the core component and the linker is covalent or affine.

20. A further aspect of the invention relates to macromolecular compounds according to aspects 1 to 19, wherein only one nuc-component with one linker component is linked to the marker component, wherein the linker length ranges between 2 to 5, 5 to 10, 10 to 20, 20 to 50, 50 to 100, 100 to 200, 200 to 500, 500 to 1000, 1000 to 2000, 2000 to 5000, 5000 to 20000, 20000 to 100000 atoms.
21. A further aspect of the invention relates to macromolecular compounds according to aspects 1 to 20, wherein only one nuc-component with one linker component is linked to the marker component, wherein the linker length ranges between 2 to 5, 5 to 10, 10 to 20, 20 to 50, 50 to 100, 100 to 200, 200 to 500, 500 to 1000, 1000 to 2000, 2000 to 5000, 5000 to 20000, 20000 to 100000 atoms and the linker component comprises one or several compounds that are cleavable under mild conditions.
22. A further aspect of the Invention relates to macromolecular compounds according to aspects 1 to 21, wherein only one nuc-component with one linker component is linked to the marker component, wherein the linker length ranges between 2 to 5, 5 to 10, 10 to 20, 20 to 50, 50 to 100, 100 to 200, 200 to 500, 500 to 1000, 1000 to 2000, 2000 to 5000, 5000 to 20000, 20000 to 100000 atoms and one or several parts of the nuc-macromolecule are modified in such a way, that only one nuc-component can be incorporated into the growing strand.
23. A further aspect of the invention relates to macromolecular compounds according to aspects 1 to 19, wherein several nuc-components are each coupled to one marker component via a particular linker, wherein the length of each respective linker component ranges between 2 to 5, 5 to 10, 10 to 20, 20 to 50, 50 to 100, 100 to 200, 200 to 500, 500 to 1000, 1000 to 2000, 2000 to 5000, 5000 to 20000, 20000 to 100000 atoms.
24. A further aspect of the invention relates to macromolecular compounds according to aspects 1 to 19, 23, wherein several nuc-components are each coupled to one marker component via a particular linker, wherein the length of each respective linker component ranges between 2 to 5, 5 to 10, 10 to 20, 20 to 50, 50 to 100, 100 to 200, 200 to 500, 500 to 1000, 1000 to 2000, 2000 to 5000, 5000 to 20000, 20000 to 100000 atoms and each respective linker component comprises one or several compounds that are cleavable under mild conditions.
25. A further aspect of the invention relates to macromolecular compounds according to aspects 1 to 19, 23, 24, wherein several nuc-components are each coupled to one marker component via a particular linker, wherein the length of each respective linker component ranges between 2 to 5, 5 to 10, 10 to 20, 20 to 50, 50 to 100, 100 to 200, 200 to 500, 500 to 1000, 1000 to 2000, 2000 to 5000, 5000 to 20000, 20000 to 100000 atoms, and one or several parts of the nuc-macromolecule are modified in such a way that only one nuc-component can be incorporated into the growing nucleic acid chain.
26. A further aspect of the invention relates to oligonucleotides or polynucleotides comprising at least one nuc-macromolecule according to aspects 1 to 25 per one nucleic acid chain.
27. A further aspect of the invention relates to oligonucleotides or polynucleotides according to aspect 26, wherein oligo- or polynucleotides are RNA or DNA or PNA and their length ranges between 5 and 50,000 nucleotides.
28. A further aspect of the invention relates to a method for modifying of nucleic acid chains, wherein nuc-macromolecules according to aspects 1 to 25 are used for the coupling.
29. A further aspect of the invention relates to a method according to aspect 28, wherein the modification is accomplished by an enzymatic coupling and the reaction mixture comprises the following components:
at least one type of nuc-macromolecules or their intermediate stages according to the aspects 1 to 25, wherein every type of nuc-macromolecule is distinctively labeled,
at least one population of the nucleic acid chains,
at least one type of enzyme for coupling nuc-macromolecules to the nucleic acid chains,
30. A further aspect of the invention relates to a method according to aspect 28, wherein the modification is accomplished by an enzymatic coupling and the reaction mixture comprises the following components:
at least one type of nuc-macromolecules or their intermediate stages according to the aspects 1 to 25, wherein every type of nuc-macromolecule is distinctively labeled,
at least one population of the nucleic acid chains,
at least one type of enzyme for coupling nuc-macromolecules to the nucleic acid chains,
at least one other type of nucleoside triphosphates.
31. A further aspect of the invention relates to a method according to aspects 29, 30, wherein the said type of enzyme independently comprises one of the following groups: DNA-polymerases, RNA-polymerases, terminal transferases.
32. A further aspect of the invention relates to a method according to aspect 30, wherein the "other type" of nucleoside tri-phosphates is independently selected from the group of ribonucleoside tri-phosphates (ATP, GTP, UTP, CTP), of 2'-deoxyribonucleoside triphosphates (dATP, dUTP, dTTP, dCTP, dGTP), of 2',3'-dideoxynucleoside triphosphates (ddATP, ddGTP, ddUTP, ddCTP, ddTTP).
33. A further aspect of the Invention relates to a method according to aspect 32, wherein the "other type" of nucleoside tri-phosphates is conventionally modified nucleotides with a label, wherein the said label is independently selected from the group of fluorescent dye, biotin, hapten or radioactive element.
34. A further aspect of the invention relates to a method according to aspects 28 to 33, wherein at least two different populations of nucleic acid chains are present
35. A further aspect of the invention relates to a method according to aspect 34, wherein at least one of the populations of the nucleic acid chains has a primer function and at least one population of the nucleic acid chains has a template function.
36. A further aspect of the invention relates to a method according to aspect 28, wherein the modification is accomplished by chemical coupling and the coupling of the nuc-macromolecules to the nucleic acid chain is accomplished via phosphoroamidite-coupling.
37. A further aspect of the invention relates to a method according to aspects 28 to 36, wherein nuc-macromolecules which allow for the coupling of only single nuc-component into the growing nucleic acid strand are used for the labeling process and multiple incorporations are prevented by modifications of the nuc-component and/or the linker component and/or the marker component.
38. A further aspect of the invention relates to a method according to aspect 37, wherein the multiple coupling is prevented reversibly.

39. A further aspect of the invention relates to a method according to aspect 37, wherein the multiple coupling is prevented irreversibly.
40. A further aspect of the invention relates to a method according to aspects 28 to 36, wherein nuc-macromolecules which allow for the coupling of multiple nuc-components into the growing nucleic acid strand are used for the labeling process.
41. A further aspect of the invention relates to a method according to aspects 28 to 40, wherein the nucleic acid chains participating in the reaction are coupled to a solid phase and have addressable positions.
42. A further aspect of the invention relates to a method according to aspect 41, wherein the nucleic acid chains compose a uniform population.
43. A further aspect of the invention relates to a method according to aspect 41, wherein the nucleic acid chains compose two or more different populations and each of the populations has an addressable position on the solid phase.
44. A further aspect of the invention relates to a method according to aspects 41, 42, wherein the coupling of nuc-macromolecules is conducted on the uniform population of nucleic acid molecules attached to the solid phase and the marker component of the nuc-macromolecule remains on the extended nucleic acid strand after the coupling and is not cleaved off.
45. A further aspect of the invention relates to a method according to aspects 41, 42, wherein the coupling of the nuc-macromolecules is conducted on the uniform population of nucleic acid chains attached to the solid phase and the marker component or its individual parts are cleaved off, with or without the linker component of the nuc-macromolecule, from the nuc-component incorporated into the growing nucleic acid strand, the cleaving-off taking place during or after the coupling.
46. A further aspect of the invention relates to a method according to aspects 41, 43, wherein the coupling of nuc-macromolecules in a reaction mixture is conducted simultaneously on two or more different populations of nucleic acid chains attached to the solid phase, wherein each of these populations has distinct addressable positions on the solid phase, and the marker component of the nuc-macromolecule remains on the extended nucleic acid strand after the coupling and is not cleaved off.
47. A further aspect of the invention relates to a method according to the aspects 41, 43, wherein the coupling of nuc-macromolecules is conducted simultaneously on two or more different populations of nucleic acid chains attached to the solid phase, wherein each of these populations has distinct addressable positions on the solid phase, and the marker component or its individual parts are cleaved off, with or without linker component of the nuc-macromolecule, from the nuc-component, the cleaving-off taking place during or after the coupling.
48. A further aspect of the invention relates to a method according to aspects 41 to 47, wherein the addressable positions having nucleic acid molecules on the solid phase are distributed as spots on a plane surface, and nucleic acid molecules are uniform on each spot.
49. A further aspect of the invention relates to a method according to the aspects 41 to 47, wherein the addressable positions having nucleic acid molecules are fastened on the beads or particles and nucleic acid molecules are uniform for each bead.
50. A further aspect of the invention relates to a method according to aspects 41 to 47, wherein the addressable positions having nucleic acid molecules are distributed in a multivessel array, like a microtiter plate or nanotiter plate or picotiter plate, wherein the nucleic acid molecules are uniform in one vessel of the mutlivessel array.
51. A further aspect of the invention relates to a method according to the aspects 28 to 35 and 37 to 50, which comprises the following steps:
    a) Providing of at least one population of single-stranded nucleic acid chains (NAC),
    b) Hybridizing primers to these nucleic acid chains, whereas extendable NAC primer complexes are formed,
    c) Incubation of at least one type of the nuc-macromolecule according to aspects 1 to 25 together with a type of polymerase according to aspect 31 with provided NAC primer complexes in steps (a) and (b) under conditions which allow for incorporation of complementary nuc-macromolecules, and each kind of the nuc-macromolecule having a distinctive label,
    d) Removal of the unincorporated nuc-macromolecules from the NAC primer complexes,
    e) Detection of the signals from the nuc-macromolecules which are incorporated in the NAC primer complexes,
    f) Removal of the linker component and the marker component from the nuc-macromolecules which are incorporated in the NAC primer complexes,
    g) Wash the NAC primer complexes,
If necessary, repetition of the steps (c) to (g).
52. A further aspect of the invention relates to a method according to the aspects 28-40, wherein the nucleic acid chains are coupled to a solid phase in a random arrangement.
53. A further aspect of the invention relates to a method according to aspects 28 to 41, 52 for the parallel sequence analysis of nucleic acid sequences (nucleic acid chains, NACs), in which
fragments (NACFs) of single-stranded NACs with a length of approximately 50 to 1000 nucleotides that may represent overlapping partial sequences of the whole sequence are produced,
the NACFs are bonded to a reaction surface in a random arrangement using a uniform or several different primers in the form of NACF primer complexes, wherein the density of NACF primer complexes bonded to the surface allows for an optical detection of signals from single incorporated nuc-macromolecules,
a cyclical synthesis reaction of the complementary strand of the NACFs is performed using one or more polymerases by
    a) adding, to the NACF primer complexes bonded to the surface, a solution containing one or more polymerases and one to four nuc-macromolecules that have a marker component labeled with fluorescent dyes, wherein the fluorescent dyes, which each are located on the marker component when at least two nuc-macromolecules are used simultaneously, are chosen in such a manner that the nuc-macromolecules used can be distinguished from one another by measurement of different fluorescent signals, the nuc-macromolecules being structurally modified in such a manner that the polymerase is not capable of incorporating another nuc-macromolecule in the same strand after such a nuc-macromolecule has been incorporated in a growing complementary strand, the linker component and marker component being cleavable, b) incubating the stationary phase obtained in step a) under conditions suitable for extending the complementary strands, the complementary strands each being extended by one nuc-macromolecule, c) washing the stationary phase obtained in step b) under conditions suitable for removing nuc-macromolecules that are not incorporated in a complementary strand, d) detecting the single nuc-macromolecules incorporated in complementary strands by measuring the characteristic signal of the respective fluorescent dye, the relative position of the individual fluorescent signals on the reaction surface being determined at the same time, e) cleaving-off the linker component and marker component of the nuc-components added to the complementary strand in order to produce unlabeled (nucleotides or) NACFs, f) washing the stationary phase obtained in step e) under conditions suitable for the removal of the marker component, repeating steps a) to f), several times if necessary, the relative position of individual NACF primer complexes on the reaction surface and the sequence of these NACFs being determined by specific assignment of the fluorescent signals, which were detected in the respective positions in step d) during successive cycles, to the nuc-macromolecules.

54. A further aspect of the invention relates to a method according to aspect 53, characterized in that steps a) to f) of the cyclical synthesis reaction are repeated several times, only one type of nuc-macromolecule being used in each cycle.

55. A further aspect of the invention relates to a method according to aspect 53 characterized in that steps a) to f) of the cyclical synthesis reaction are repeated several times, two types of differently labeled nuc-macromolecules being used in each cycle.

56. A further aspect of the invention relates to a method according to aspect 53 characterized in that steps a) to f) of the cyclical synthesis reaction are repeated several times, four types of differently labeled nuc-macromolecules being used in each cycle.

57. A further aspect of the invention relates to a method according to aspect 53 characterized in that the NACs are variants of a known reference sequence and steps a) to f) of the cyclical synthesis reaction are repeated several times, two differently labeled types of nuc-macromolecules and two unlabeled nucleotides being used alternately in the cycles and the whole sequences being determined by comparison with the reference sequence.

58. A further aspect of the invention relates to a method according to aspects 53 to 57 characterized in that a primer binding site (PBS) is introduced in each of the NACFs, one PBS being introduced at both complementary single strands in the case of double-stranded NACs and the primer binding sites displaying identical or different sequences for all NACFs.

59. A further aspect of the invention relates to a method according to aspects 53 to 57 characterized in that the NACFs are brought into contact with primers in a solution under conditions suitable for the hybridization of the primers to the primer binding sites (PBSs) of the NACFs, the primers exhibiting identical or different sequences to one another, and the NACF primer complexes formed then being bonded to the reaction surface.

60. A further aspect of the invention relates to a method according to aspects 53 to 57 characterized in that the NACFs are first of all immobilized on the reaction surface and only then brought into contact with primers under conditions suitable for the hybridization of the primers to the primer binding sites (PBSs) of the NACFs, NACF primer complexes being formed, the primers exhibiting identical or different sequences to one another.

61. A further aspect of the Invention relates to a method according to aspects 53 to 60, wherein the incorporation reaction is being performed simultaneously on 10 to 100000 different sequence populations.

62. A further aspect of the invention relates to a method according to aspects 53 to 60, wherein the incorporation reaction is being performed simultaneously on 100000 to 10000000000 different sequence populations.

63. A further aspect of the invention relates to a method according to aspects 28 to 62, wherein sequences of the nucleic acid chains are determined.

64. A further aspect of the invention relates to a method according aspects 28 to 63, wherein the marker component is fluorescently labeled.

65. A further aspect of the invention relates to a method according aspects 41 to 64, wherein the solid phase is independently selected from the following group: silicone, glass, ceramics, plastics, gels or their modifications.

Comparison of the Properties of Conventionally Modified Nucleotides and Nuc-Macromolecules.

Substrate Properties of Conventionally Modified Nucleotides

The influence of different lengths and chemical composition of the linker and different sizes and composition of the low molecular weight markers on the substrate properties of nucleotides (G. Wright et al. Pharmac. Ther. 1990, v. 47, p. 447, Klevan U.S. Pat. No. 4,828,979, Lee. et al. Nucleic Acid Research 1992, v. 20, p. 2471, J. Brandis Nucleic Acid Research, 1999, v. 27, p. 1912) shows that even minor changes in the structure of the nucleotides or linker or marker may lead to big changes in the substrate properties of modified nucleotides.

It can be shown that the coupling of significantly larger molecules (e.g. proteins) to a conventionally modified nucleotide results in the loss of its substrate properties (example 34B).

For this reason, signal-amplifying macromolecules could be coupled into the nucleic acid chain only after the completed enzymatic incorporation of nucleotides, e.g. the binding of labeled streptavidin to biotinylated nucleotides.

A comparable situation can be observed for nucleotide monomers in a nucleic acid chain: only low molecular weight compounds should be coupled to an oligonucleotide near to the 3'—OH-position if this oligonucleotide is intended to be a primer in a subsequent enzymatic reaction. Too large a molecule, e.g. streptavidin, coupled to a nucleotide monomer at the 3'-end or in the vicinity of the 3'-end of an oligonucleotide results in a loss of primer properties. Without committing themselves to any particular theory, the inventors explain this fact as the result of the sterical influence of macromolecules. The spatial relations in the active center of a variety of enzymes are very challenging and the catalytic mechanism of many enzymes comprises complex conformational changes in the enzyme structure itself as well as the substrate structure (nucleotide monomers). In many cases, minor chemical modifications of nucleotide monomers result in a changed enzymatical acceptance of the nucleic acids. For example, an alpha-thiophosphonate modification of the nucleotide monomer results in resistance of the nucleic acid chain to exonuclease activity.

Even though there is widespread use of fluorescent dyes in current diagnostics and science, there is a demand for signal-amplifying technologies for biologically active labeled molecules. At present, secondary enzymatic signal amplification steps are often applied.

Despite the obvious consideration of the multiple labelling of nucleotides in the form of a macromolecular marker component, there is no evidence to suggest the possibility of a successful combination of conventional nucleotide structure and a macromolecular marker where the nucleotide preserves its substrate properties.

The mass of conventionally modified nucleotides is comparable to that of non-modified nucleotides and is relatively low if compared to that of proteins, e.g. streptavidin or polymerases. Increasing the mass of the nucleotide by the introduction of macromolecular compounds can result in a change in the physical and biochemical properties of the nucleotides.

Surprisingly, it was possible to overcome this limitation of current state of the art by separating the space-demanding or sterically demanding parts of the nuc-macromolecules from the enzymatically active nuc-component. This spatial separation can be achieved for example by introducing a linker that is substantially longer than known in the prior art between the nuc-component and the marker component.

Surprisingly, the modified nucleotides here invented maintain their substrate activity despite the massive changes in their properties and can be used by enzymes as substrates. For example, polymerases can incorporate the invented modified nucleotides into the growing strands. Terminal deoxynucleotidyl transferase (TdT) can couple nuc-macromolecules to the 3'-end of a nucleic acid chain (example 34B, 34C and example 35).

It should be obvious to the specialist that the mass of the nuc-macromolecules here Invented is several times larger than that of natural nucleotides and has a great influence on the nuc-component.

Application Fields for Nuc-Macromolecules

The coupling of a macromolecular marker to a substrate for enzymes, i.e. to a nucleotide, opens a broad range of applications for these nuc-macromolecules in different fields of biotechnology, medicine and lifescience.

According to this invention, nuc-macromolecules can be used in procedures where they serve as substrates for enzymes.

In one embodiment of the invention, nuc-macromolecules are used in procedures for the labelling of nucleic acids. The incorporation reaction of nuc-macromolecules proceeds according to general rules of the enzymatic primer-extension reaction of nucleic acids ("Molecular Cloning", J. Sambrook, 3. Ed. 2001).

One big benefit of a macromolecular marker coupled to an incorporated nucleotide is a substantially stronger signal compared to conventionally modified nucleotides.

A further benefit is the large distance between the marker and nucleic acid chain, owing to which only minor interactions between the marker and the nucleic acid chain are expected. For example, this has an influence on the fluorescent properties of the marker: the fluorescence of the marker is not quenched by nucleobases (purines and pyrimidines). If several nuc-macromolecules are incorporated into a single nucleic acid chain, the large distance between nuc-components and markers results in a substantial diminution of interactions between the markers of adjacent nucleotides.

In the case of enzymatic labelling of a nucleic acid chain with a nuc-macromolecule there may be no need for further steps of signal amplification. Many of the known signal amplification steps, e.g. biotin-streptavidin, digoxigenin-antibody I-antibody II, result in only medium yield, e.g. during signal amplification in FISH-analysis. Unsteady and low yields in labelling cause fluctuations and weakness of signals that may lead to false interpretation. The introduction of nuc-macromolecules may reduce or eliminate this weakness in labelling. The use of nuc-macromolecules with stable signal intensities may help to overcome signal fluctuations.

The labelling of nucleic acids can be used in different procedures. Particular conditions for the preparation of nucleic acids and the order of enzymatic and detection steps depend upon the individual procedure to which the labelling is applied.

Taken together, the nuc-macromolecules here invented represent an above average improvement in labelling strategies for nucleic acids.

Modified Nucleic Acid Chains

In one embodiment of the invention, nucleic acid chains comprise nuc-components of the nuc-macromolecules as units of the chain. The nuc-macromolecules are considered as monomers of a polymer chain, i.e. the nucleic acid chain. Such nucleic acid chains with integrated nuc-macromolecules can be used as probes and as a reaction partner in different areas (e.g. Real-Time-PCR, Ligase chain reaction).

In one embodiment, a nuc-macromolecule is integrated to the 5' end of the nucleic acid chain. In one embodiment, a nuc-macromolecule is integrated to the 3' end of the nucleic acid chain. In a further embodiment, a nuc-macromolecule is integrated inside of the nucleic acid chain and the distance to the nearest chain end lies within the following ranges (number of the monomers of the chain up to the next chain end): 1 to 2, 2 to 4, 4 to 8, 8 to 15, 15 to 30, 30 to 100, 100 to 500.

A nuc-macromolecule can comprise several nuc-components. In one embodiment, only one nuc-component of a nuc-macromolecule is integrated into a nucleic acid chain; the other nuc-components are in monomer form. In another embodiment, several nuc-components of a nuc-macromolecule are integrated in nucleic acid chains, whereby these nucleic acid chains can have identical or also different sequences.

The use of nucleic acid chains modified with nuc-macromolecules is especially advantageous if the nuc-macromolecule participates as part of a polymer chain in an enzymatic reaction or is in the immediate proximity of the nucleotide participating in the reaction. The influence of a macromolecular marker component on the enzyme is greatly reduced by the long linker of the nuc-macromolecules, so that the modified nucleotide components can take part in the enzymatic reactions (e.g. having primer function in a templatedependent, polymerase driven reaction, with a ligase-dependent reaction (e.g. ligase chain reaction), 3'-exonuclease or 5' exonuclease activities of different enzymes, endonuclease cleavage), i.e. they do not impair the reaction with neighboring nucleotides (J. Wilhelm "Entwicklung Real-Time-PCR-basierter Methoden für die moderne DNA-Analytik" Dissertation, 2003, Gießen, S. Meuer "Rapid cycle real time PCR", Springer 2004, ISBN 3-540-66736-9, T. Weissensteiner "PCR-Technology: current innovations" CRC Press 2004 ISBN 0-8493-1184-5). The distance between the position of the nuc-macromolecule in the nucleic acid chain and that of the nucleotide of the same nucleic acid chain which takes part as a substrate in an enzymatic reaction falls within, for instance, the following ranges (number of nucleotides): 0 to 3, 3 to 6, 6 to 10, 10 to 20, to 40. The number 0 means that the nuc-macromolecule is coupled directly to the nucleotide taking part in the reaction.

Some examples of the use of Nuk-macromolecules are discussed below.

Processes in the Liquid Phase

In one embodiment of the labeling processes, the nucleic acid chains to be labeled are in the liquid phase, see examples 34, 35.

Many different processes, e.g. PCR, Nick-Translation, Random-Primer-Reaktion, reverse Transkription with Reversen Transkriptasen and transcription with RNA polymerases ("Molecular Cloning", 3. Sambrook, 3. Ed. In 2001), can be carried out with nuc-macromolecules according to the present invention. In these processes, nuc-macromolecules are added in the reaction in a similar way to nucleotides modified conventionally with a dye. General rules for the use of conventionally modified nucleotides, such as, for example, dCTP-Cy3 (Amersham Bioscience) or dUTP-TMR (NEN) are described in detail in the literature ("Molecular Cloning", J. Sambrook, 3. Ed. 2001). For instance, one type of nuc-macromolecule, e.g. dATP or dCTP, can be used for the coupling of a single complementary nucleotide to the primer. However, mixtures of modified and unmodified nucleotides are used in most reactions (H. Yu et al. Nucleic Acid Research 1994, v. 22 p. 3226-, "Molecular Cloning", 3. Sambrook, 3. Ed. 2001). For instance, labeled and unlabeled nucleotides can be mixed in the following ratios in the case of labeling with a nuc-macromolecule comprising dUTP:

dATP: dCTP: dGTP: dTTP: dUTP-nuc-macromolecule=1:1:1:0.5:0.5 dATP: dCTP: dGTP: dTTP: dUTP-nuc-macromolecule=1:1:1:0.7:0.3 dATP: dCTP: dGTP: dTTP: dUTP-nuc-macromolecule=1:1:1:0.9:0.1 or dATP: dCTP: dGTP: dTTP: dUTP-nuc-macromolecule=1:1:1:0.7:0.3 or dATP: dCTP: dGTP: dTTP: dUTP-nuc-macromolecule=1:1:1:0.95:0.05 the precise mixture ratios can be optimized for individually selected reactions.

Furthermore, several types of nuc-macromolecule can be used in a reaction. For instance, nuc-macromolecules can carry different markers. In one embodiment, the markers of the nuc-macromolecules are selected in such a way that they form a FRET pair (Faner, R et al. *Hum Immunol* 2004, v. 65, p. 826-38, Lazowski, K. W. et al. *Antisense Nucleic Acid Drug Dev* 2000, v. 10, p. 97-103, Talavera, E. M. *Appl Spectrosc* 2003, v. 57, p. 208-15, Tsourkas, A. et al. *Anal Chem,* 2003, v. 75, p. 3697-703, Singh, K. K., et al. *Methods Mol Biol* 2004, v. 252, p. 33-48, Wang, L. *Spectrochim Acta A Mol Biomol Spectrosc,* 2004, v. 60, p. 2741-50).

After the incorporation of such nuc-macromolecules in the growing nucleic acid chain the average distance between the fluorophores decreases, so that FRET occurs between the donors and the acceptor. Since nuc-macromolecules carry a much stronger marker than conventionally modified nucleotides, the signal intensity of the FRET signal can be greater. The precise condition of the reaction can be optimized by means of the choice of fluorophore, its coupling to the nuc-macromolecule, the concentration of nuc-macromolecules and the ratio between the nuc-macromolecules and unlabeled nucleotides. As a general rule, the average distance between the fluorophores of a FRET pair should be no greater than 10 nm.

Solid Phase Processes

In a further embodiment of the labeling processes, the nucleic acid chains to be labeled or their complementary stands are attached to a solid phase. Many processes for the labeling of immobilized nucleic acid chains with conventionally modified nucleotides are known (Suomalainen A et al. Methods Mol Biol. 2003, Pirrung M C et al. Bioorg Med Chem Lett. 2001 Sep. 17; v. 11(18): p. 2437-40). Microparticles are examples of the solid phase (Spherotech Inc, Streptavidin-polystyre Particle, 2.17µ). An incorporation reaction on solid phase with nuc-macromolecules is described in example 34C. Another example of solid phase are planar surfaces to which nucleic acids are bound.

Nuc-macromolecules are suitable for analysis processes with an incorporation reaction with nucleic acid coupled to a solid phase; nuc-macromolecules can be used similarly to conventionally modified nucleotides in many processes, such as, for example, minisequencing (Suomalainen A et al. Methods Mol Biol. 2003; 226:361-6. Liljedahl U et al. Pharmacogenetics. 2003 January; v. 13(1): p. 7-17, Olsson C et al. Methods Mol Biol. 2003; v. 212: p. 167-76), primer extension (Pirrung M C et al. Bioorg Med Chem Lett. 2001 Sep. 17; v. 11(18): p. 2437-40, Cal H, et al. Genomics. 2000 Jun. 1; v. 66(2): p. 135-43., Kurg A et al. Genet Test. 2000; v. 4(1): p. 1-7., Pastinen T et al. Genome Res. 1997 June; 7(6):606-14). U.S. Pat. No. 6,287,766, U.S. Patent No. 2003148284, U.S. Patent No. 2003082613, EP 1256632, WO0194639, WO 2004/076692, Ju et al. U.S. Pat. No. 6,664,079. solid phase PCR (WO 9626291, WO 9409156, U.S. Pat. No. 6,221,635), Sequenzierung durch die Synthese (Ju et al U.S. Pat. No. 6,664,079), single-molecular-sequencing (Tcherkassov WO 02088382, Seeger WO 0018956, Kartalov WO 02072892). In many cases, a synthesis of the complementary chain with the attached primer template complexes occurs.

Signal amplification steps are often required for analysis processes with immobilized nucleic acid chains. In such processes nuc-macromolecules can bring an especial advantage, because signal intensity is superior. The number of signal-giving marker units of nuc-macromolecules can be determined during the synthesis, so that the signal intensity from incorporated nuc-macromolecules can be quantified.

In such processes nuc-macromolecules having fluorescent signals, radioactive signals or enzymes as marker units can be used. Nuc-macromolecules with fluorescent signals are especially advantageous for such processes, because fluorescence enables high sensitivity.

In one embodiment of such processes, fluorescent signals from the markers of incorporated nuc-macromolecules are detected. The nuc-macromolecules used can form a FRET pair. In a further embodiment, labeled primer can be used for the labeling of nucleic acids attached to a solid phase, whereby these primers comprise, in one embodiment, one or several nuc-macromolecules and, in a further embodiment, these primers comprise conventional labelling. In both these embodiments, the labeling within the primer can form one part of a FRET pair. The part of a FRET pair coupled within the primer can act as a donor as well as an acceptor in the detection process. The incorporated nuc-macromolecules with an appropriate partner for the FRET pair can comprise either a removable or a non-removable marker.

A significant increase in the signal specificity can be achieved by the use of FRET between the incorporated nuc-macromolecules and the label attached to the primer. Thereby, detection can occur during the incorporation process or, in another embodiment, as a separate step in the process.

In one embodiment, nuc-macromolecules with a specific type of nuc-component (for instance, dTTP) carry, preferably, a marker component distinctive for each nuc-macromolecule, so that, for instance, four types of nuc-macromolecule (corresponding to dTTP, dCTP, dATP and dGTP) can be used at the same time and can be distinguished. Other labeling schemes are known, e.g. Tcherkassov WO 02088382. Depending on the particular process, unlabeled nucleotides, e.g. naturally occurring nucleotides, are added to the reaction solution together with nuc-macromolecules.

In one embodiment of the labeling process, nuc-macromolecules which permit the incorporation of only a single nuc-component into the growing nucleic acid strand are used, whereby multiple incorporations are prevented by modifications of the nuc-component, and/or of the linker component and/or of the marker component. The continuation of incorporation can be prevented in either a reversible or an irreversible mode. An irreversible stop can be achieved, for instance, by the incorporation of nuc-macromolecules which comprise a dideoxynucleoside triphosphate as a nuc-component.

A reversible stop can be unmade in a subsequent step of the process, so that the Incorporation reaction can continue. Examples of a reversible blockade of the reaction are described (Metzker et al. Nucleic acid Research 1994, v. 22, p. 4259, Canard et al. Gene, 1994, v. 148, p. 1, Kwiatkowski U.S. Pat. No. 6,255,475, Kwiatkowski WO 0125247, Parce WO 0050642, Tcherkassov WO 02088382, Ju et al. U.S. Pat. No. 6,664,079, Milton et al. WO 2004018497, Milton et al. WO 2004018493, Balasubramanian et al. WO 03048387)

In another embodiment, the incorporated nuc-macromolecules do not prevent the ongoing incorporation of further nucleotides. If a mixture of modified and unmodified nucleotides is used, several nuc-macromolecules can be incorporated after the incorporation of an initial nuc-macromolecule into the growing strand.

The solid phase can be, for instance, a planar surface or beads or a kind of array of several vessels (e.g. microtiter plate or nanotiter plate). The nucleic acids can be coupled by a variety of methods to the solid phase (McGall et al. U.S. Pat. No. 5,412,087, Nikiforov et al. U.S. Pat. No. 5,610,287, Barrett et al. U.S. Pat. No. 5,482,867, Mirzabekov et al. U.S. Pat. No. 5,981,734, "Microarray biochip technology" 2000 M. Schena Eaton Publishing, "DNA Microarrays" 1999 M. Schena Oxford University Press, Rasmussen et al. Analytical Biochemistry v. 198, S. 138, Allemand et al. Biophysical Journal 1997, v. 73, p. 2064, Trabesinger et al. Analytical Chemistry 1999, v. 71, p. 279, Osborne et al. Analytical Chemistry 2000, v. 72, p. 3678, Timofeev et al. Nucleic Acid Research (NAR) 1996, v. 24 p. 3142, Ghosh et al. NAR 1987 v. 15 p. 5353, Gingeras et al. NAR 1987 v. 15 p. 5373, Maskos et al. NAR 1992 v. 20 p. 1679). There are known procedures for the amplification of nucleic acid chains starting with single molecules. Such procedures can be used for creation of a population of nucleic acid chains with identical sequence, which have addressable positions on the solid phase, whereby the solid phase can be a planar surface or beads. Preferably, such nucleic acids are hybridized with a primer to form primer template complexes, so that an enzymatic synthesis of complementary strands can proceed ("Molecular Cloning", Maniatis, 3. Ed. In 2001).

Primerextension:

In one embodiment of the process, the incorporation reaction of nuc-macromolecules occurs in one single population of uniform nucleic acid molecules attached onto the solid phase, whereby the marker component of the nuc-macromolecule remains bound to the extended primer after incorporation and is not removed.

Essentially, such processes comprise the following steps:
1) Preparation of a solid phase with attached primer template complexes.
2) Incubation of the prepared solid phase with a reaction solution, which comprises one or several types of polymerase and one or several types of nuc-macromolecule, whereby each nuc-macromolecule can be unambiguously identified by its marker.
3) Removal of the reaction solution and washing of the solid phase.
4) Detection of the signals of the incorporated nuc-macromolecules and identification of each type of incorporated nuc-macromolecule by means of its signal properties.

Sequencing:

In another embodiment of the process, the incorporation reaction of nuc-macromolecules occurs in a single population of uniform nucleic acid molecules attached to the solid phase, whereby the marker component or its single compounds with or without a linker component of the nuc-macromolecule is separated from the nuc-component during or after the incorporation reaction.

Essentially, such processes comprise the following steps:
1) Preparation of a solid phase with attached primer template complexes.
2) Incubation of the prepared solid phase with a reaction solution which comprises one or several types of polymerase and one or several types of nuc-macromolecule, whereby the nuc-macromolecules can be unambiguously identified by their markers.
3) Removal of the reaction solution and washing of the solid phase.
4) Detection of the signals from incorporated nuc-macromolecules and the identification of each type of incorporated nuc-macromolecule according to its signal properties.
5) Removal of the marker component from the incorporated nuc-macromolecules.
6) Repetition of steps 2 to 5.

The repetition can be carried out, for instance, 1 to 2, 2 to 5, 5 to 10, 10 to 20, 20 to 30 times.

In another embodiment of the process, the incorporation of nuc-macromolecules occurs in an enzymatic reaction in parallel on two or several different populations of uniform nucleic acid populations attached onto a solid phase, whereby the said populations have addressable positions on the solid phase and the marker component of the nuc-macromolecule remains bound to the extended primer after incorporation and is not cleaved away.

These addressable positions can take the form of spots, for instance, in the case of a planar surface. When beads are used as a solid phase, different populations of nucleic acids are attached to different beads. When arrays of vessels (e.g. microtiter plate or nanotiter plate) are used, each individual nucleic acid population is fixed in an individual vessel separately.

Essentially, such processes comprise the following steps:
1) Preparation of a solid phase with attached primer template complexes.
2) Incubation of the said prepared solid phase with a reaction solution which comprises one or several types of polymerase and one or several types of nuc-macromolecule, whereby the nuc-macromolecules can be unambiguously identified by their markers.
3) Removal of the reaction solution and washing of the solid phase.
4) Detection of the signals from incorporated nuc-macromolecules and the identification of each type of incorporated nuc-macromolecule by means of its signal properties.

In another embodiment of the sequencing process, the incorporation of nuc-macromolecules occurs in an enzymatic reaction in parallel on two or several different populations of uniform nucleic acid molecules attached onto a solid phase, whereby the said populations have addressable positions on the solid phase. The uniform nucleic acid populations can be attached to a surface by various means (see above). In a special embodiment of the processes, the marker component or its individual constituents is/are separated from the incorporated nuc-macromolecule (with or without a linker component of the nuc-macromolecule) during or after the incorporation reaction. Nuc-macromolecules with a cleavable bond in the linker are suitable for such processes. In the case of planar surfaces, the addressable positions can take, for instance, the form of spots. When beads are used as a solid phase, different populations of nucleic acids are fixed on different beads. When arrays with multiple vessels are used, individual nucleic acid populations are fixed in individual vessels separately.

Essentially, such processes comprise the following steps:
1) Preparation of a solid phase with attached primer template complexes.
2) Incubation of the prepared solid phase with a reaction solution which comprises one or several types of polymerase and one or several types of nuc-macromolecule, whereby the nuc-macromolecules can be unambiguously identified by their markers.
3) Removal of the reaction solution and washing of the solid phase.
4) Detection of the signals from incorporated nuc-macromolecules and the identification of each type of incorporated nuc-macromolecule according to its signal properties.
5) Removal of the marker component from the incorporated nuc-macromolecules.
6) Repetition of steps 2 to 5.

The repetition can be carried out, for instance, 1 to 2, 2 to 5, 5 to 10, 10 to 20, 20 to 30, to 50, 50 to 100, 100 to 200 times.

In one embodiment of the said process, in step (2), nuc-macromolecules are used together with other modified nucleotides. Thereby, the synthesis of the complementary strand takes place gradually: complementary strands are extended at most by one nucleotide per one synthesis step. Control of the enzymatic reaction is achieved through reversible terminators. Preferably, terminators are with modifications on 3' OH group and no additional modifications on the base are used. After the cleavage of the modification from the incorporated nucleotide, further synthesis can proceed on these strands. The structure of the nuc-macromolecules used in this embodiment can vary. Preferably, these will be nuc-macromolecules with terminating properties, i.e. after their incorporation, no additional nucleotide can be incorporated by a polymerase. Preferably, the linker is coupled to the base of the nuc-component and comprises a cleavable bond. The mixing of nuc-macromolecules with terminating properties and reversible terminators allows for differentiation between labeling and reversible termination within a single population of nucleic acid chains. Because the nuc-macromolecules have a terminating action in this embodiment of the process, a smaller number of nucleic acid chains is available in every further step of the sequencing reaction. In order to proceed with the incorporation reaction, a part of the strands has to be blocked reversibly. The fraction of nucleic acid chains modified with nuc-macromolecules can be very small, because the signal power of the nuc-macromolecules can be substantial. The ratio between the nuc-macromolecules and reversible terminators in a reaction step can fall, for instance, within the following ranges: 100:1 and 1:10, 10:1 and 1:1, 1:1 and 1:10, 1:10 and 1:100, 1:100 and 1:1000 (concentration of nuc-macromolecules: concentration of reversible terminators). This ratio can remain steady during the whole sequencing reaction or vary. Since polymerases can accept the nuc-macromolecules and the reversible terminators differently, several kinds of polymerases can be used during the incorporation step. The removal of the signals after detection leads to a better signal to noise ratio during subsequent rounds of detection and is typical of the processes of sequencing by synthesis. The removal of reversible termination can be carried out in a separate step of the process or can be combined, for instance, with the removal of the labeling.

The advantage of using nuc-macromolecules is that the labeling of a small portion of the whole population is sufficient for the detection of the incorporation event. This allows the sequencing reaction to be conducted with smaller quantities of starting material. The use of reversible terminators with a protective group on 3' positions and a base without modification leads to the result that, after the removal of the blocking protective group, the nucleotide remaining in the nucleic acid chain carries no further modifications and therefore can be accepted well by polymerases as a natural substrate.

In a further embodiment of the process, the following steps are carried out:
a) Preparation of at least of one population of single-stranded nucleic acid chains.
b) Hybridisation of sequence-specific primers to the said prepared nucleic acid chains, which results in the formation of nucleic acid chain primer complexes (i.e. NAC primer complexes) capable of extension.
c) Incubation of at least one type of nuc-macromolecule, in accordance with aspects 1 to 25, together with one type of polymerase, in accordance with aspect 31, with NAC primer complexes, prepared in steps (a) and (b), under such conditions as allow for the incorporation of complementary nuc-macromolecules, whereby each type of nuc-macromolecule has characteristic labeling.
d) Removal of the non-incorporated nuc-macromolecules from the NAC Primer complexes.
e) Detection of the signals from the nuc-macromolecules incorporated into the NAC Primer complexes.
f) Removal of the linker component and the marker component from the nuc-macromolecules incorporated into the NAC Primer complexes.
g) Washing the NAC Primer complexes.

If necessary, repetition of steps (c) to (g).

In a further embodiment of the processes, the incorporation reaction of nuc-macromolecules occurs simultaneously on a population of different nucleic acid molecules attached to a solid phase, whereby the said nucleic acid molecules are attached to the solid phase in a random arrangement (Tcherkassov WO 02088382). In this process, sequences are determined for individual nucleic acid chain molecules. The primer nucleic acid complexes taking part in the enzymatic reaction are attached in such a density as allows for the detection of signals from single nuc-macromolecules coupled to a single nucleic acid molecule, but the density of the attached primer or nucleic acid can be substantially higher. For instance, the density of the primer nucleic acid complexes taking part in the incorporation reaction ranges from 1 complex per 10 $\mu m^2$ to 1 complex per 100 $\mu m^2$, from 1 complex on 100 $\mu m^2$ to 1 complex per 1000 $\mu m^2$, from 1 complex per 1000 $\mu m^2$ to 1 complex on 10,000 $\mu m^2$.

Examples of the attachment of nucleic acids to the solid phase in such a density as allows for analyses on single molecules are shown in WO0157248, U.S. Patent No. 2003064398, U.S. Patent No. 2003013101 and WO 02088382. Suitable equipment for detection is described in WO 03031947.

The number of single nucleic acid molecules to be analyzed ranges, for instance, between 1000 and 100,000, 10,000 to 1,000,000, 100,000 to 10,000,000 molecules. The marker component or its individual constituents with or without a linker component of the nuc-macromolecule are cleaved from the nuc-component during or after the incorporation reaction.

The said method for the parallel sequence analysis of nucleic acid sequences (nucleic acid chains, NAC) comprises the following steps, in which:

Fragments (NACFs) of single-strand NACs with a length of approximately 50-1000 nucleotides are produced that may represent overlapping partial sequences of a whole sequence.

The NACFs are bound in a random arrangement using one uniform or several different primers in the form of NACF primer complexes on a reaction surface, whereby the density of NACF primer complexes bound to the surface allows for optical detection of signals from individual incorporated nuc-macromolecules.

A cyclical synthesis reaction of the complementary strand of the NACFs is performed using one or more polymerases by:

a) adding to the NACF primer complexes bound to the surface a solution comprising one or more polymerases and one to four nuc-macromolecules that have a marker component labeled with fluorescent dyes, with concomitant use of at least two nuc-macromolecules with dyes coupled to the marker component, being chosen in such a way that the nuc-macromolecules used can be distinguished from one another by the measurement of different fluorescent signals, with the nuc-macromolecules being structurally modified in such a way that the polymerase, following incorporation of such a nuc-macromolecule in a growing complementary strand, is not capable of incorporating a further nuc-macromolecule in the same strand, with the linker component and marker component being cleavable, b) incubating the stationary phase obtained in step a) under conditions suitable for extending the complementary strands, with the complementary strands being extended in each case by one nuc-macromolecule, c) washing the stationary phase obtained in step b) under conditions suitable for the removal of nuc-macromolecules not incorporated in a complementary strand, d) detecting the single nuc-macromolecules incorporated in complementary strands by measuring the signal characteristic of the respective fluorescent dye, with the relative position of the individual fluorescent signals on the reaction surface being determined at the same time, e) cleaving off the linker component and marker component of the nuc-components added to the complementary strand in order to produce unlabeled (NTs or) NACFs, f) washing the stationary phase obtained in step e) under conditions suitable for the removal of the marker component, repeating steps a) to f), where appropriate several times, with the relative position of individual NACF primer complexes on the reaction surface and the sequence of these NACFs being determined by specific assignment of the fluorescent signals detected in step d) in successive cycles in the respective positions to the nuc-macromolecules.

Application of Nucleic Acid Chains Comprising Nuc-Macromolecules.

Surprisingly, after the incorporation of a nuc-macromolecule to the 3' end of the nucleic acid, these modified nucleic acid chains, for their part, retain the ability to couple further nucleotides to the 3'-hydroxyl group by means of polymerases (see example 34C). This means that not only is the nuc-component in the nuc-macromolecules able to remain available, but also the nucleic acid chains modified with those nuc-macromolecules are available for the enzymes, and can find applications in different areas of biotechnology. Not only nucleic acid chains modified on 3' ends with nuc-macromolecules, but also nucleic acid chains which comprise one or several nuc-macromolecules as monomers at 5' ends or in the internal positions of the nucleic acid polymer, retain their substrate properties for polymerases, exonucleases and ligases. Examples of the applications of oligonucleotides modified with nuc-macromolecules are known to experts in this field, e.g. primer extension reactions, real time PCR or ligase reactions.

Choice of Enzymes

As monomers, nucleotides play a central role in different metabolic processes, for instance, in the storage and transmission of genetic Information in the cell ("Genes V" B. Lewin, 1994). Nucleotides are also known as an energy source in the cell (ATP, UTP), or as messengers (GTP) in intracellular signal mediation ("Biochemie and Pathobiochemie", G. Löffler, 2003). For these reasons, nucleotides and their analogues are used as therapeutics and diagnostic tools. Nucleotide monomers, coupled to nucleic acid polymers (nucleic acid chains), form the basis for information storage in living organisms.

Nuc-macromolecules have the potential to find applications in different areas of biotechnology.

The possibility of coupling nucleotides to a macromolecule while retaining the substrate properties of the nucleotides also opens many avenues for the specific addressing of the modified nucleotides within an organism or a cell, so that nuc-macromolecules display a new basic model for nucleotide-prodrugs.

Various types of polymerase, for instance, can be used as enzymes ("DNA Replication", Kornberg, 2. Ed. 1992), in particular, DNA-dependent DNA polymerases, RNA-dependent DNA polymerases, DNA-dependent RNA polymerases and RNA-dependent RNA polymerases. Thermostable as well as thermolabile polymerases can be used, as for example Klenow polymerase or Taq polymerase. The specialist will be able to find other examples of suitable polymerases in the literature cited here. Transferases constitute another example of enzymes, e.g. deoxynucleotidyl transferase ("Molecular Cloning", Maniatis, 3. Ed. 2001). Also other enzymes and proteins (for instance, kinases, membrane receptors) that accept nucleotides as substrates, an energy source, co-factors or as messenger substances, can be used.

Enzymes differ in their ability to accept modified nucleotides as substrates. It will be obvious to the specialist that different functional tests must be used to examine and to apply certain properties of nucleotides. Examples of different test procedures for the labeling of nucleic acids are shown in H. Held et al. Nucleic Acid Research 2002, v. 30, p. 3857, M. Metzger et al. Nucleic Acid Research 1994, v. 22, p. 4259, M. Herrlein et al. Helvetica Chimica Acta 1994, v. 77, p. 586, B. Canard et al. PNAS 1995, v. 92, p. 10859, Canard U.S. Pat. No. 5,798,210, J. Hovinen et al. 3. Chem. Soc. Perkin 1994, 1994, 211 and also in other patents and publications cited here.

Accordingly, suitable combinations of polymerases and modified nucleotides can be selected for each respective purpose. Examples of the incorporation of nuc-macromolecules into the primer are shown in example 34. The examples shown do not aim at the restriction of the range of application of nuc-macromolecules, but are intended to display to the specialist the difference in properties of nuc-macromolecules as compared to conventional modified nucleotides.

Nuc-macromolecules or their intermediates can be also used in the conventional chemical synthesis of oligonucleotides, for instance, in a solid phase synthesis (Giegrich, "Neue photolabile Schutzgruppen für die lichtgesteuerte Oligonucleotidsynthese", 1997, Beier, "Neue Strategien zum Aufbau von RNA- und DNA-Oligonucleotiden", 1996), whereby the nuc-component of the nuc-macromolecules carries suitable modifications, making the said nuc-macromolecules suitable for chemical coupling to the nucleic acid chain, as for example in Herrlein, "Synthese von modifizierten Nukleosiden, Nukleotiden und Oligonukleotiden", 1993, Gugler, "Aufbau und Anwendung von Systemen zur vereinfachten chemo-enzymatischen Synthese von Oligonukletid-Hybridisierungssonden", 1993, Schmidt, "Neue Methoden zur Synthese und Isolierung langkettiger Oligonucleotide", 1991, Bühler, "Neue photolabile Schutzgruppen für die Oligonucleotidsynthese", 2000, Bretzger, "Wege zur präparativen Oligonucleotidsynthese" 1991, Stengele, "Automatisierte Oligonucleotidsynthese unter Verwendung [beta]-eliminierbare Schutzgruppen", 1991.

Another aspect of the present invention is a quick purification method for labeled nucleotides directly before their use in the labeling reaction. Processes for the sequencing of single molecules (e.g. Balasubramanian WO 03048387, Tcherkassov WO 02088382, Kartalov WO02072892) need labeled nucleotides in a very pure state, because impurities within preparations of nucleotides, such as unlabeled nucleotides, can cause a sequence error. For this reason it is important that the modified nucleotides be essentially free from unmodified nucleotides. Many modified nucleotides used in the said processes comprise one or several groups which are cleavable under mild conditions (Balasubramanian WO 03048387, Tcherkassov WO 02088382).

During storage, such nucleotides can disintegrate to some extent, thus constituting a source of analogous nucleotides without a marker, which would lead to an error in the sequence if used in an incorporation reaction with nucleic acid.

This problem means that a purification procedure has to be applied directly before the use of labeled nucleotides. A standard cleaning procedure for modified nucleotides is, for instance, an HPLC purification with a water-methanol gradient. After such purification the fraction with modified nucleotides must be further processed, for instance, by lyophilisation. Such a purification procedure is laborious.

According to this invention, nuc-macromolecules can be cleansed of the slightest impurities by ultrafiltration directly before use. The filters are selected by pore size in such a way that nucleotides without a marker can pass through the pores. However, nucleotides modified with a macromolecular marker cannot pass through the filter. Using such purification, nuc-macromolecules can be obtained in a pure state in a very short time.

Another aspect of the invention is the use of the modified exo minus Klenow fragment of DNA polymerase together with nuc-macromolecules in enzymatic reactions, whereby the SH group of the cysteine of the exo minus Klenow fragment of DNA polymerase is modified chemically.

This modification is preferably a covalent modification. Examples of such a modification are seen in alkylation of the SH group, e.g. with alphahalogen-acetyl derivative, e.g. iodoacetamide and its derivatives, iodine acetate and its derivatives, or with N-maleimide derivatives, while still further selective reagents for SH groups are known ("Chemistry of protein conjugation and crosslinking" Shan S. Wong 1993 CRC Press Inc). Such modification can also be carried out using a fluorescent dye. Activated fluorescent dyes which react selectively with SH groups are commercially available, e.g. from Molecular Probes Inc.

In one preferred embodiment of the invention, a selective modification of the exo minus Klenow fragment of DNA polymerase occurs on the SH group of the cysteine. An example of the production of such an exo minus Klenow fragment of DNA polymerase is shown in example 43.

In another embodiment, other modifications of DNA polymerase can also be made, such as, for example, modifications of the amino groups of the DNA-polymerase.

In one embodiment, the exo minus Klenow fragment of DNA polymerase modified on the cysteine can be used instead of unmodified DNA polymerase together with nuc-macromolecules in an enzymatic incorporation reaction.

General Suggestions for the Synthesis of Nuc-Macromolecules

The nuc-macromolecules according to the invention can be synthesized in different ways. The order of the chemical steps during the coupling steps can vary. For instance, the linker component can be coupled to the nuc-component first, and the marker component can be coupled afterwards. On the other hand, one or more linkers can be coupled to the marker component and then to the nuc-component(s).

The coupling between individual components of nuc-macromolecules can be covalent or affine by its nature. The linking of individual components of the nuc-macromolecules can thereby be accomplished both by chemical and by enzymatical coupling. Couplings to amino or thiol groups represent examples of covalent binding (D. Jameson et al. Methods in Enzymology 1997, v. 278, p. 363-, "The chemistry of the amino group" S. Patai, 1968, "The chemistry of the thiol group" S. Patai, 1974). Biotin-streptavidin bonding, hybridization between complementary strands of nucleic acids or antigen-antibody interactions represent examples of affinity binding.

The macromolecular markers often offer a variety of possibilities for coupling. One macromolecular marker can have a number of coupling positions for the linkers, e.g. several binding sites for biotin, as is true in the case for streptavidin. A macromolecular marker can comprise several amino or thiol groups. The core component of a marker can be modified by a different number of signal-giving or signal-transmitting units. The exact ratio between these marker units can vary. Examples for the modification of polymers with dyes are known (Huff et al. U.S. Pat. No. 5,661,040, D. Brigati U.S. Pat. No. 4,687,732). If nucleic acids are used as macromolecular markers, they can comprise different parts for the coupling of other macromolecules. Other macromolecules, e.g. enzymes, can be bound to one macromolecular marker.

A nuc-macromolecule can carry macromolecular markers with different detection properties, for instance, a nuc-macromolecule can carry several dye molecules as well as sites for the affinity binding (e.g., via hybridization) of further macromolecules.

The coupling between the nuc-components and the linker components is preferably covalent. Many examples of a covalent coupling to nucleotides or their analogues are known (Jameson et al. Method in Enzymology, 1997, v. 278, p. 363-, Held et al. Nucleic acid research, 2002, v. 30 p. 3857-, Short U.S. Pat. No. 6,579,704, Odedra WO 0192284). The coupling can be accomplished, for instance, to phosphate, amino-, hydroxy- or mercapto groups.

Often, the linker component can be built up in several steps. In the first step, for instance, a short linker with a reactive group is coupled to the nucleotide or nucleoside, e.g., propargylamine-linker to pyrimidines Hobbs et al. U.S. Pat. No. 5,047,519 or other linkers, e.g. Klevan U.S. Pat. No. 4,828, 979, Seela U.S. Pat. No. 6,211,158, U.S. Pat. No. 4,804,748, EP 0286028, Hanna M. Method in Enzymology 1996 v. 274, p. 403, Zhu et al. NAR 1994 v. 22 p. 3418, Jameson et al. Method in Enzymology, 1997, v. 278, p. 363-, Held et al. Nucleic acid research, 2002, v. 30 p. 3857-, Held et al. Nucleosides, nucleotides & nucleic acids, 2003, v. 22, p. 391, Short U.S. Pat. No. 6,579,704, Ward et al. U.S. Pat. No. 4,711,955, Engelhardt et al. U.S. Pat. No. 5,241,060 Taing et al. U.S. Pat. No. 6,811,979, Odedra WO 0192284, Herrlein et al. Helvetica Chimica Acta, 1994, V. 77, p. 586, Canard U.S. Pat. No. 5,798,210, Kwiatkowski U.S. Pat. No. 6,255,475, Kwiatkowski WO 01/25247, Parce WO 0050642, Faulstich et al. DE 4418691, Phosphoroamidite (Glen Research Laboratories, http://www.glenres.com/, Trilink Biotechnologies, S. Agrawal "Protocols for oligonucleotide conjugation", Humana Press 1994, M. Gait "Oligonucleotide synthesis: a practical approach" IRL Press, 1990), dissertation "Synthese basenmodifizierter Nukleosidtriphosphate and ihre enzymatische Polymerisation zu funktionalierter DNA", Oliver Thum, Bonn 2002.

Some compounds are commercially available, e.g., from Trilink Biotechnologies, Eurogentec, Jena Bioscience.

These short linkers serve as coupling units L or their parts, and are constituents of the linker component in the completed nuc-macromolecule.

The coupling of the nucleotide or nucleoside with a short linker to a linker-polymer can be accomplished in the second step. Polymers with reactive functional groups are commercially available (Fluka).

After the coupling of the nucleotide to the polymer, the marker component now can be coupled as the last step.

It is often advantageous to couple a short linker to a nucleoside and then, if necessary, to convert this modified nucleoside into a nucleoside triphosphate (synthesis of triphosphates can be found, for instance, in the following citations: Held et al. Nucleosides, nucleotides & nucleic acids, 2003, v. 22, p. 391, Faulstich et al. DE 4418691, T. Kovacs, L. Ötvös, Tetrahedron Letters, Vol 29, 4525-4588 (1988) or dissertation "Synthese basenmodifizierter Nukleosidtriphosphate und ihre enzymatische Polymerisation zu funktionalierter DNA", Oliver Thum, Bonn 2002). Further modifications can be carried out with nucleoside triphosphate analogs.

Precursors for modified nucleosides are available, for instance, from Trilink Biotechnologies (San Diego, APPROX., the USA) or from Chembiotech (Muenster, Germany).

The coupling between the linker component and the marker component can occur, for instance, between the marker component and the reactive groups on the linker component. Reagents for such couplings are described in detail in "Chemistry of protein conjugation and crosslinking", S. Wang, 1993, ISBN 0-8493-5886-8. The abovementioned patents also describe the methods for handling and coupling several macromolecules for different types of macromolecules. Further examples (for proteins) of couplings to and between the macromolecules are described in "Bioconjugation: protein coupling techniques for the biomedical sciences", M. Aslam, 1996, ISBN 0-333-58375-2; "Reactive dyes in protein an enzyme technology", D. Clonis, 1987, ISBN 0-333-34500-2; "Biophysical labeling methods in molecular biology" G. Likhtenshtein, 1993, 1993, ISBN 0-521-43132-8; "Techniques in protein modification" R. Lundblad, 1995, ISBN 0-8493-2606-0; "Chemical reagents for protein modification" R. Lundblad, 1991, ISBN 0-8493-5097-2; for nucleic acids in "Molecular-Cloning", J. Sambrook, Vol. 1-3, 2001, ISBN 0-87969-576-5, for other types of polymers in "Makromoleküle, Chemische Struktur and Synthesen", Vols. 1, 4, H. Elias, 1999, ISBN 3-527-29872-X.

Because the marker component usually comprises many coupling positions, it is possible to carry out further modifications with the assembled nuc-macromolecules. For instance, further modifications can block or change excess free amino groups.

Depending on the field of application and reaction conditions under which nuc-macromolecules are used, different types of chemical bonds between separate parts of the macromolecules can be advantageous. Thus, for instance, nuc-macromolecules that have covalent, thermostable bonds between different parts are suitable for processes that involve steps at higher temperatures, hybridization or PCR for example.

In the following, some possible methods for synthesis of nuc-macromolecules will be described for the sake of example. These are not intended to restrict the possible synthesis paths or to restrict the possible nuc-macromolecule structures.

The following provides examples of nuc-macromolecules with polyethylene glycol (PEG) as a linker component. Examples of the coupling of PEG to other molecules are shown in "Poly(ethylene glycol): chemistry and biological applications", 1997. In particular, very different reactive groups can be used for the coupling: N-succinimidyl carbonate (U.S. Pat. No. 5,281,698, U.S. Pat. No. 5,468,478), amines (Buckmann et al. Makromol. Chem. V. 182, p. 1379 (1981), Zalipsky et al. Eur. Polym. J. V. 19, p. 1177 (1983)), succinimidyl propionate and succinimidyl butanoate (Olson et al. in Poly(ethylene glycol) Chemistry & Biological Applications, 170-181, Harris & Zalipsky Eds., ACS, Washington, D.C., 1997; U.S. Pat. No. 5,672,662), succinimidyl succinate (Abuchowski et al. Cancer Biochem. Biophys. v. 7, p. 175 (1984), Joppich et al., Makromol. Chem. 1v. 80, p. 1381 (1979), benzotriazole carbonate (U.S. Pat. No. 5,650,234), glycidylether (Pitha et al. Eur. 3. Biochem. v. 94, p. 11 (1979), Elling et al., Biotech. Appl. Biochem. v. 13, p. 354 (1991), oxycarbonylimidazole (Beauchamp, et al., Anal. Biochem. v. 131, p. 25 (1983), Tondelli et al. 3. Controlled Release v. 1, p. 251 (1985)), p-nitrophenyl carbonate (Veronese, et al., Appl. Biochem. Biotech., v. 11, p. 141 (1985); and Sartore et al., Appl. Biochem. Biotech., v. 27, p. 45 (1991)), aldehyde (Harris et al. 3. Polym. Sci. Chem. Ed. v. 22, p. 341 (1984), U.S. Pat. No. 5,824,784, U.S. Pat. No. 5,252,714), maleimide (Goodson et al. Bio/Technology v. 8, p. 343 (1990), Romani et al. in Chemistry of Peptides and Proteins v. 2, p. 29 (1984)), and Kogan, Synthetic Comm. v. 22, p. 2417 (1992)), orthopyridyl-disulfide (Woghiren, et al. Bioconj. Chem. v. 4, p. 314 (1993)), Acrylol (Sawhney et al., Macromolecules, v. 26, p. 581 (1993)), Vinylsulfone (U.S. Pat. No. 5,900,461). Additional examples for coupling PEG to other molecules are shown in Roberts et al. Adv. Drug Deliv. Reviews v. 54, p. 459 (2002), U.S. Patent No. 2003124086, U.S. Patent No. 2003143185, WO 03037385, U.S. Pat. No. 6,541,543, U.S. Patent No. 2003158333, WO 0126692

Other similar polymers can be coupled in a similar way. Examples of such polymers are poly(alkylene glycol), copolymers of ethylene glycol and propylene glycol, poly (olefinic alcohols), poly(vinylpyrrolidone), poly(hydroxyalkylmethacrylamide), poly (hydroxyalkyl methacrylate), poly(saccharide), poly(x-hydroxy acids), poly(acrylic acid), poly(vinyl alcohol).

The purification of the nuc-components of the nuc-macromolecules is accomplished using conventional means of nucleotide chemistry: for instance, with silica gel chromatography in a water-ethanol mixture, ion exchange chromatography in a salt gradient and reverse-phase chromatography in a water-methanol gradient. Sigma-Aldrich, for example, offers optimized chromatography columns for nucleotide purification.

The purification of macromolecular linker components and marker components can be performed through ultrafiltration, gel electrophoresis, gel filtration and dialysis, see "Bioconjugation: protein coupling techniques for the biomedical sciences", M. Aslam, 1996, ISBN 0-333-58375-2.

The mass of the nuc-macromolecules differs substantially from the mass of the nucleotides. For this reason it is advantageous to use the ultrafiltration for the final purification steps. Since only an average mass is calculated for the nuc-macromolecules, ultrafiltration is also suitable as an analytic method for separation of synthesis products.

It is possible to apply different methods of the macromolecular chemistry for the characterization of the nuc-macromolecules, e.g., UV-vis spectroscopy, fluorescence measurement, mass spectroscopy, fractionation, size exclusion chromatography, ultracentrifugation and electrophoretic technologies, like IEF, denaturating and non-denaturating gel electrophoresis ("Makromoleküle, Chemische Struktur and Synthesen", Band 1, 4, H. Elias, 1999, ISBN 3-527-29872-X, "Bioconjugation: protein coupling techniques for the biomedical sciences", M. Aslam, 1996, ISBN 0-333-58375-2). The measurement of free SH groups in a substance is carried out with Ellmans reagent (5,5'-dithiobis (2-nitrobenzolic acid), Riddles et al. Method in Enzym. 1983, V. 91, p. 49.

Modified Nucleic Acid Chains

In one embodiment of the invention, nucleic acid chains comprise nuc-components of the nuc-macromolecules as units of the chain.

Synthesis of Modified Nucleic Acid Chains

Nuc-macromolecules can be incorporated or integrated into nucleic acid chains as monomers of a polymer chain by different means. Generally, enzymatic and chemical steps can be used. In the following, different strategies for synthesis will be presented.

Chemical Incorporation:

In chemical coupling, an entire nuc-macromolecule (i.e. structure as nuc-linker-marker) or its parts, e.g. nuc-component or nuc-linker structure, can be used in the reaction. For example, the nuc-component can first be introduced into the nucleic acid chain according to the rules of oligonucleotide synthesis (MWG Biotech, TriLink Biotechnologies, Glen Research Laboratories, S. Agrawal "Protocols for oligonucleotide conjugation", Humana Press 1994, M. Gait "Oligonucleotide synthesis: a practical approach" IRL Press, 1990), wherein one monomer of the chain carries a protective reactive group suitable for modification, e.g. a protected aminogroup or mercapto-group. After removal of the protective group, the linker component and the marker component can be coupled to the oligonucleotide. The purification step can comprise ultrafiltration or gel electrophoresis, for example.

Enzymatic Incorporation:

Similarly as in the case of the chemical incorporation, it is possible to use an entire nuc-macromolecule (i.e. structure as nuc-linker-marker) or its parts, e.g. nuc-component or nuc-linker-component, in the enzymatic reaction. For example, nuc-components that carry a reactive group suitable for coupling to a linker component are incorporated into the nucleic acid chain as triphosphates by a template-dependent polymerase-controlled reaction. The linker component or the marker can then be coupled. In one embodiment, a whole nuc-macromolecule can be incorporated into the nucleic acid chain (see example 34).

Modified nucleic acid chains comprise ribonucleic and deoxyribonucleic chains.

The ratio between the nuc-macromolecules and non-modified monomers in a nucleic chain preferably comprises the following ranges: 1:5 and 1:20, 1:20 and 1:100, 1:50 and 1:1000, 1:500 and 1:10000. Several nuc-macromolecules can be also incorporated into a single nucleic acid chain. In one embodiment, one nucleic acid chain comprises only one nuc-macromolecule. In another embodiment, one nucleic acid chain comprises a number of nuc-macromolecules, this number ranging between 2 to 5, 5 to 50, 10 to 100.

In one embodiment, a nuc-macromolecule is integrated at the 5' end of the nucleic acid chain. In a further embodiment, a nuc-macromolecule is integrated at the 3' end of the nucleic acid chain. In a still further embodiment, a nuc-macromolecule is integrated within the nucleic acid chain, wherein the distance to the nearest end of the nucleic acid chain comprises the following ranges (number of nucleotide monomers in the chain to the nearest chain end): 1 to 2, 2 to 4, 4 to 8, 8 to 15, 15 to 30, 30 to 100, 100 to 500.

3. Synthesis of Modified Nucleotides

Methods for Separation

Thin Layer Chromatography, TLC:

Analytical TLC: "DC-Alufolien 20×20 cm Kieselgel 60 F 254" (VWR, Germany), coated with fluorescent indicator. Visualization was conducted with UV light. Separation medium: ethanol/water mixture (70:30), (separation medium, German "Laufmittel", LM 1) or ethanol/water (90:10), LM2. Preparative TLC plates: silica gel plates with collecting layer (VWR, Germany). LM 1 or LM 2.

Reverse-Phase Chromatography (RP Chromatography), RP-18:

C-18 material (Fluke, Germany), column volume 10 ml, water/methanol gradient. Fractions, each 10 ml, were collected and analyzed with a UV-vis spectrometer. Fractions with similar spectra were combined and lyophilized. HPLC columns with the same material can also be used.

Ion-Exchange Chromatography:

DEAE cellulose (VWR, Germany), gradient $NH_4HCO_3$ 20 mmol/l to 1 mol/l, fractions were collected under UV/vis-control; those with similar spectra were combined.

Affinity isolation can be used for purification of nuc-macromolecules, e.g. if there are oligonucleotides as a part of the marker component. Such selective isolation can be accomplished for example via a hybridization on the complementary nucleic acid immobilized on a solid phase.

Estimation of the yields of the dye-marked product was conducted with UV-vis spectrometry.

An estimation of saturation degree of the binding to streptavidin was conducted via a control titration with biotin dye (biotin-4-fluorescein, Sigma), 100 μmol/l in 50 mmol/l borate buffer, pH 8, for 5 min at RT. If all potential sites for binding were saturated during the synthesis, there would be no binding of biotin dye to the streptavidin. In the case of insufficient reaction, there would be binding of biotin dye that can be measured by UV-vis.

Material

Diamino PEG 10,000 (diamino-polyethylene glycol 10,000, Sigma), dUTP-AA (dUTP allyl amine, Jena Bioscience), dCTP-PA (dCTP-Propargyl-Amin, Jena Bioscience), dATP-PA (7-(3-Amino-1-propynyl)-2'deoxy-7-deazaadenosin-5'-Triphosphat) (custom synthesis by JenaBioscience), dGTP-PA (7-(3-Amino-1-propynyl)-2'deoxy-7-deazaguanosin-5'-Triphosphat, (custom synthesis by JenaBioscience), TTP (thymidine triphosphate, can be also called dTTP, Sigma), 3'-Amino-TTP (3'-Amino-3'-deoxy-thymidine-triphosphate, Trilink Biotechnologies), PDTP (3-(2-pyridinyl-dithio)-propionic acid, Fluka), 7-(3-phthalimido-1-propynyl)-2'-deoxy-7-deazaguanosine and 7-(3-phthalimido-1-propynyl)-2'-deoxy-7-deazaadenosine (Chembiotech), PDTP-NHS (3-(2-pyridinyl-dithio)-propionic acid-N-hydroxysuccinimidyl ester, Sigma), Cy3 (dye, Amersham Bioscience), Cy3-NHS (Cy3-N-hydroxysuccinimidyl ester, Amersham Bioscience), MEA (mercaptoethylamine, Sigma), DTT (1,4-dithio-DL-threitol, Sigma), CA (cystamine, Sigma), TCEP (tris-(2-carboxyethyl)phosphine, Sigma), DTBP (3,3'-dithio-bis-propionic acid, Fluka), biotin-NHS (biotin-N-hydroxysuccinimidyl ester, Sigma). J-Ac (iodoacetate, Sigma), iodoacetamide (Sigma), TEAE (tris-(2-Aminoethyl)amine, Sigma), maleimido-ES-NHS (maleimido-acetic acid-N-hydroxysuccinimidyl ester, Sigma), EDA (ethylendiamine, Sigma), CDI (1,1'-carbonyldiimidazole, Sigma), EDC N-(3-Dimethylaminopropyl)-N-Ethylenecarbodiimide (Sigma), NH2-PEG-Biotin (30 atoms), Sigma), PAS 100 kDa (polyacrylic acid, 100 kDa, Aldrich), NHS-PEG-maleimide, 3,400 Da, biotin-PEG-NHS, 5,000 Da, Fmoc-PEG-NHS, 3,400 Da, mPEG-SPA 5,000 Da, mPEG-SPA 20,000 Da (Nektar), diamine-PEG, 6,000 Da (Fluka), Fmoc-NH-(PEG)$_2$-COOH (20 atoms), (Novabiochem, Merck Biosciences, Darmstadt), Fmoc-Amino-PEG-add (n=11) (BioVectra), aminodextran 70000, aminodextran 500000 (Molecular Probes), 3'-biotin-dT31, an oligonucleotide with a sequence of 31 thymidine monophosphates with a biotin-molecule coupled to the 3'-end (MWG Biotech), 3'-SH-Oligo-dT30, an oligonucleotide with a sequence of 30 thymidine monophosphates with the mercapto group at the 3'-end (MWG-Biotech), 3'-amino-oligo-dT31-5'-Cy3, an oligonucleotide with a sequence of 31 thymidine monophosphates with the amino group coupled to the 3'-end via 6-C linker and the Cy3-dye coupled to the 5'-end (MWG-Biotech), SA (streptavidin, Roche), SA-Cy2 (streptavidin modified with Cy2-dye, Amersham Bioscience). QDot (Qdot 605 streptavidin conjugate, Quantum Dot). Polylysine 1000-2000 (poly-L-lysine hydrobromide 1000-2000 Da, Fluka), polylysine 10,000-20,000 (poly-L-lysine hydrobromide 10,000-20,000 Da, Fluka).

List of Suppliers and Companies:
Aldrich—see Sigma
Amersham—Amersham Bioscience, Freiburg, Germany
Chembiotech—Chembiotech, Münster, Germany
Fluka—see Sigma
Jena Bioscience—Jena Bioscience, Jena, Germany
Molecular Probes—Molecular Probes Europe, Leiden, Netherlands
MWG—MWG Biotech, Ebersberg near Munich, Germany,
Nektar—Nektar Molecular Engineering, previous Shearwater Corporation, Huntsville, Ala., USA
Quantum Dot—Quantum Dot Hayward, Calif., USA
Roche—Roche, Mannheim, Germany
Sigma—Sigma-Aldrich-Fluka, Taufkirchen, Germany
Trilink—Trilink Biotechnologies Inc. San Diego, Calif., USA, Organic solvents were purchased from Fluka at p.a. purity grade or were dried according to standard procedures. For solvent mixtures, the mixing ratio is stated in terms of volume to volume (v/v).

Synthesis of Individual Components

Figure 10:
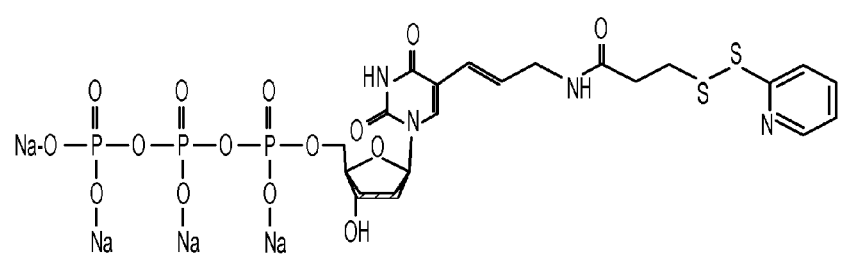
FIG. 10A shows dUTP-AA-PDTP.
FIG. 10B shows dCTP-PA-PDTP.
Figure 10:
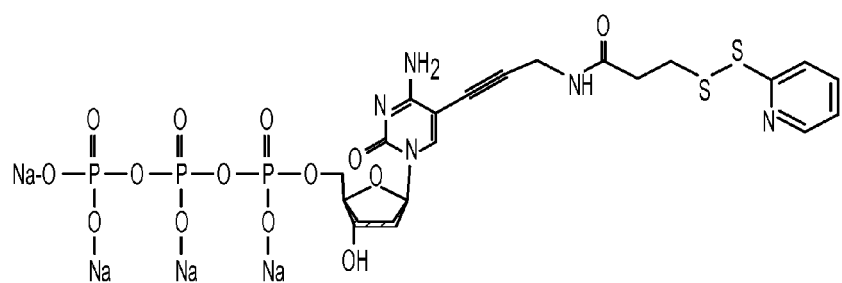
Figure 11:
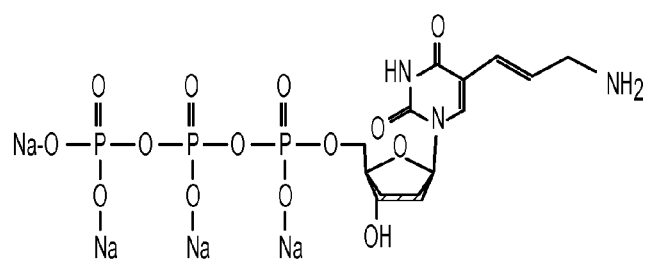
FIGS. 11A, 11B and 11C, 12A, 12B, 12C, 13A, 13B, 13C, 14A, 14B and 14C show examples of various base-modified nucleotide analogs of the invention.
Figure 11:
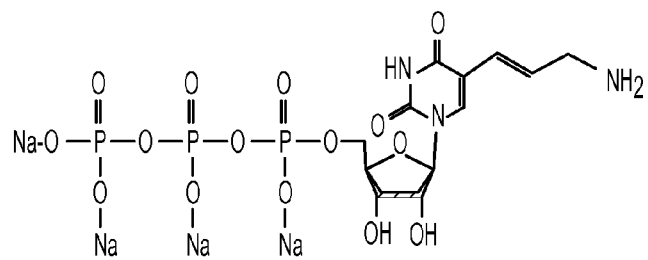
Figure 11:
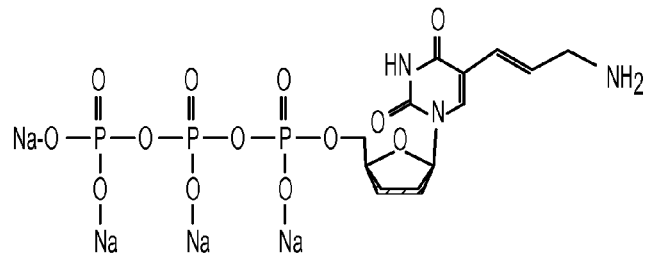
Figure 12:
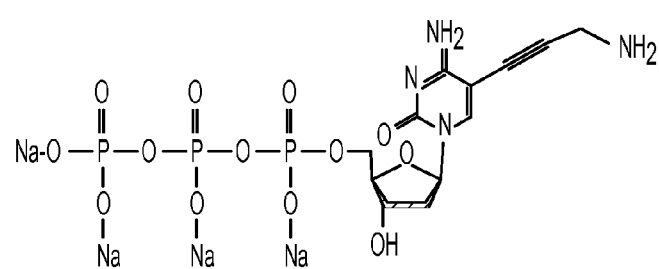
Figure 12:
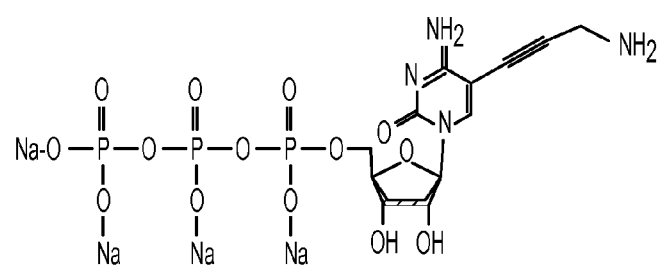
Figure 12:
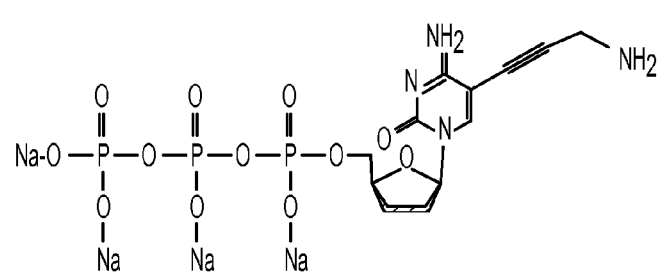
Figure 13:
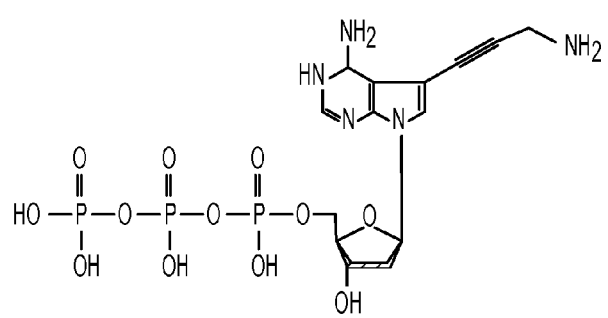
Figure 13:
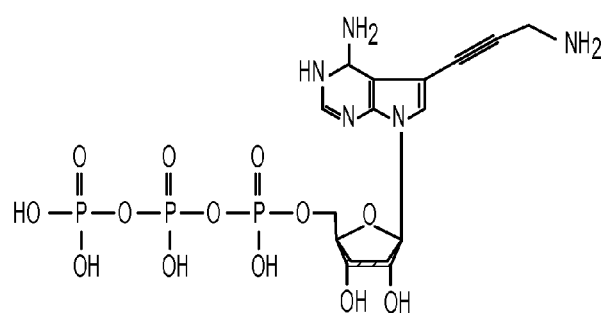
Figure 13:
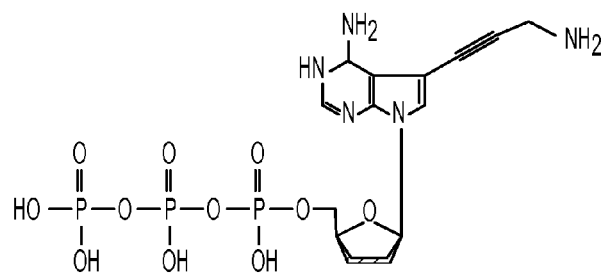
Figure 14:
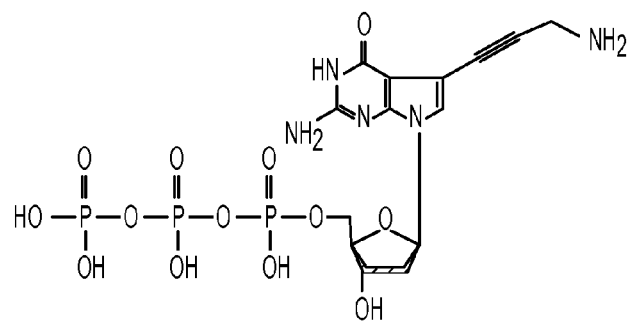
Figure 14:
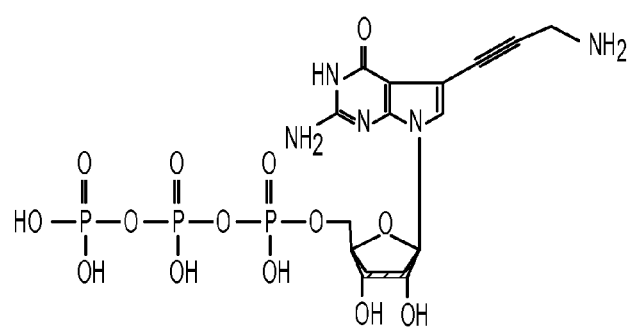
Figure 14:
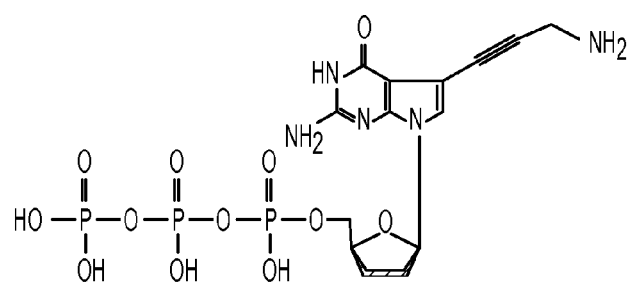

Example 1 dUTP-AA-PDTP, FIG. 10A dUTP-AA (20 mg) was dissolved in 1 ml of water and the pH value was adjusted to 8.5 with NaOH. PDTP-NHS (60 mg dissolved in 0.5 ml methanol) was added dropwise to this aqueous solution of dUTP-AA under stirring. The reaction was carried out at 40° C. for 2 hours. TLC Analysis: dUTP-AA-PDTP (in LM 1 Rf 0.45).

The isolation of the product from excess of PDTP-NHS and PDTP was performed on preparative TLC plates, LM 2. The resulting products, dUTP-AA-PDTP and dUTP-AA, were eluted from the plate with water and dried.

This dUTP analog comprises a disulfide bond that can react with other thiols in a thiol exchange reaction under mild conditions resulting in a formation of a new cleavable bond.

This example illustrates a general possibility of introducing further modifications into the nucleotides. Other base-modified nucleotide analogs, such as 7-deaza-aminopropargyl-deoxy-guanosine triphosphate, 7-deaza-aminopropargyl deoxy-adenosine triphosphate, 5-aminopropargyl-deoxy-uridine triphosphate, 5-aminoallyl-deoxy-uridine triphosphate, and 5-amino-propargyl-deoxy-cytidine triphosphate, can be modified in the same way.

Ribonucleotides as well as 2'-deoxyribonucleotides as well as 2',3'-dideoxyribonucleotides can be used in such reactions, FIGS. 11 to 14.

Example 2 dCTP-PA-PDTP, FIG. 10B

The synthesis was conducted as described above for dUTP-AA-PDTP, example 1.

Figure 15:
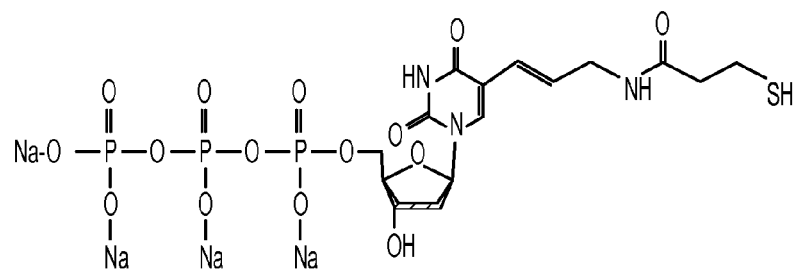
FIG. 15 shows dUTP-AA-propionate-SH, which is described in Example 3.

Example 3 dUTP-AA-propionate-SH, FIG. 15

One ml of aqueous TCEP solution, 250 mmol/l, pH 8, adjusted with NaOH, was added to 200 µl 40 mmol/l aqueous solution of dUTP-AA-PDTP, and the reaction was allowed to proceed for 10 min at RT under stirring. The separation of nucleotides from other reagents took place on preparative TLC plates, LM 2. Under these conditions the product, dUTP-AA-propionate-SH, remains on the starting line. Nucleotides were eluted from the plate with water and dried.

This dUTP analog comprises a reactive SH group that can be easily modified, e.g. by thiol exchange reaction resulting in a new disulfide bond.

Example 4

Figure 16:
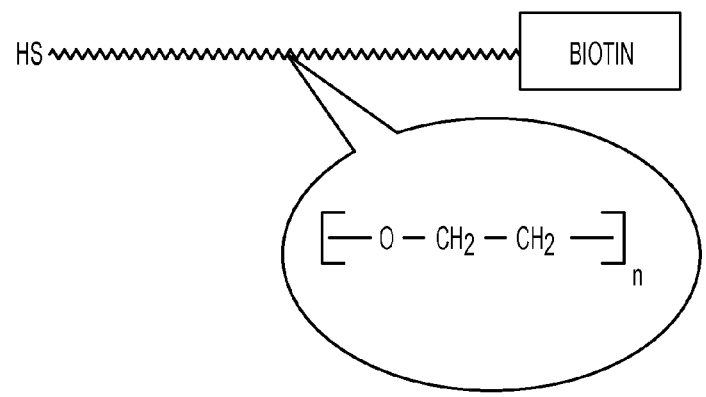
FIG. 16 shows Biotin-PEG-Ethyl-SH, which is described in example 4.

Biotin-PEG-Ethyl-SH, FIG. 16

Biotin-PEG-NHS (10 mg) was added to 200 µl aqueous CA solution (100 mmol/l), pH 8.5, adjusted with NaOH; the reaction proceeded at 40° C. for 18 hours under stirring. Then 200 µl of TCEP solution (0.5 mol/l), pH 8.0, was added and the reaction was allowed to proceed for a further 10 min at RT under stirring. The product was separated from low-molecular-weight compounds by ultrafiltration at a MWCO (Molecular weight cutoff) of 3,000, yield 35%.

The product comprises a reactive SH group that can be easily modified, e.g. by thiol-exchange reaction resulting in a new disulfide bond.

Ten mg of amino-PEG-biotin (30 atoms) were dissolved in 280 µl of 50-mM borate buffer and pH was adjusted to 9. Two equivalents of PDTP-NHS, dissolved in 100 µl of DMF, were added to the resulting solution. After 1 hour at RT, the excess PDTP-NHS was reacted with the excess of $NH_4HCO_3$. Biotin-PEG-PDTP is the resulting product. This product can be coupled to another molecule by thiol exchange. A free SH group can be generated by cleavage of the SS bond.

Example 5

Bis-Dithio-(Ethyl-PEG-Biotin)

Biotin-PEG-NHS (100 mg) was added to 1 ml aqueous CA-Solution (2 mmol/l), adjusted to pH 8.5 with NaOH, and stirred at RT for 18 hours. The product was isolated from the low-molecular-weight compounds via Ultrafiltration at a MWCO of 10,000 and lyophilized, yield 13%.

The product comprises a disulfide bond that can react with other thiols in a thiol exchange reaction.

Example 6

Figure 17:
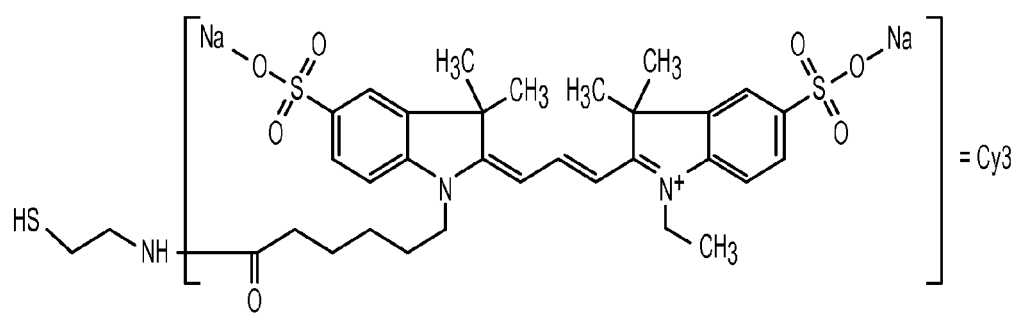
FIG. 17 is MEA-Cy3, and is described in Example 6.

MEA-Cy3, FIG. 17

Cy3-NHS was added to 1 ml aqueous CA-solution (200 mmol/l), adjusted to pH 8.5 with NaOH, until the concentration of the Cy3 dye was 10 mmol/l. The reaction was incubated under continuous stirring at RT for 10 min. Then, 1 ml aqueous TCEP solution (0.5 mol/l), adjusted to pH 8.0 with NaOH, was added, and the reaction was allowed to proceed at RT for a further 10 min. The product was purified on RP-18 (water/methanol gradient), fractions were combined and their volume was reduced to 0.5 ml, yield 93%, UV-vis.

The product has a reactive SH group that can be easily modified, e.g. by thiol-exchange reaction resulting in a new disulfide bond.

Example 7

Figure 18:
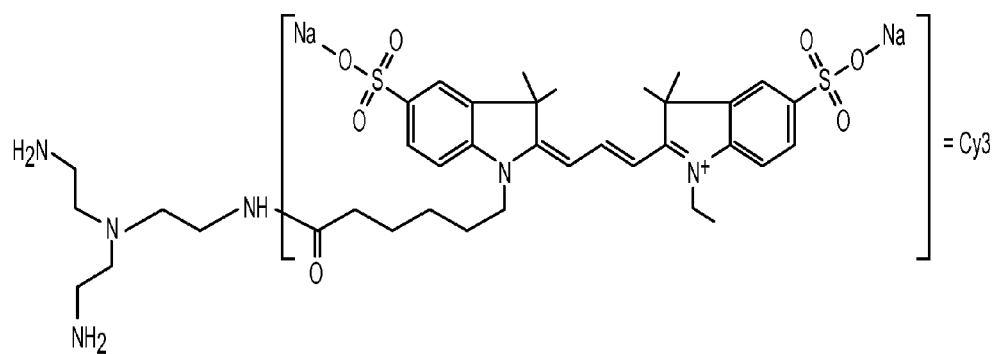
FIG. 18 is Cy3-TEAE, and is described in example 7.

Cy3-TEAE, FIG. 18

Cy3-NHS was added to 1 ml aqueous TEAE-solution (300 mmol/l), adjusted to pH 8.5 with NaOH, until the concentration of the dye reached 5 mmol/l. The reaction was stirred at RT for 10 min. The product was purified on RP-18 and reduced to 0.5 ml, yield 82%, UV-vis.

The product comprises two amino groups that can be modified with other reagents and new functionalities can be coupled to the dye.

Example 8

Figure 19:
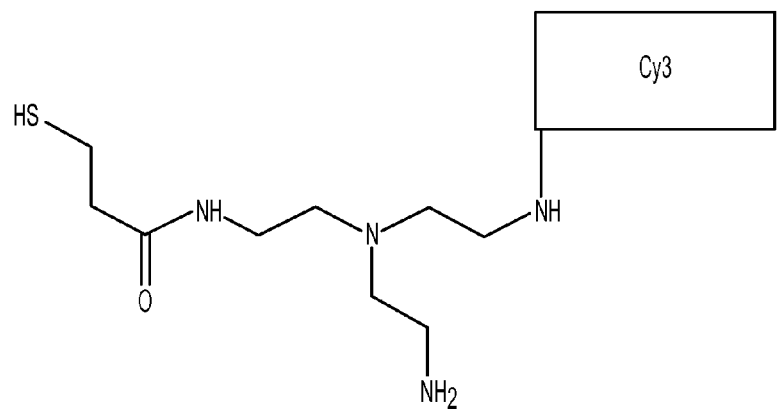
FIG. 19 is Cy3-TEAE-Propionate-SH, as described in Example 8.

Cy3-TEAE-Propionate-SH, FIG. 19

A fresh prepared methanolic solution of PDTP-NHS (30 mmol/l, 30 µl) was added to 300 µl aqueous solution of Cy3-TEAE (2 mmol/l), pH 7.5. The progress of the reaction was observed via TLC, LM 1. The products have the following Rf under these TLC conditions: Rf. 0.55 (Cy3-TEAE-PDTP) and 0.95 (Cy3-TEAE-(PDTP)$_2$). After 1 h at RT, the reaction was stopped and the products were purified on TLC (LM 1). Cy3-TEAE-PDTP (Rf. 0.55) was isolated, dried and dissolved in 200 µl of water. An aqueous TCEP-solution (0.5 mol/l, 0.1 ml), pH 8.0, was added to this Cy3-TEAE-PDTP solution and the reaction was allowed to proceed for 10 min at RT. The product, Cy3-TEAE-propionate-SH, was purified on RP-18 (water/methanol gradient) the volume was reduced to 0.5 ml, yield 26%, UV-vis.

The product comprises a reactive SH group that can be easily modified, in a thiol exchange reaction resulting in a new disulfide bond for example, and an amino-group that can also be modified.

Example 9

Figure 20:
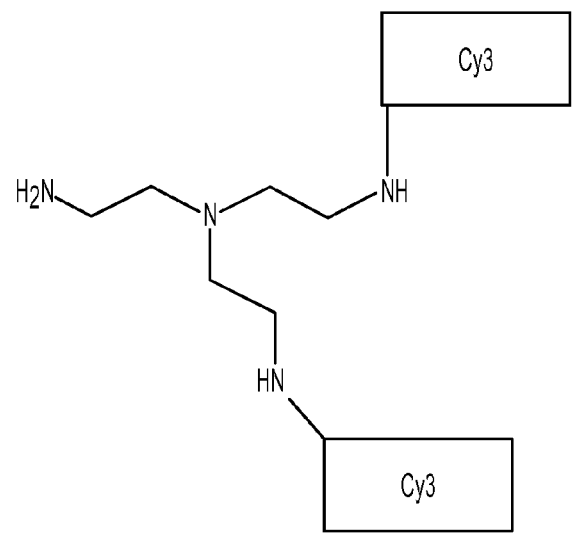
FIG. 20 is TEAE-(Cy3)2, as described in Example 9.

TEAE-(Cy3)2, FIG. 20

Cy3-NHS was added to 1 ml aqueous TEAE solution (2 mmol/l) until the concentration of the dye was 4 mmol/l. The reaction was allowed to proceed under stirring for 10 min at RT. The product, TEAE-(Cy3)2, (Rf. 0.45) was purified from other reagents on preparative TLC in LM 1 and eluted with 50 mmol/l borate buffer, pH 9. Then, TEAE-(Cy3)2 was purified on RP-18 and eluted with 50% ethanol-water and concentrated to a volume of 0.5 ml, yield 22%, UV-vis.

Example 10

Figure 21:
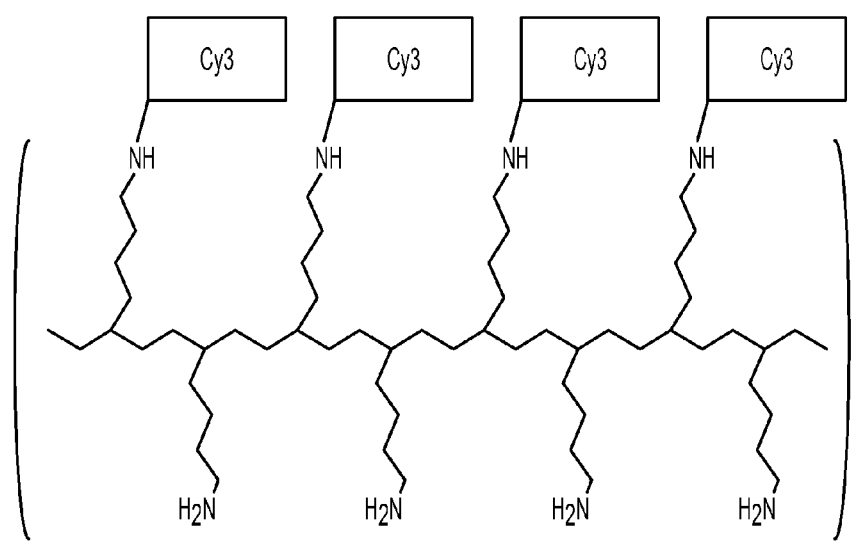
FIG. 21 is Polylysine-(Cy3)n, n=10-15, as described in Example 10.

Polylysine-(Cy3)n, n=10-15, Polylysine 10,000-20,000, FIG. 21

Cy3-NHS was added to 1 ml aqueous polylysine-solution (1 mmol/l) until the concentration of the dye was 18 mmol/l. The reaction was allowed to proceed at RT for 40 min under stirring. Purification of the modified polylysine was carried out via ultrafiltration, 3000 MWCO. UV-vis was used to determine the average number of the Cy3-dye molecules.

Polylysine is an example for a core component to which several marker units can be coupled, e.g. dyes. Distribution of the Cy3 molecules on polylysine was estimated from the known size differences of the polylysine molecules and average number of the coupled Cy3 molecules that was determined.

Example 11

Figure 22:
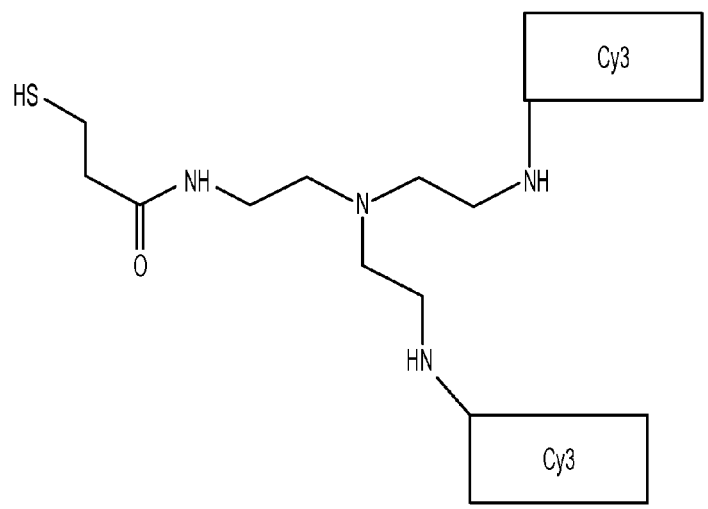
FIG. 22 is TEAE-(Cy3)2-PDTP and TEAE-(Cy3)2-Propionate-SH, as described in Example 11.

TEAE-(Cy3)2-PDTP and TEAE-(Cy3)2-Propionate-SH, FIG. 22

PDTP-NHS (10 mg) was added to 200 µl aqueous solution of TEAE-(Cy3)2 (1 mmol/l) and the reaction was allowed to proceed at RT for 1 h under stirring. The course of the reaction was controlled with TLC, LM 1. After 1 hour there was a nearly quantitative conversion of TEAE-(Cy3)2 (Rf. 0.45) into TEAE-(Cy3)2-PDTP, (Rf. 0.85). The product of the reaction was divided in two equal parts.

The product, TEAE-(Cy3)2-PDTP, from the first part was purified on RP-18 and lyophilized (yield 82%, UV-vis). This product comprises a disulfide bond that can participate in a thiol exchange reaction, i.e. other components can be coupled.

The second part was reacted with 0.1 ml of an aqueous solution of TCEP (0.5 mol/l), pH 8.0, at RT for 10 min under stirring. The product, TEAE-(Cy3)2-propionate-SH, was purified on RP-18, yield 68%, UV-vis.

The product comprises a reactive SH group, that can be modified, e.g. in a thiol exchange reaction resulting in a new disulfide bond.

Example 12

Figure 23:
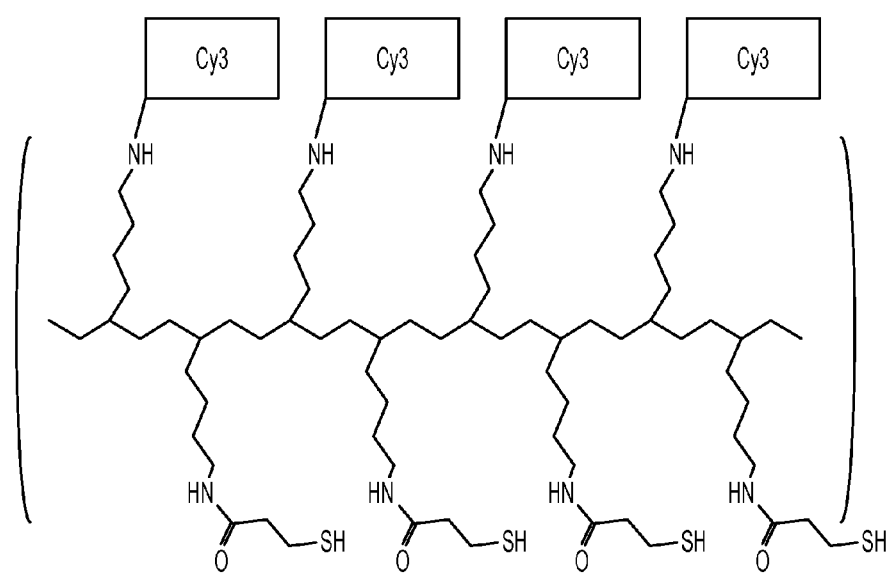
FIG. 23 is (HS-Propionate).$_m$-Polylysine-(Cy3)n, as described in Example 12.

(HS-Propionate)$_m$-Polylysine-(Cy3)$_n$, (n=10-15, m=3-9, Polylysine 10,000-20,000), FIG. 23

PDTP-NHS (10 mg) was added to 200 µl aqueous solution of Polylysine-(Cy3)$_n$ (1 mmol/l) and the reaction was allowed to proceed at RT for 1 hour under stirring. The product (PDTP)$_m$-polylysine-(Cy3)$_n$ was purified from the rests of PDTP via ultrafiltration and then dissolved in 100 µl water. Next, 0.1 ml TCEP solution (0.5 mol/l), pH 8.0, was added and the mixture was stirred at RT for another 10 min. The product, (HS-propionate)$_m$-polylysine-(Cy3)$_n$, was separated from low-molecular-weight compounds at 3,000 MWCO. The product comprises several reactive SH groups that can be modified, e.g. in a thiol exchange reaction resulting in new disulfide bonds.

Example 13

Figure 24:
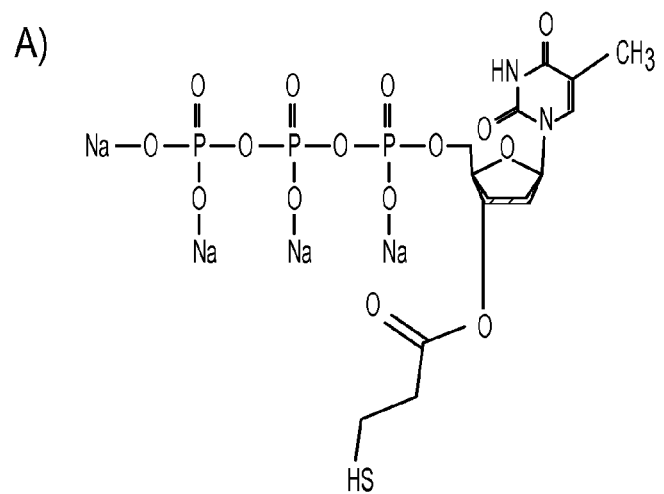
FIG. 24A is TTP-3'-O-Propionat-SH.
FIG. 24B is TTP-3'-Amino-PDTP, as per Examples 13 and 14, respectively.
Figure 24:
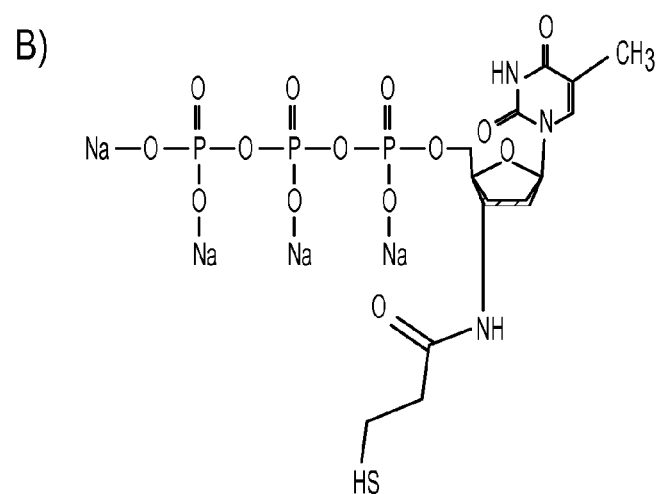

TTP-3'-O-Propionat-SH, FIG. 24A,

The synthesis of 3'-modified nucleotides proceeded according to Gottikh et al. Tetrahedron, 1970, v. 26, 4419-, Schafer et al. Method in Enzymology, 1986, v. 126, pp. 682-.

DTBP, 210 mg, was dissolved in 1 ml DMF. CDI, 320 mg, was added to this solution and the resulting mixture as stirred for 1 hour at RT. Next, 10 µl methanol was added and, after another 10 min, 100 µl of this solution, 1 mol/l, was added to 300 µl aqueous solution of TTP, 100 mmol/l, adjusted to pH 8.5 with NaOH, and the resulting solution was thoroughly stirred at RT for approximately 4 hours. Nucleotides were isolated by precipitation with ethanol and then dissolved in 300 µl water. Next, 200 µl TCEP solution (0.5 mol/l), pH 8.0, was added and, after 10 min at RT, nucleotides were precipitated once again. Preparative separation was not conducted at this stage of synthesis, yield 13%, UV-vis.

The product comprises a reactive SH group that can easily be modified, e.g. in a thiol exchange reaction resulting in new disulfide bond.

Example 14

TTP-3'-Amino-PDTP, FIG. 24B

The synthesis was conducted as described for dUTP-AA in example 1. The following educts were used: 3'-amino-3'-deoxy-TTP, 100 µl, 10 mmol/l solution, pH 8, and PDTP-NHS, yield 19%, UV-vis.

This product comprises a disulfide bond that can participate in thiol exchange reaction, i.e. other components can be coupled.

Other nucleotides modified at the 3'-end, e.g. with a short linker, can also be used. Examples of the synthesis for such compounds are as follows: Metzker et al. Nucleic acid Research 1994, v. 22, s. 4259, Canard et al. Gene, 1994, v. 148, p. 1, Hovinen et al. J. Chem. Soc. Perk. Trans. 1994 v. 1, p. 211, Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Parce WO 0050642, Faulstich DE 4418691.

Additional examples of base-modified nucleotides that can be used a nuc-component are described in Balasubramanian WO 03048387 and still further examples in "Nucleotide Analogs" Scheit, 1980, ISBN 0-471-04854-2, "Nucleoside and Nucleic Acid Chemistry", Kisakürek 2000, "Anti-HIV Nucleosides" Mitsuya, 1997, "Nucleoside Analogs in cancer therapy", Cheson, 1997. A person skilled in the art may recognize that still other modified nucleotides can be used. Examples for Coupling Linker Components and Marker Components to Nuc-Component.

Figure 25:
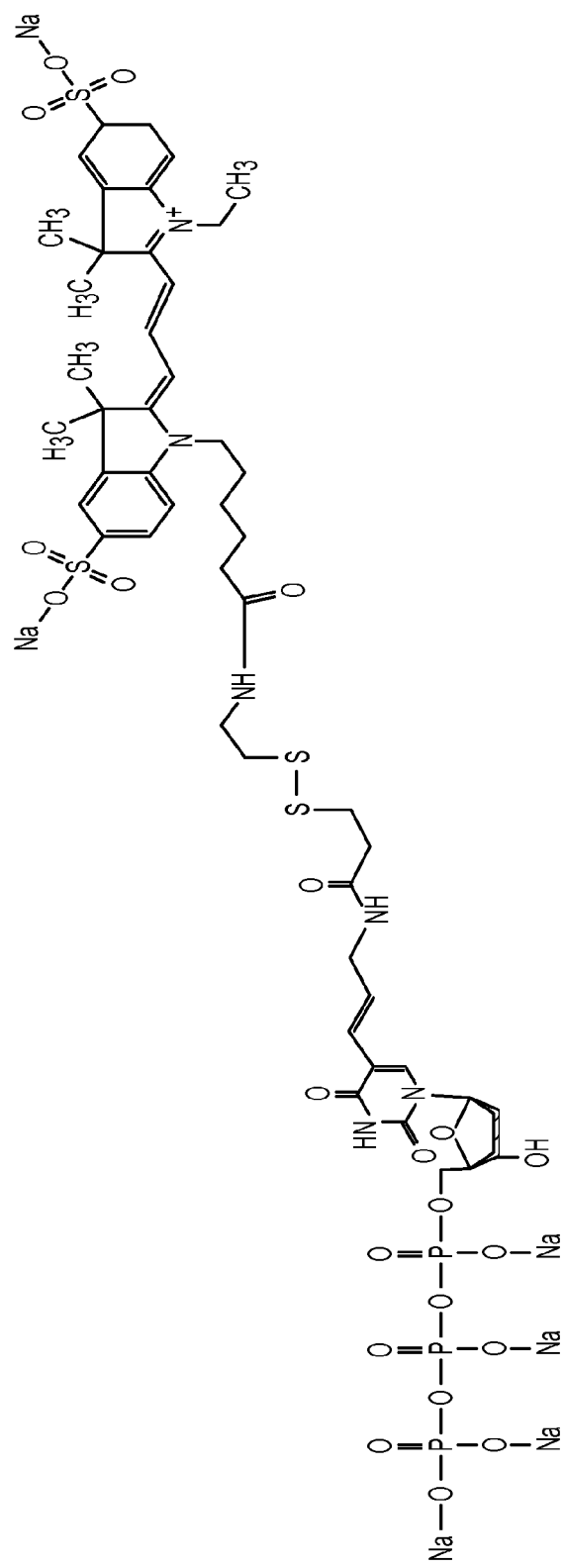
FIG. 25 is dUTP-AA-SS-MEA-Cy3, as described in Example 15.

Example 15 dUTP-AA-SS-MEA-Cy3, FIG. 25 dUTP-AA-PDTP (50 µl, 30 mmol/l in 50 mmol/l borate buffer, pH 9.5) was added to 100 µl, 10 mmol/l MEA-Cy3 in 50 mmol/l borate buffer, pH 9.5. After 1 hour, dUTP-AA-SS-MEA-(Cy3) was separated from MEA-Cy3, Rf. 0.9 by TLC, LM 1, Rf. 0.6. Next, dUTP-AA-SS-MEA-(Cy3) was purified from dUTP-AA-PDTP on RP-18, yield 67%, UV-vis.

The resulting compound comprises a nucleotide functionality and a low-molecular-weight marker functionality. It can be considered as a typical conventional modified nucleotide with only one low molecular marker.

Polymerases do accept this compound as a substrate (e.g. Klenow-exo minus fragment), example 34A.

Figure 26:
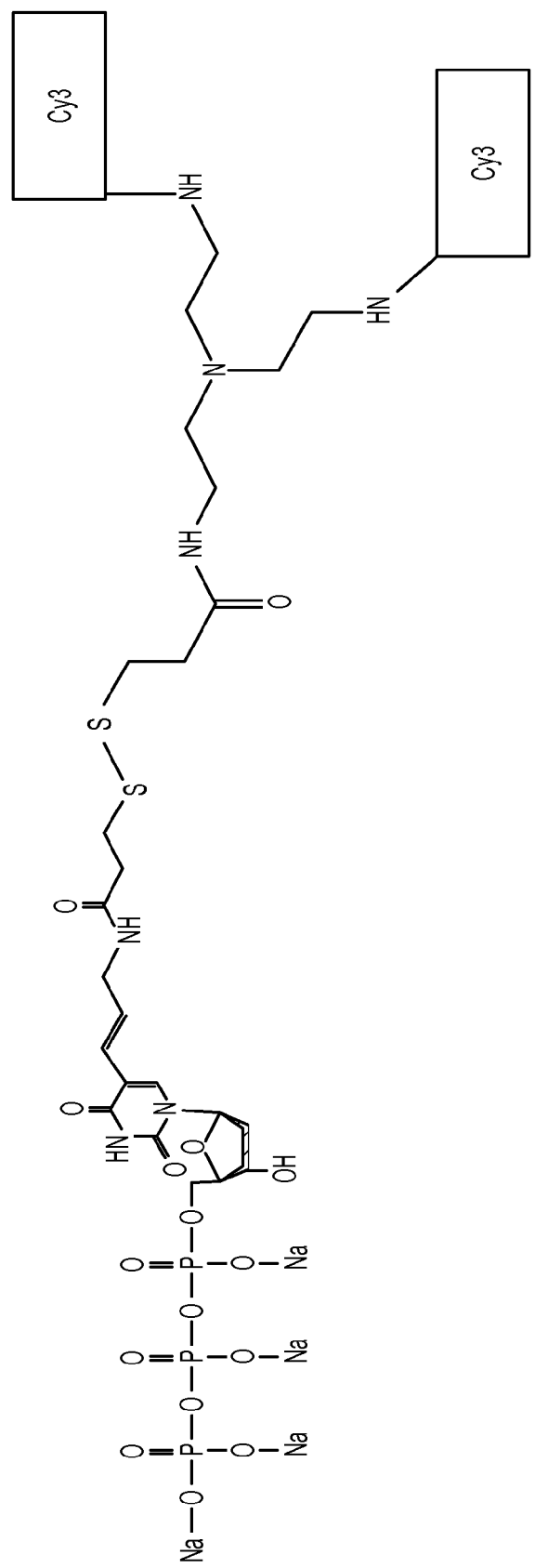
FIG. 26 dUTP-AA-SS-TEAE-(Cy3)$_2$, as described in Example 16.

Example 16 dUTP-AA-SS-TEAE-(Cy3)2, FIG. 26 dUTP-AA-SS-TEAE-(Cy3)2 was synthesized similarly as dUTP-AA-SS-MEA-(Cy3), example 15, except that TEAE-(Cy3)2-propionate-SH was used instead of MEA-Cy3, yield 43%, UV-vis.

The obtained compound comprises a nucleotide functionality and two low-molecular-weight marker functionalities. Polymerases do not accept this compound as a substrate (e.g. Klenow exo minus polymerase). The modification leads to the loss of substrate properties.

Figure 27:
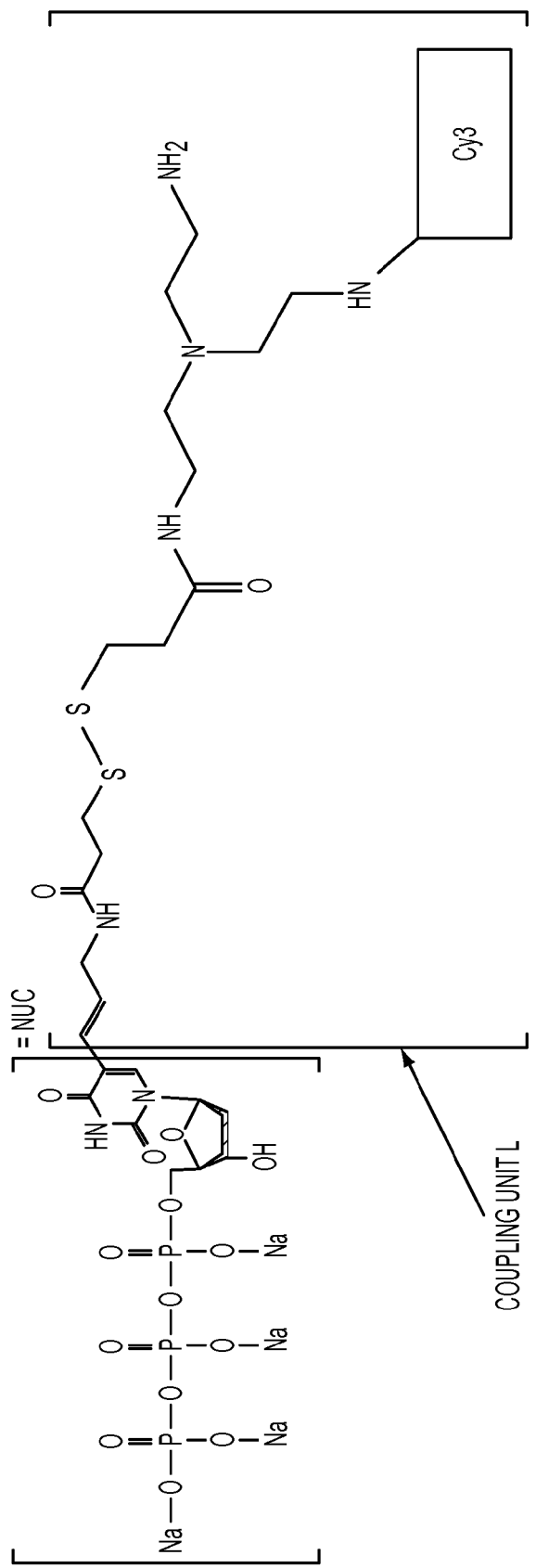
FIG. 27 is dUTP-AA-SS-Propionate-TEAE-Cy3, as described in Example 17.

Example 17 dUTP-AA-SS-Propionate-TEAE-Cy3, FIG. 27 dUTP-AA-SS-propionate-TEAE-Cy3 was synthesized similarly as dUTP-AA-SS-MEA-Cy3, example 15, except that Cy3-TEAE-propionate-SH was used instead of MEA-Cy3, yield 37%, UV-vis.

The resulting compound comprises a nucleotide functionality and a low molecular weight marker functionality. The linker comprises a free amino group that can be modified. Polymerases can use this nucleotide as a substrate.

Example 18

(dUTP-AA-SS-Propionate)m-Polylysine-(Cy3)n

Educts:
dUTP-AA-PDTP
(HS-propionate)m-Polylysine-(Cy3)n, n=10-15, m 3-9, Polylysine 10,000-20,000

An aqueous solution of dUTP-AA-PDTP (50 µl, 20 mmol/l, in 50 mmol/l borate buffer, pH 9.0) was mixed with 20 µl aqueous (HS-propionate)m-Polylysine-(Cy3)n, approximately 1 mmol/l, and the reaction was allowed to proceed at RT for 18 hours under stirring. The product was separated from low-molecular-weight substances via ultrafiltration, 30,000 MWCO.

The obtained compound comprises a nucleotide functionality and a macromolecular-marker functionality.

Polymerases do not accept this compound as a substrate (e.g. Klenow exo minus polymerase or terminal transferase). The modification resulted in the loss of substrate properties.

Figure 28:
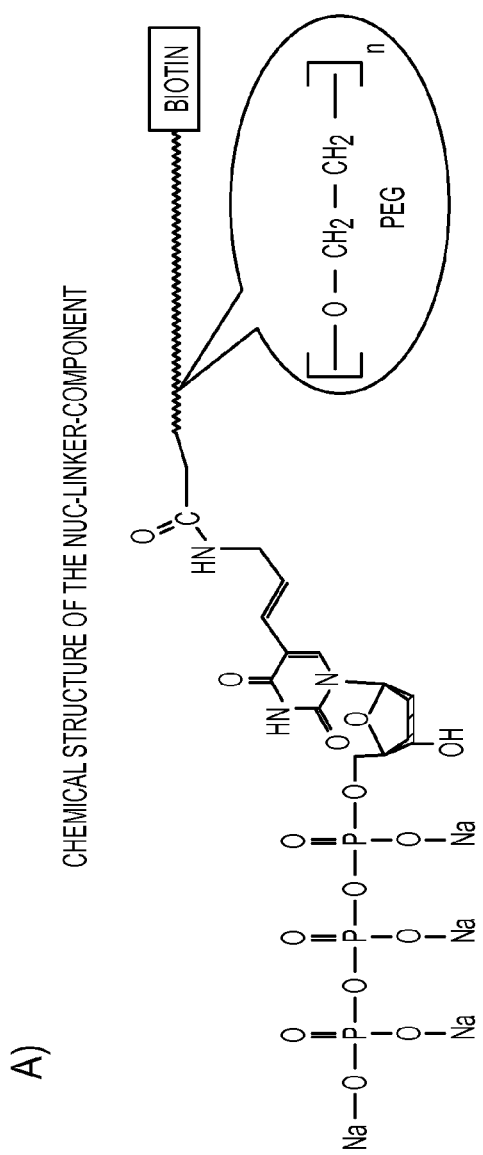
FIGS. 28A and 28B are dUTP-AA-PEG-Biotin, as described in Example 19.
Figure 28:
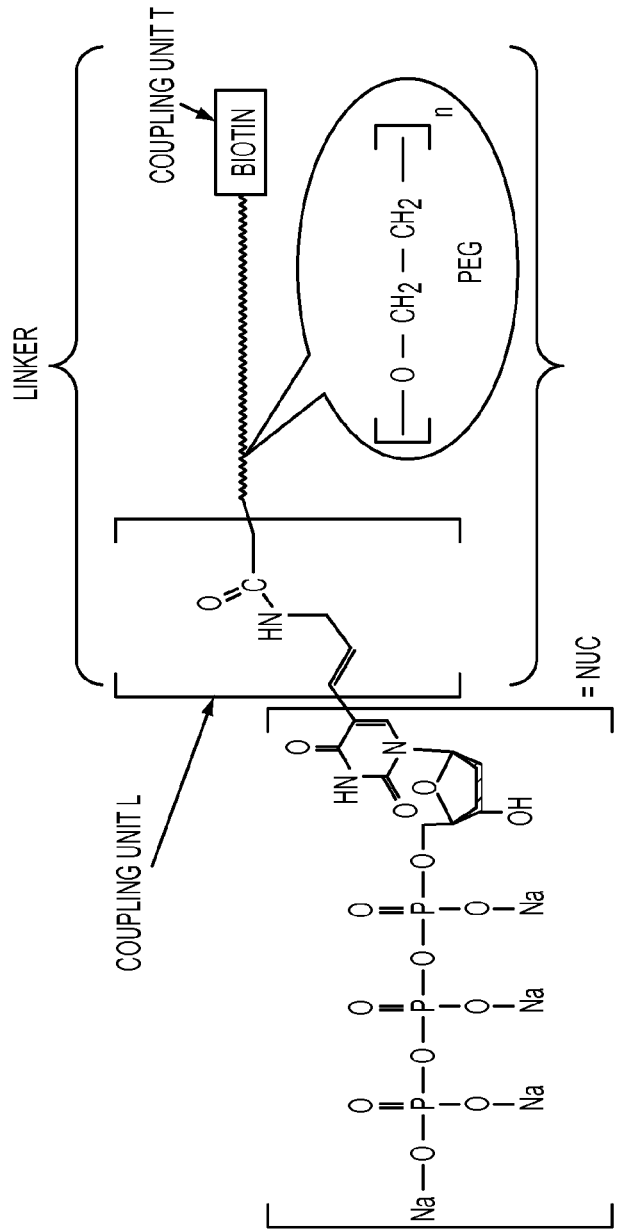

Example 19 dUTP-AA-PEG-Biotin, FIG. 28

Biotin-PEG-NHS (10 mg) was added to 100 µl aqueous solution of dUTP-AA, 50 mmol/l, pH 8.0, and stirred at 40° C. for 18 h. Next, the unreacted nucleotide was separated by ultrafiltration, 3,000 MWCO, and the product, dUTP-AA-PEG-biotin, was thoroughly washed with water.

This compound comprises a nucleotide functionality and a macromolecular linker. Biotin represents the coupling unit (T). Macromolecular structures can be coupled to this coupling unit (T), e.g. streptavidin, without the nucleotide analogs losing their substrate properties. This nuc-macromolecule can be used as a substrate for polymerases.

Also, biotin can be considered as a low-molecular marker unit coupled to a long linker that comprises a signal-transmitting function.

Figure 29:
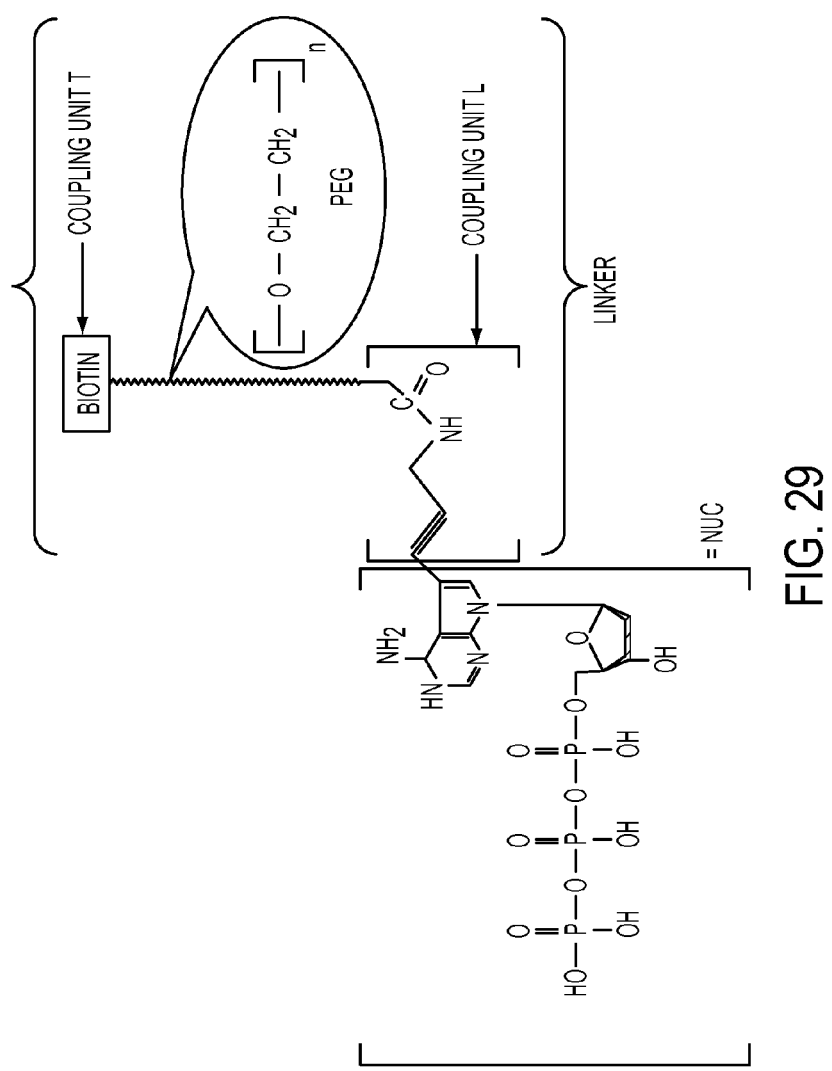
FIG. 29 shows 7-deaza-aminopropargyl-dATP modified in a manner similar to the described procedure in Example 19.

This product is an intermediate compound for a nuc-macromolecule. This example shows that it is generally possible to modify nucleotides. Other base-modified nucleotide analogs, e.g. 5-propargylamino-dCTP, 7-deaza-aminopropargyl-dGTP, 5-amino-propargyl-dUTP and 7-deaza-aminopropargyl-dATP (FIG. 29) can be modified in a manner similar to the described procedure. Ribonucleotides, 2'-deoxyribonucleotide or 2',3'-dideoxyribonucletide can be used, FIGS. 11 to 14.

Other polymers, e.g. PEG derivates, can be used as a linker in a similar way. dATP-PA-PEG-NH$_2$ constitutes one example.

Fmoc-PEG-NHS (Fmoc-protected NH$_2$—PEG-NHS), 10 mg, was added to 100 µl aqueous solution of 7-deaza-7-aminopropargyl-dATP (custom-synthesized from 7-(3-Phthalimido-1-propynyl)-2'-deoxy-7-deazadenosine by Jena Bioscience, Germany), 50 mmol/l, pH 8.0, and stirred at 40° C. for 18 hours. Next, the pH-value was increased to 11 and the reaction mixture was stirred at RT for 2 additional hours. Next, the resulting product, dATP-PA-PEG-NH$_2$, was separated from the unreacted nucleotide by ultrafiltration, 3,000 MWCO, and washed with water several times.

This compound comprises a nucleotide functionality and a macromolecular linker. The NH$_2$ group is a coupling unit (T) for the marker component. Macromolecular structures can be coupled to this coupling unit (T), e.g. polyacrylic acid derivatives, without these nucleotide analogs losing their substrate properties. This nuc-macromolecule can be used as a substrate for polymerases.

Example 20

TTP-3'-Amino-PEG-Biotin

The synthesis was conducted similarly as for dUTP-AA-PEG-biotin, example 19.

3'-amino-3'-deoxy-TTP and biotin-PEG-NHS were used as adducts.

This compound comprises a nucleotide functionality and a macromolecular linker and a low-molecular-weight marker unit (biotin) that has a signal-transmitting function. Signal-carrying streptavidin molecules can be coupled to the biotin.

Other nucleotide analogs with an amino group at the 3'-position can also be synthesized in similar way.

Example 21 dCTP-PA-PEG-Maleimide,

The synthesis was conducted as described for dUTP-AA-PEG-biotin, example 19. dCTP-PA and maleimide-PEG-NHS were used as adducts.

This compound has a nucleotide functionality and a macromolecular linker. The coupling unit (T) at this linker is the maleimide group. Macromolecular signal-carrying molecules with one or more SH groups can be coupled to this maleimide functionality.

This maleimide group can also be considered as a low-molecular-weight marker unit with signal-transmitting function that is coupled to a long linker. Other macromolecular structures can be coupled to this marker component without these analogs losing their substrate properties.

This example shows that it is generally possible to modify nucleotides. Other base-modified nucleotide analogs, e.g. 5-propargylamino-dCTP, 7-deaza-aminopropargyl-dGTP, 5-amino-propargyl-dUTP and 7-deaza-aminopropargyl-dATP can also be modified in the above way. Ribonucleotides, 2'-deoxyribonucleotides or 2',3'-dideoxyribonucleotides can be used, FIGS. 11 to 14.

Figure 30:
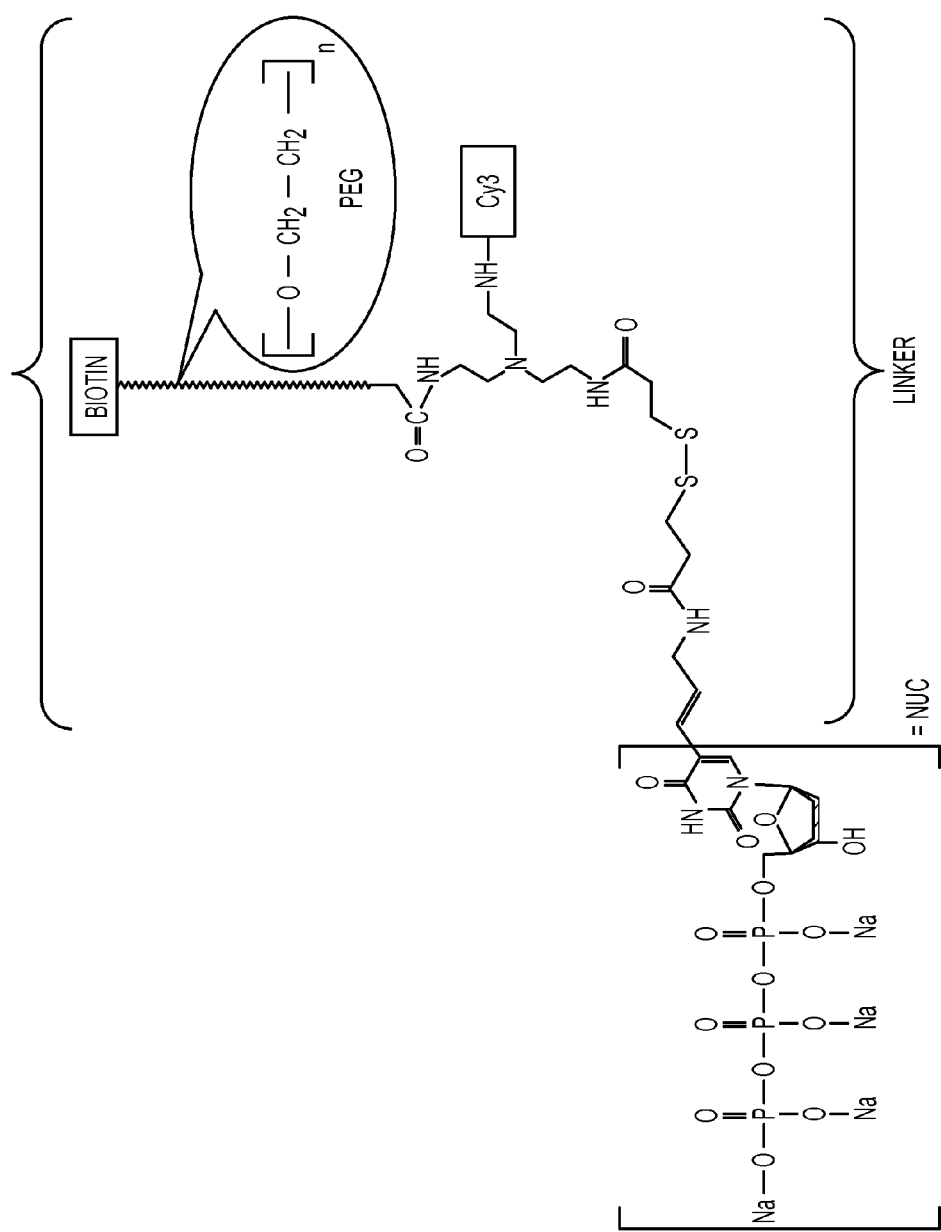
FIG. 30 is dUTP-AA-SS-Propionate-TEAE-(Cy3)-PEG-Biotin, as described in Example 22.

Example 22 dUTP-AA-SS-Propionate-TEAE-(Cy3)-PEG-Biotin, FIG. 30

The synthesis was conducted in a manner comparable to that described for dUTP-AA-PEG-Biotin (example 19). dUTP-AA-SS-Propionate-TEAE-Cy3 and Biotin-PEG-NHS were used as adducts. Separation of the product from non-reacted dUTP-analog was conducted by ultrafiltration, 3.000 MWCO.

This compound comprises a nucleotide functionality, a fluorescent dye, a macromolecular linker and a low molecular weight marker functionality (biotin), that has signal transmitting properties. The biotin molecule can be considered as a coupling unit (T) as well.

Further macromolecules can be coupled to this coupling unit (T)—in this example biotin—without loss of the substrate properties of the nucleotides. This analog acts as a substrate for polymerases.

The dye acts as a sterically demanding group, which allows for only one enzymatic incorporation of a nuc-macromolecule into the growing strand by a polymerase. Properties of such analogs are described in more detail in Tcherkassov WO 02088382.

Figure 31A:
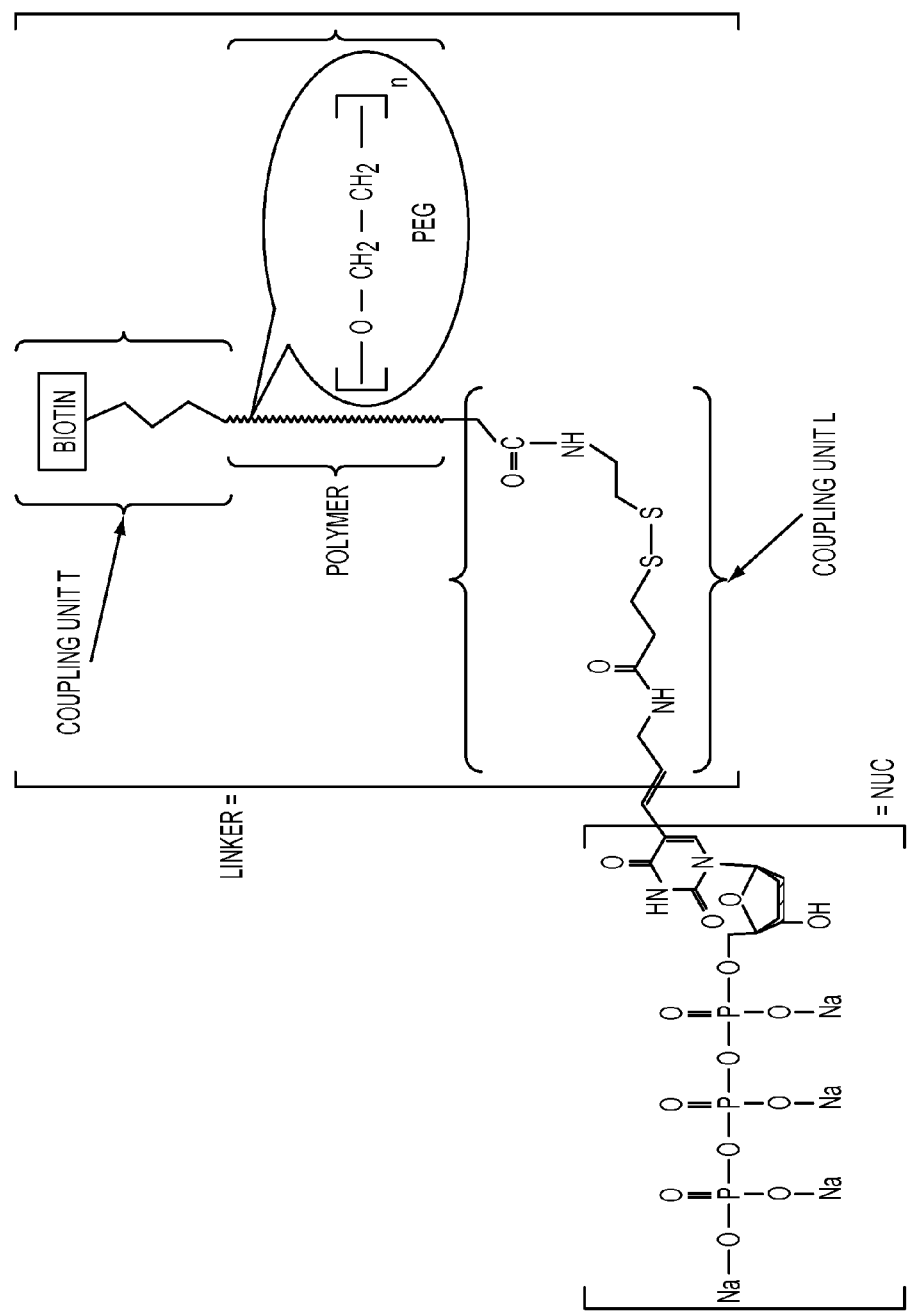
FIG. 31A is dUTP-AA-SS-PEG-Biotin, as described in Example 23.

Example 23 dUTP-AA-SS-PEG-Biotin, FIG. 31A,

A solution of dUTP-AA-PDTP (50 µl, 30 mmol/l in 50 mmol/l borate, pH 9.5) was added to a solution of Biotin-PEG-Ethyl-SH (100 µl, 10 mmol/l in 50 mM borate, pH 9.5). The reaction mixture was stirred for 18 hours at RT. The separation steps were conducted as described for the synthesis of dUTP-AA-PEG-Biotin (example 19).

This compound comprises a nucleotide functionality and a macromolecular linker. Biotin acts as a coupling unit (T). Macromolecular structures can be coupled to this coupling unit (T), e.g. streptavidin, without loss of the substrate properties of this analog. This nuc-macromolecule acts as a substrate for polymerases. Further macromolecules can be coupled via streptavidin, e.g. enzymes or nucleic acids. Biotin can also be considered as a signal-transmitting marker unit with a low molecular weight.

Figure 31B:
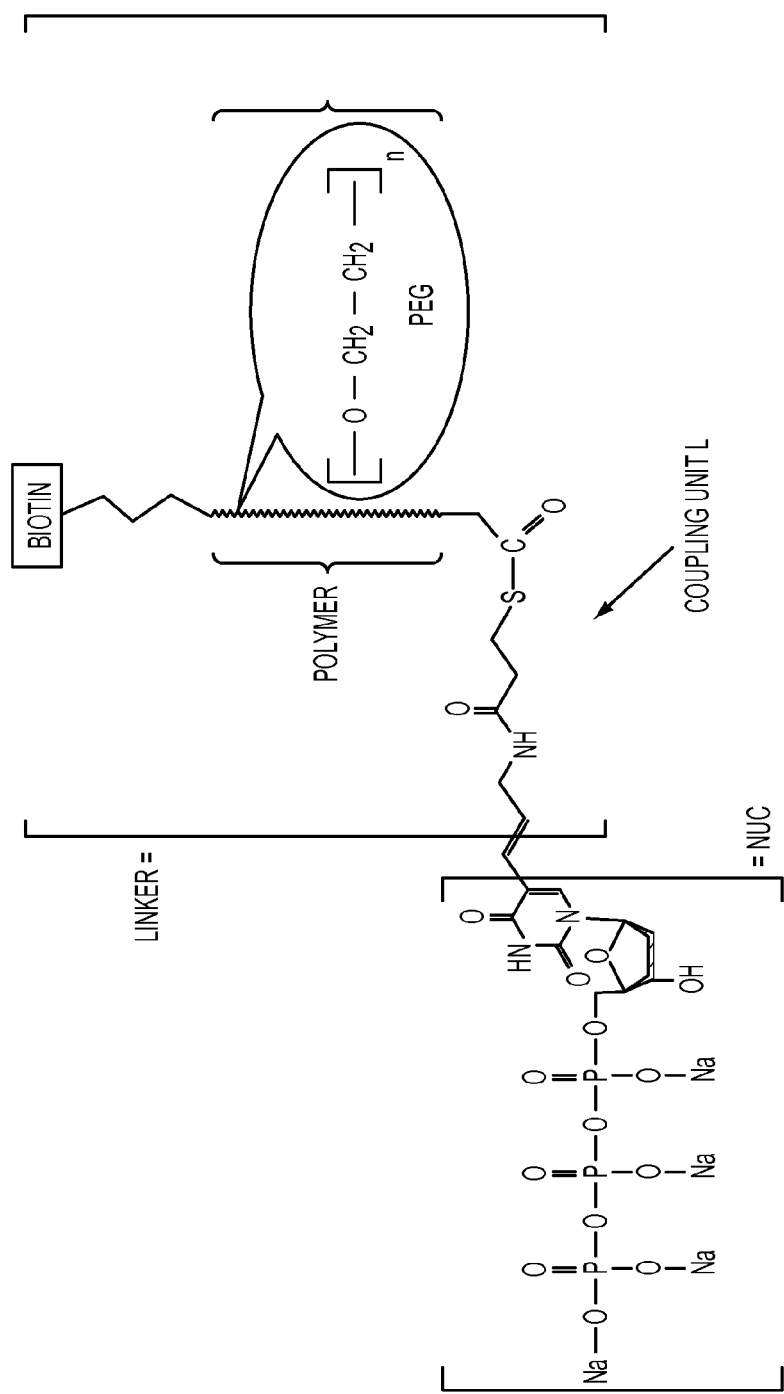
FIG. 31B is dUTP-AA-Propionate-S—CO-PEG-Biotin, as described in Example 23.

The linker component can be cleaved off simultaneously with the marker component under mild conditions. This can be advantageous for methods like sequencing by synthesis (Balasubramanian WO 03048387, Tcherkassov WO 02088382, Quake WO0132930, Kartalov WO02072892), where removal of the marker is necessary after each detection step.

dUTP-AA-Propionate-S—CO-PEG-Biotin (FIG. 31B) represents a further example of nuc-macromolecules with a group cleavable under mild conditions. For this synthesis, dUTP-AA-PDTP was freshly purified with an RP-HPLC in water-methanol gradient.

A solution of TCEP (20 µl 100 mmol/l A, pH 8) was added to an aqueous solution of dUTP-AA-PDTP (10 µl, 50 mmol/l). The reaction was allowed to proceed for 10 min at RT. The product of the reaction, dUTP-AA-Propionate-SH, was separated from other reagents on preparative TLC plates, LM 2. Under these conditions the product remains on the start line. It was eluted from the plate with water and dried and dissolved in 50 µl 50 mmol/l borate buffer pH 8. To the solution obtained, a freshly prepared 2% (w/v) aqueous solution of Biotin-PEG-NHS (50 µl) was added. The reaction was allowed to proceed for 30 min at RT. On completion, the product of the reaction, dUTP-AA-Propionate-S—CO-PEG-Biotin, was separated from the low molecular weight compounds by ultrafiltration, MWCO 3000, and washed five times with 0.5 ml water and, after the last step, dissolved in 50 µl.

The dUTP-AA-Propionate-S—CO-PEG-Biotin obtained by these means can be used by DNA Polymerases, for Instance, Klenow fragment Exo-minus or Taq polymerase, for Incorporation into the growing strand of nucleic acids.

Further marker components can be coupled to the biotin via streptavidin.

The dUTP-AA-Propionate-S—CO-PEG-Biotin contains a group cleavable under mild conditions, so that the linker with the dye can be cleaved off from the nucleotide. This is of particular interest, for instance, in processes of sequencing by synthesis (Balasubramanian WO 03048387, Tcherkassov WO 02088382, Quake WO0132930, Kartalov WO02072892).

This example shows the general possibility of further nucleotide modifications. Further base-modified nucleotide analogs, e.g., 5-propargylamino-dCTP, 5-amino-propargyl-dUTP, 7-deaza-aminopropargyl-dGTP and 7-deaza-aminopropargyl-dATP can also be modified in a similar way. Ribonucleotides, 2'-deoxyribonucleotides as well as 2',3'-Dideoxyribonudetides can be used (FIGS. 11 to 14).

Example 24

TTP-O-Propionate-SS-PEG-Biotin

A solution of bis-dithio-ethyl-PEG-biotin (100 µl, 0.5 mmol/l, in water) was added to 100 µl of solution of TTP-O-Propionat-SH, 10 mmol/l, in 50 mmol/l borate buffer, pH 9.5, and stirred for 24 h at RT. The purification was done by ultrafiltration with 3,000 MWCO as in example 19.

Examples of the coupling of amino groups to the phosphate residues of nucleotides are described in D. Jameson et al. Methods in Enzymology 1997, v. 278, p. 363. To this amino group a linker component can be coupled. Examples of coupling of linkers to phosphate groups of nucleotides are shown in U.S. Pat. No. 5,981,507. To such a linker further macromolecular linkers comprising a low molecular marker or a low molecular coupling unit or a macromolecular marker can be coupled.

In one embodiment, the macromolecular linker is attached to the phosphate groups, which are coupled to the 5' position of the ribose. The coupling is done preferably to the gamma phosphate group of the nucleotide, whereby ribonucleotides, as well as 2'-deoxyribonucleotides and 2',3-'dideoxyribonucleotides can be used.

In another embodiment, the macromolecular linker is coupled to the 3'-phosphate group of a 5'-nucleoside triphosphate.

Coupling of Marker Components

Example 25

(dUTP-16 Biotin)4-SA,

A solution of streptavidin (200 µl, 1 mg/ml, in 50 mmol/l Tris-HCl, pH 8.0) was added to a solution of Biotin-16-dUTP (200 µl, 200 µmol/l, in 50 mmol/l Tris-HCl, pH 8.0). After 1 hour at RT, the (dUTP-16 Biotin)4-SA was separated from non-reacted Biotin-16-dUTP by ultrafiltration, 50,000 MWCO.

A compound was obtained which displays both a nucleotide functionality and a macromolecular marker functionality. It can be considered as a representative example of conventionally modified nucleotides with a macromolecular marker.

This compound is not accepted by polymerases (e.g., Klenow-Exo-minus polymerase and terminal transferase) as a substrate. The modification leads to the loss of substrate properties (see example 34B).

Properties of the biotin streptavidin linkage are described in, e.g Gonzalez et al. Journal Biolog. Chem. 1997, v. 272, p. 11288.

Example 26

(dUTP-16-Biotin)4-SA-Cy2,

The coupling of dUTP-16-Biotin to SA-CY2 was carried out as described for (dUTP-16 Biotin)4-SA.

This compound acts as an equivalent to the compound described in example 25, in which streptavidin has fluorescent labeling for the purpose of visualisation.

Example 27 dCTP-PA-SS-Oligo-dT30,

Synthesis was conducted as described for dUTP-AA-SS-MEA-Cy3. To dCTP-PA-PDTP (100 µl, 20 mmol/l), Oligo-dT30-3'-SH (MWG-Biotech), (SEQ ID NO: 11 was added (final concentration 200 µmol/l) and was stirred for 18 h at RT, pH 9. Separation was accomplished by ultrafiltration with 3,000 MWCO.

This compound is not accepted by polymerases (e.g., Klenow Exo-minus polymerase and terminal transferase) as a substrate. The modification of the nucleotide part leads to abolition of the substrate properties.

Example 28

Figure 32:
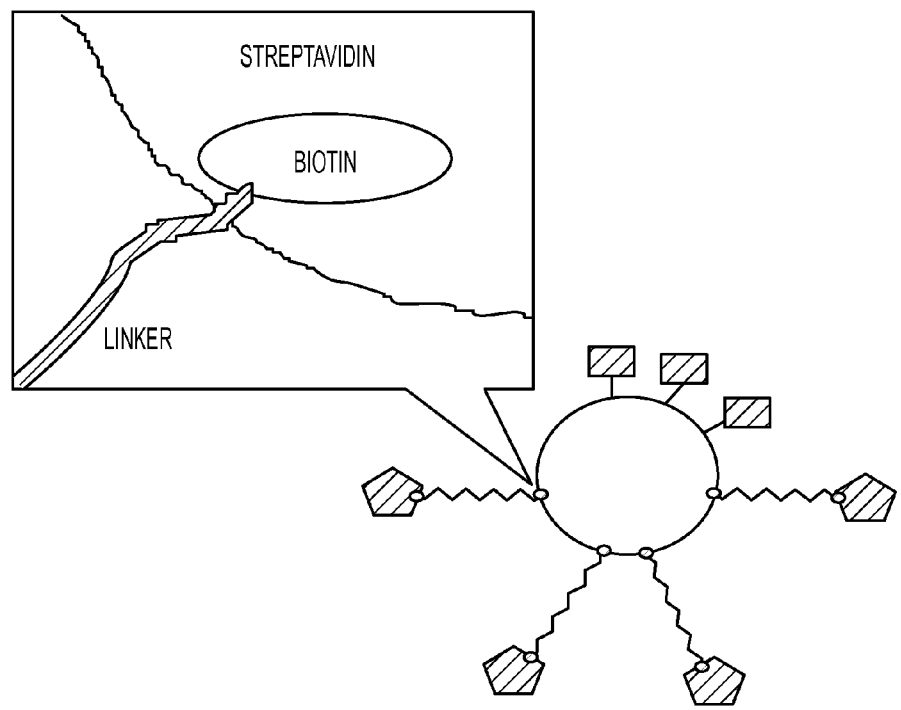
FIG. 32 is (dUTP-AA-PEG-Biotin)4-SA-Cy2 and (dUTP-AA-PEG-Biotin)4-SA, as described in Example 28.
Figure 32:
Figure 32:
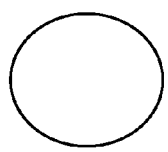
Figure 32:
Figure 32:
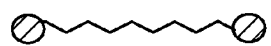

(dUTP-AA-PEG-Biotin)4-SA-Cy2 and (dUTP-AA-PEG-Biotin)4-SA, FIG. 32

The coupling of dUTP-AA-PEG-Biotin to SA-CY2 or to SA was carried out as described for (dUTP-16 Biotin)4-SA. To streptavidin (200 µl, 1 µg/µl) a solution of dUTP-AA-PEG-Biotin (approx. 1 mmol/l, 10 µl) was added and stirred at RT for 1 h. Then the product was separated by ultrafiltration, 50,000 MWCO, from the non-coupled dUTP-AA-PEG-Biotin and the product was washed two times with water.

A part of the (dUTP-AA-PEG-Biotin)4-SA-Cy2 obtained was modified with Cy3-NHS: (dUTP-AA-PEG-Biotin)4-SA-Cy2 (50 µl) was dissolved in 50 mmol/l borate, pH 8.5, up to a concentration of 1.4 µg/µl, and after that Cy3-NHS was added. The final concentration of Cy3 amounted to 10 mmol/l. The reaction was carried out for 1 h at RT. The product, (dUTP-AA-PEG-Biotin)4-SA-Cy2/Cy3, was separated by ultrafiltration with 30,000 MWCO.

Thereby, a nuc-macromolecule was produced that comprises very few free amino groups on the marker part.

A compound was obtained which comprises a nucleotide functionality, a long macromolecular linker and a macromolecular marker component. It can be considered as a representative example of nuc-macromolecules.

This compound is accepted by polymerases (e.g., Klenow Exo-minus polymerase and terminal transferase) as a substrate (see examples 34, 35).

Other compounds having a long linker and comprising a biotin molecule can also be used similarly in synthesis (see examples 20, 22, 23, 24).

Example 29

Figure 33:
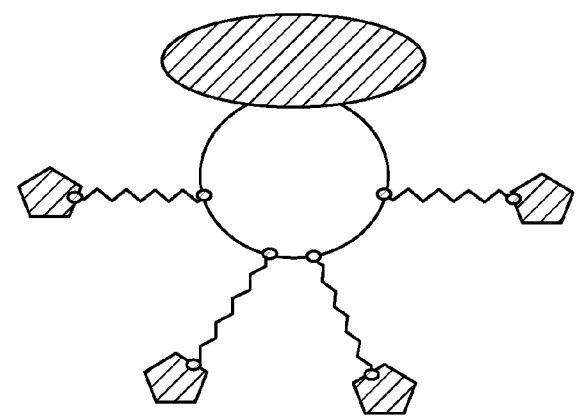
FIG. 33 shows (dUTP-AA-PEG-Biotin)4-SA-Alkaline Phosphatase, as described in Example 29.
Figure 33:
Figure 33:
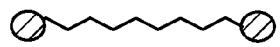
Figure 33:
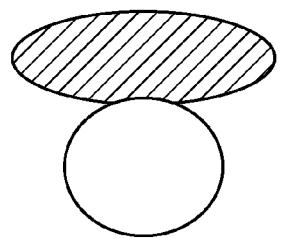
Figure 34:
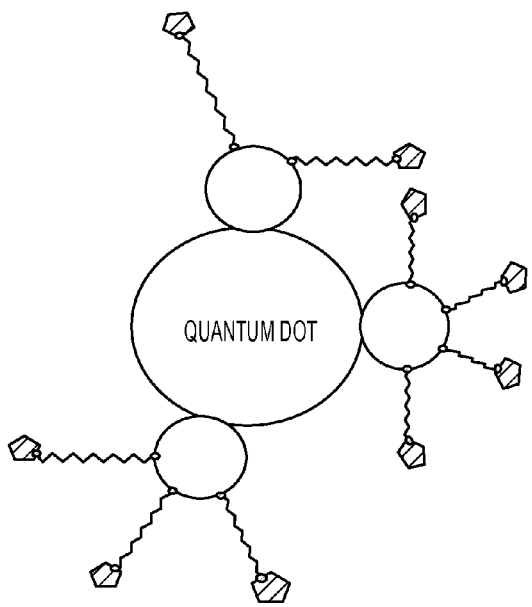
FIG. 34 shows (dUTP-AA-PEG-Biotin)4-SA-QDot, as described in Example 29.
Figure 34:
Figure 34:
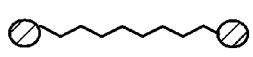
Figure 34:
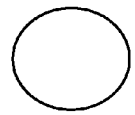

(dUTP-AA-PEG-Biotin)4-SA-Alkaline Phosphatase (FIG. 33) and (dUTP-AA-PEG-Biotin)4-SA-QDot (FIG. 34).

The coupling of dUTP-AA-PEG-Biotin to SA-AP or QDot was carried out as described for (dUTP-16 Biotin)4-SA.

In the case of QDot, nuc-linker parts are arranged on the surface of the QDots.

A compound was obtained which comprises a nucleotide functionality, a long macromolecular linker and a macromolecular marker component with an enzyme or Q-Dots.

This compound is accepted by polymerases (e.g., Klenow Exominus polymerase and terminal transferase) as a substrate.

Other compounds that have a long linker and comprise a biotin molecule can also be used similarly in synthesis (see examples 20, 22, 23, 24).

Example 30

Figure 35:
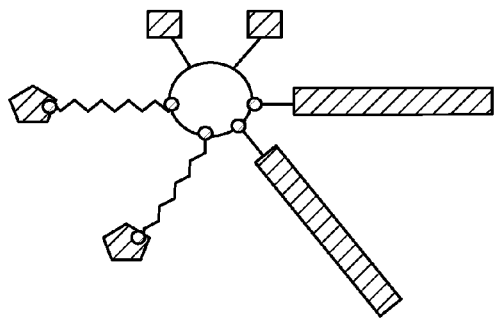
FIG. 35A shows (dUTP-AA-PEG-Biotin)2-(dT31-TEG-Biotin)2-SA-CY2, as described in Example 30.
FIG. 35(B) shows an embodiment of the invention in which complementary nucleic acids, having a signal-giving function, are hybridized to an oligonucleotide such as oligo-dT31, which consists of nucleoside monophosphates that do not participate in the enzymatic reaction and have only a signal-transmitting function.
Figure 35:
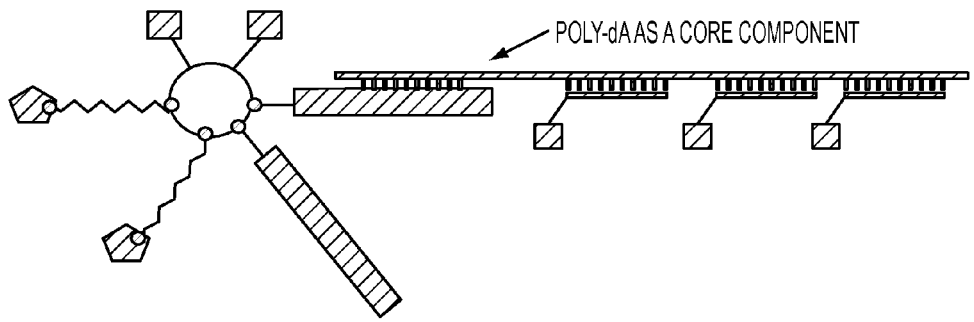
Figure 35:
Figure 35:
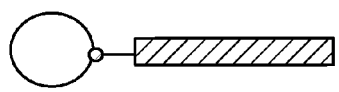
Figure 35:
Figure 35:
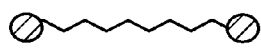
Figure 35:
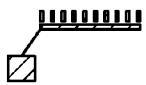

(dUTP-AA-PEG-Biotin)2-(dT31-TEG-Biotin)2-SA-CY2, FIG. 35A dT31-3'-TEG-biotin (MWG Biotech), SEQ ID NO: 10, The coupling of dUTP-AA-PEG-biotin to SA-CY2 was carried out like described for (dUTP-16-biotin)4-SA: dT31-3'-TEG-biotin (MWG Biotech) (80 µl, 80 µmol/l) was added to 100 µl of a solution of streptavidin-Cy2 (20 µmol/l, 1.2 mg/ml, in Tris-HCl, 50 mmol/l, pH 8) and incubated for 10 min at RT. (TEG is a short linker between biotin and dT31). Then, a solution dUTP-AA-PEG-biotin (100 µl, 50 µmol/l, in 50 mmol/l Tris-HCl, pH 8.0) was added. After 10 min at RT, (dUTP-AA-PEG-biotin)2-(dT31-TEG-biotin)2-SA-CY2 was purified by ultrafiltration, 50,000 MWCO.

The substance comprises a nucleoside triphosphate functionality and macromolecular marker functionalities (oligo-dT31). The oligo-dT31 consists of nucleoside monophosphates, which, however, are not participating in the enzymatic reaction and have only a signal-transmitting function. Complementary nucleic acids, having a signal-giving function, can be hybridized to such an oligonucleotide (FIG. 35B). (General rules for hybridization of nucleic chains are known to the person skilled in the art, Anderson "Nucleic Acid Hybridization", 1999).

Polymerases (e.g., Klenow-exo minus polymerase and terminal transferase) accept this compound as a substrate.

This derivative can be coupled, for instance, to poly-dA (SEQ ID NO: 6) or poly-A (e.g., with a medium length of 260 NTs, Amersham Bioscience) by hybridization. One single as well as several (dUTP-AA-PEG-biotin)2-(dT31-biotin)2-SA-CY2 molecules can be coupled to a poly-dA molecule, see FIG. 5. The ratio is determined by the concentration ratios. Other oligonucleotides, such as oligonucleotides labeled with dyes, can also be coupled together with (dUTP-AA-PEG-biotin)2-(dT31-biotin)2-SA-CY2 to the same strand of the poly-dA or poly-A, wherein the ratios between various molecules are variable. Thus, it is possible to produce a polyfunctional nuc-macromolecule. A major advantage of such a nuc-macromolecule consists of easily cleavable macromolecular labeling: labeled oligonucleotides hybridized to poly-dA or poly-A strands can be detached via denaturation. The Tm of these oligonucleotides can be adjusted by an appropriate choice of the length of the labeled oligonucleotides for the respective requirements of the reversible labeling. The rules for the Tm calculation are known to the person skilled in the art ("Molecular-Cloning", J. Sambrook, Vols. 1-3, 2001). For instance, $dT_{25}$-oligonucleotides labeled with a Cy3-molecule can be coupled to the poly-dA.

By using RNA, e.g. poly-A for the bonding of several (dUTP-AA-PEG-biotin)2-(dT31-biotin)2-SA, the cleavage can be accomplished by an RNase.

Because streptavidin has 4 binding sites for biotin, the result is a mixture of nuc-macromolecules in which the 4 binding sites are differently occupied. This mixture can be separated by different means. One possibility consists of isolating nuc-macromolecules that carry at least one oligo-dT31, by absorption on an anion exchanger (e.g., a DEAE cellulose column) for example. Gel electrophoresis is also suitable for separating single derivatives.

Longer nucleic acid chains comprising a biotin molecule such as poly-dA-biotin, produced by a terminal coupling of ddUTP-18-biotin in a TdT-dependent reaction ("Molecular-Cloning", J. Sambrook, Vols. 1-3, 2001) for example, can be coupled to the streptavidin in a similar manner, so that molecules with an average composition of (dUTP-AA-PEG-biotin)$_{N}$-(nucleic acid chains-biotin)$_{M}$-SA are produced. Single-stranded as well as double-stranded nucleic acid chains can be coupled. The length of the coupled nucleic acid chains can range between 10 and 100, 100 and 1000 nucleotides.

The hybridized oligonucleotides carrying a dye can also be covalently bonded to the poly-dA strand by crosslinking.

Also other compounds having a long linker and comprising a biotin molecule can similarly be used in the synthesis, see Examples 20, 22, 23, 24.

Figure 36:
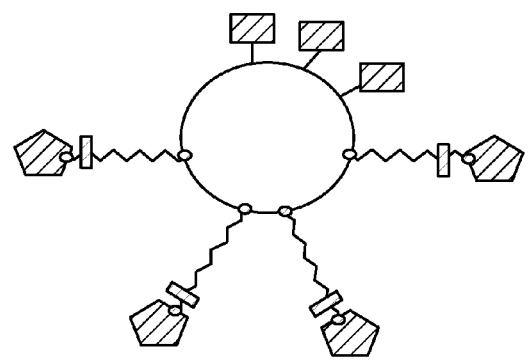
FIG. 36 shows (dUTP-AA-SS-PEG-Biotin)4-SA and (dUTP-AA-SS-PEG-Biotin)4-SA-Cy2, as described in Example 31 A.
Figure 36:
Figure 36:
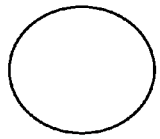
Figure 36:
Figure 36:
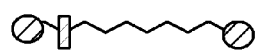

Example 31A (dUTP-AA-SS-PEG-Biotin)4-SA and (dUTP-AA-SS-PEG-Biotin)4-SA-Cy2, FIG. 36

The coupling of dUTP-AA-SS-PEG-biotin to SA or to SA-CY2 was carried out as described for (dUTP-AA-PEG-biotin)4-SA. Streptavidin and dUTP-AA-SS-PEG-biotin were used as educts.

The obtained compound comprises a nucleotide functionality, a long macromolecular linker and a macromolecular marker component. The linker component and the marker component can be cleaved from the nuc-component under mild conditions.

The product can be considered representative for nuc-macromolecules carrying a bond in the linker component cleavable under mild conditions.

Polymerases (e.g., Klenow-exo minus polymerase and terminal transferase) accept this compound as a substrate, see Example 34.

Example 31B (dGTP-PA-SS-PEG-Biotin) 4-SA

A solution of streptavidin (200 µl, 50 µmol/l, in 50 mmol/l borate buffer, pH 9) was incubated with 5 equivalents of biotin-PEG-PDTP (PEG linker 30 atoms; for synthesis, see example 4) for 10 minutes. Streptavidin-(biotin-PEG-PDTP)4 was separated from low-molecular-weight components via ultrafiltration with a 30 kDa MWCO filter by repeated washings with borate buffer. A solution of TCEP (100 µl, 10 mmol/l, pH 8) was added to the solution of streptavidin-(biotin-PEG-PDTP)4 (200 µl, 50 µmol/l) in borate buffer. After 30 min, streptavidin-(biotin-PEG-R—SH)4 was again separated from low-molecular-weight components via ultrafiltration on 30 kDa MWCO by repeated washings with borate buffer.

dGTP-PA was modified with PDTP-NHS as described in example 1; the product is dGTP-PA-PDTP. A solution of dGTP-PA-PDTP (50 µl, 100 mmol/l, in 50 mmol/l borate buffer, pH 9) was added to the solution of streptavidin-(biotin-PEG-R—SH)4 (200 µl, 50 µmol/l, in 50 mmol/l borate buffer). After 30 min at RT, macromolecular products, including (dGTP-PA-SS-PEG-biotin)4—SA, were separated from low-molecular-weight components via ultrafiltration on 30 kDa MWCO by repeated washings with borate buffer.

The resulting product (dGTP-PA-SS-PEG-biotin)4-SA has a linker of 42 atoms between the nuc-component and the biotin. This nuc-macromolecule has a cleavable SS-bond in its linker and can be incorporated into a nucleic acid chain by Klenow fragment.

Figure 3:
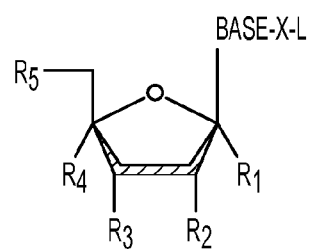
FIG. 3A and FIG. 3B show modified nucleotides of the invention comprising base-, sugar- or phosphate-modified nucleotide analogs.
Figure 3:
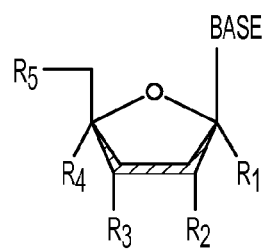
Figure 37:
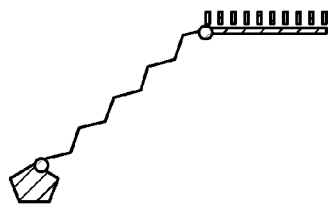
FIG. 37A is dCTP-PA-PEG-Maleimide-5-Oligo-dT30.
FIG. 37B shows an embodiment in which complementary nucleic acids having a signal-giving function can be hybridized to an oligonucleotide such as oligo dT-30.
FIG. 37C shows that by adding poly-dA or poly-A, it is possible to couple several dCTP-PA-PEG-maleimide-S-oligo-dT30 molecules, e.g., 10 to 20, to one nuc-macromolecule to obtain a nuc-macromolecule with linearly arranged nuc-linker components.
Figure 37:
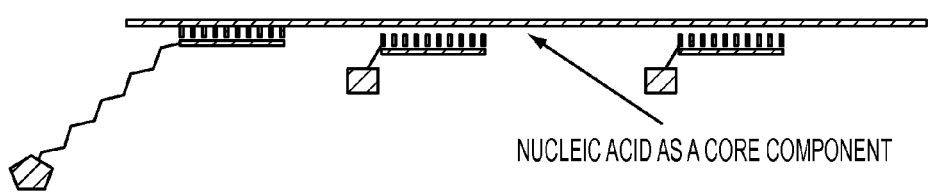
Figure 37:
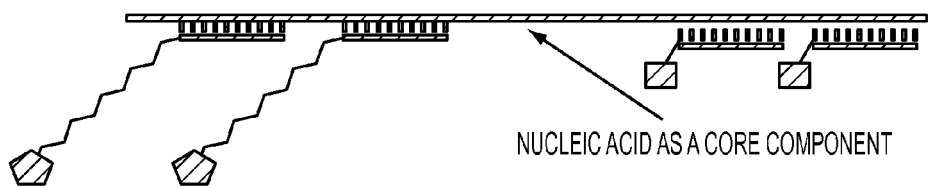
Figure 37:
Figure 37:
Figure 37:
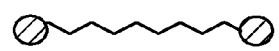

Example 32 dCTP-PA-PEG-maleimide-S-oligo-dT30, FIG. 37A
3'-SH-oligo-dT30, (SEQ ID NO: 11)

A solution of 3'-SH-oligo-dT30 (100 µl, 200 µmol/l, in water) was added into a solution of dCTP-PA-PEG-maleimide (100 µl, 5 mmol/l, in 50 mmol/l borate buffer, pH 9.5) and stirred at RT for 48 h. The product was cleaned by means of preparative gel electrophoresis, 12% polyacrylamide gel.

The substance comprises a nucleoside triphosphate functionality and macromolecular marker functionalities (oligo-dT30). The oligo-dT30 consists of nucleotides which do not take part, however, in the enzymatic reaction and have only a signal-transmitting function. Complementary nucleic acids having a signal-giving function can be hybridized to such an oligonucleotide (FIG. 37B). (General rules for the hybridization of nucleic acids are known to the person skilled in the art, Anderson "Nucleic Add Hybridization", 1999).

Polymerases (e.g., Klenow-exo minus polymerase and terminal transferase) accept this compound as a substrate.

This example shows a general possibility for making further modifications to nucleotides. Other base-modified nucleotide analogs, e.g., 5-allylamino-dUTP, 5-amino-propargyl-dUTP, 7-deaza-aminopropargyl-dGTP and 7-deaza-aminopropargyl-dATP can be also modified as described above. Ribonucleotides, 2'-deoxyribonucleotides as well as 2',3'-dideoxyribonucleotides can be used, FIGS. 11 to 14.

By adding poly-dA (SEQ ID NO: 6) or poly-A, it is possible to couple several dCTP-PA-PEG-maleimide-S-oligo-dT30 molecules, e.g., 10 to 20, to one nuc-macromolecule. A nuc-macromolecule with linearly arranged nuc-linker components is thereby obtained (FIG. 37C).

Example 33

(dCTP-PA-PEG-Maleimide-S)n-Polylysine-(Cy3)m,

Educts: dCTP-PA-PEG-maleimide
(HS-propionate)m-polylysine-(Cy3) n, n=10 to 15, m=3 to 9, polylysine 10,000-20,000

A solution of (HS-propionate)m-polylysine-(Cy3)n (20 µl, approx. 1 mmol/l, in water) was added to a solution of dCTP-PA-PEG-maleimide (100 µl, 5 mmol/l, in 50 mmol/l borate buffer, pH 9.5) and stirred at 40° C. for 18 h. The product was purified by ultrafiltration, 30,000 MWCO.

The obtained compound comprises a nucleotide functionality, a long macromolecular linker and a macromolecular marker component. Several nuc-components are coupled per each nuc-macromolecule. Polymerases (e.g., Klenow-exo minus polymerase and terminal transferase) accept this compound as a substrate.

Other combinations of nuc-components, linker components and marker components are obvious to the person skilled in the art.

Comparison of Substrate Properties of Some Representatives of Nuc-Macromolecules with Conventionally Modified Nucleotides.

Substrate properties of the nuc-macromolecules for polymerases and terminal deoxy-nucleotidyl-transferase (TdT) were compared to the properties of the conventionally modified nucleotides in a labeling reaction. General principles of labeling reactions are shown in "Molecular-Cloning", J. Sambrook, Vols. 1-3, 2001, ISBN 0-87969-576-5.

Example 34

Substrate Properties of Nuc-Macromolecules or Conventionally Modified Nucleotides Towards Polymerases This example is not intended to limit the possible labeling reactions, but merely to point out differences in the substrate properties.

Both self-synthesized and commercially available modified nucleotides dUTP-Cy3 (Amersham) and dUTP-16 biotin (Roche) were used in the reactions. Unmodified dNTPs (dATP, dGTP, dTTP, dCTP) were purchased from Roth.

Both short oligonucleotides and poly-dA acted as templates. Primers and oligonucleotides were synthesized by MWG Biotech.

Reactions were carried out in 20 mmol/l of Tris buffer, pH 8.5, 5 mmol/l $MgCl_2$, 10% glycerin. The concentrations of the primers amounted to 1 µmol/l, of the oligonucleotides, 1 µmol/l, and the concentration of poly-dA was 0.1 µg/µl (for the concentration ratios for the solid phase, see below). Klenow exo minus was used a polymerase (Amersham) at concentration of 1 Unit/100 µl. The concentrations of nucleotides amounted to 20 µmol/l for conventionally modified nucleotides and 5 µmol/l for nuc-macromolecules. Unmodified nucleotides were used in concentrations of 50 µmol/l.

First, primers were hybridized to the respective template: The reaction mixture without polymerase was heated up to 75° C. and was cooled down to 37° C. over 5 min. Then, the polymerase was added. All reactions were carried out at 37° C. for 1 h. The reactions were stopped by adding EDTA (final concentration 10 mmol/l).

After the reaction had stopped, streptavidin was added to some reaction mixtures up to a final concentration of 1 mg/ml and the reaction mixture was incubated at 37° C. for another 10 min. The already-incorporated nucleotides comprising biotin can thereby react with streptavidin and thereby link streptavidin and oligonucleotide. These experiments are suitable as a control for the mobility properties of modified primers.

Mercaptoethanol was added to the designated reaction mixtures (up to 20 mmol/l final concentration) and the respective mixtures were incubated at 37° C. for 10 min. For some mixtures, mercaptoethanol was added during the reaction and, for others, after the reaction.

The reaction was analyzed by means of denaturing gel electrophoresis, 20% polyacrylamide-gel, 50 mmol/l Tris-HCl, pH 8.7, as described in "Gel electrophoresis of nucleic Acids", Ed. D. Rickwood, 1990. For the denaturing of the samples, a higher temperature, rather than 7 M urea, was used during the gel electrophoresis (60° C.). The electrophoresis was carried out in BioRad gel chambers (Protean 3), at 200 V, for approx. 1 h. The visualization was performed using the UV-vis gel-documentation equipment (BioRad).

Figure 38:
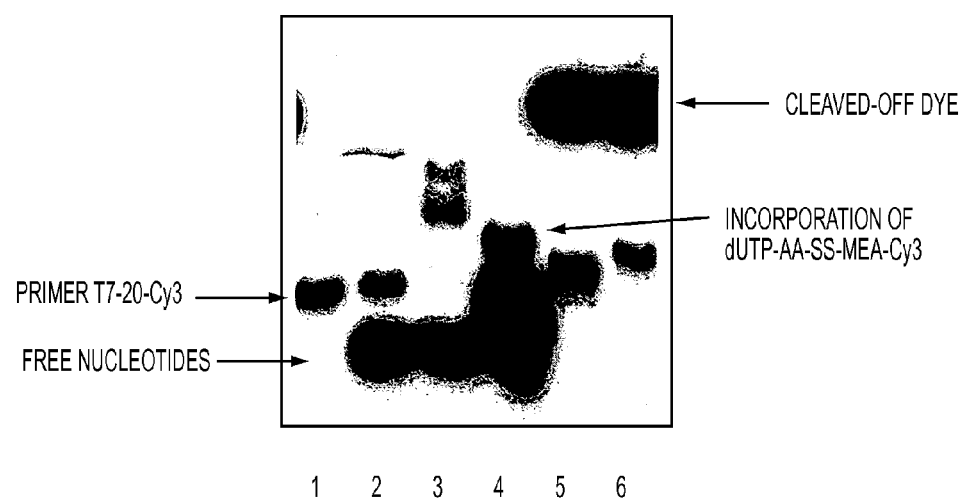
FIG. 38 illustrates the incorporation and cleavage of a conventionally modified nucleotide (dUTP-AA-SS-MEA-Cy3).

Example 34A, FIG. 38

Illustration of the Incorporation and Cleavage of a Conventionally Modified Nucleotide (dUTP-AA-SS-MEA-Cy3)

Sequences:

```
Primer-T7-20-5'-Cy3:
5'-Cy3-TAATACGACTCACTATAGGG-3' (SEQ ID NO. 1)

Template:
Oligonucleotide
Oligo 1:
5'-AGTTTTAGTTTTACCCTATAGTGAGTCGTATTA-3', (SEQ ID NO. 2)
```

The primer binding site is underlined.
Legend:
Traces 1-6:
1) Only PrimerT7-20-Cy3+Oligo 1
2) PrimerT7-20-Cy3+Oligo 1+dCTP-Cy3+dATP+dGTP+polymerase
3) PrimerT7-20-Cy3+Oligo 1+dCTP-Cy3+dATP+dGTP+dTTP+polymerase
4) PrimerT7-20-Cy3+Oligo 1+dUTP-AA-SS-MEA-Cy3+polymerase
5) After 1 h, mercaptoethanol was added to an aliquot of the reaction mixture 4 and incubated for another 10 min. This resulted in a cleavage of the labeling.
6) After 10 min, dGTP was added to an aliquot of the reaction mixture 5 dATP and incubated at 37° C. for 30 min.

As can be seen, dUTP-AA-SS-MEA-Cy3 is incorporated by the polymerase (trace 4). The dye can be cleaved off from the primer (trace 5) (as can be seen, the band is shifted because of the smaller size of the oligonucleotide). Finally, other nucleotides can be incorporated (trace 6).

A reaction mixture with dUTP-AA-SS-TEAE-(Cy3)2, carried out in a similar way, did not result in incorporation of the nucleotide analogs into the primer.

This example shows that the even slight changes in the analog structure, for instance, doubling the number of the dyes which are coupled to a nucleotide, can change the substrate properties of the nucleotides.

Figure 39:
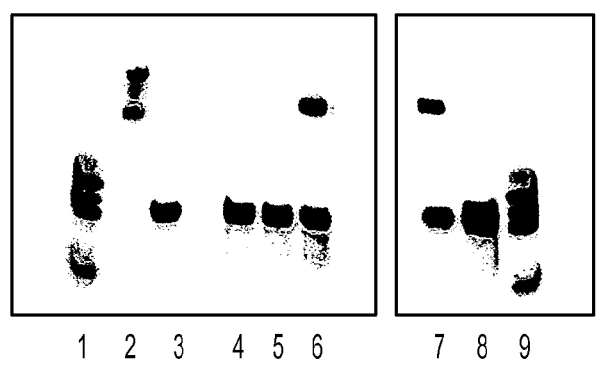
FIG. 39 shows a comparison of substrate properties of a conventionally modified nucleotide with a macromolecular marker and a Nuc-Macromolecule, as described in Example 34B.

Example 34B, FIG. 39

Comparison of Substrate Properties of a Conventionally Modified Nucleotide with a Macromolecular Marker and a Nuc-Macromolecule Sequences:

```
Primer:
Primer-dT35-5'-Cy3 (dT35-Cy3):
5'Cy3-TTTTTTTTTTTTTTTTTTTTTTTTTTTTTTTTTTT-3', (SEQ ID NO. 3)
```

Template:
Poly-dA (Amersham), SEQ ID NO: 6, average length 270 nucleotides.
Nucleotides: (dUTP-AA-SS-PEG-biotin)4-SA, (dUTP-16-biotin)4-SA, dUTP-16-biotin
Legend:
Traces 1-9:
1) Ladder: T-7-20-Cy3, SEQ ID NO: 1,
dT35-Cy3, SEQ ID NO: 3,
dT40-Cy3, SEQ ID NO: 4,
dT50-Cy3, SEQ ID NO: 5,
2) (dUTP-AA-SS-PEG-biotin)4-SA+dT35-Cy3+poly-dA+polymerase
3) (dUTP-AA-SS-PEG-biotin)4-SA+dT35-Cy3+poly-dA
4) (dUTP-16-biotin)4-SA+dT35-Cy3+poly-dA+polymerase
5) (dUTP-16-biotin)4-SA+dT35-Cy3+poly-dA
6) (dUTP-16-biotin)4-SA-Cy3+dT35-Cy3+poly-dA Control reaction mixture, traces 7-9:
7) dUTP-16-biotin+dT35-Cy3+poly-dA+polymerase, incubation at 37° C. for 1 h followed by +EDTA to 10 mmol/l final concentration, followed by +Streptavidin, 37° C., 10 min
8) dUTP-16-biotin+dT35-Cy3+poly-dA+polymerase, incubation at 37° C. for 1 h followed by +EDTA to 10 mmol/l final concentration,
9) Ladder: T-7-20-Cy3, dT35-Cy3, dT40-Cy3, dT50-Cy3

A nuc-macromolecule, (dUTP-AA-SS-PEG-biotin)4-SA, is incorporated into the primer (trace 2). After the nuc-macromolecule has been incorporated, the electrophoretic mobility of the labeled primer is greatly changed. Mere presence of nuc-macromolecules has no influence on the primer (trace 3).

A conventionally modified nucleotide, (dUTP-16-biotin) 4-SA, with a macromolecular marker, is not incorporate into the primer (trace 4). In spite of the presence of the polymerase in reaction 4 (trace 4), no differences can be observed between trace 4 and trace 5.

Trace 6 shows the position of the conventionally modified nucleotide with a macromolecular marker, (dUTP-16-biotin) 4-SA-Cy3 (the upper band), and the position of the labeled primer (the lower band).

Trace 7 shows the result of incorporating dUTP-16-biotin followed by a reaction with the streptavidin: Primers labeled with biotin react with streptavidin and change their mobility properties. The unmodified primers maintain their electrophoretic properties.

Trace 8 shows the result of the incorporation reaction of a conventionally modified nucleotide, dUTP-16-biotin. A widened primer band, resulting from the incorporation of dUTP-16-biotin into the primer, can be seen. The extension of primers is limited, because dUTP-16-biotin cannot be successively incorporated indefinitely; an average of approx. 3 dUTP analogs are incorporated, so that the length of primer rises on average to 38 NTs. As expected, the incorporation of conventionally modified nucleotides with a low molecular marker does not lead to a strong change in the electrophoretic mobility of the primer.

In this experiment, properties of the nuc-macromolecules, (dUTP-AA-SS-PEG-biotin)4-SA were compared to those of the conventionally modified nucleotides. It can be clearly seen that the coupling of a macromolecular marker to a commercially obtained dUTP-16-biotin leads to total loss of the substrate properties of the nucleotides. However, polymerase is quite capable of inserting dUTP-16-biotin without macromolecular marker into the primer (traces 7 and 8). The coupling of streptavidin to the biotin after the incorporation reaction leads to the mentioned changes in primer properties.

In contrast, the polymerases can incorporate nuc-macromolecules (dUTP-AA-SS-PEG-biotin)4—SA into the primer without difficulty. The inventors attribute the appearance of several bands in the gel (3 bands) to a multiple incorporation of nuc-macromolecules into the primer.

Figure 40:
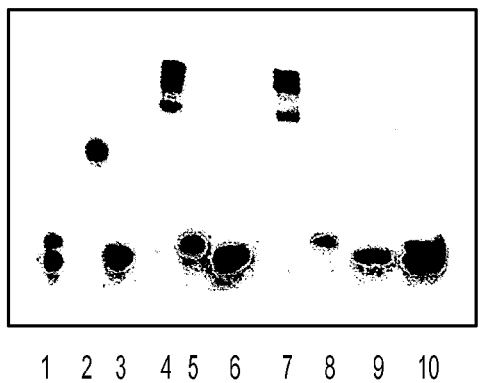
FIG. 40 shows a comparison of substrate properties of Nuc-Macromolecules, made by incorporation reactions in solution or on a solid phase, as described in Example 34C.

Example 34C, FIG. 40

Comparison of Substrate Properties of Nuc-Macromolecules, Incorporation Reaction in the Solution and on a Solid Phase Sequences:

```
Primer:
(dT35-Cy3), (SEQ ID NO: 3)

Primer-dT-35-5'-Cy3:
5'Cy3-TTTTTTTTTTTTTTTTTTTTTTTTTTTTTTTTTTT-3'
```

Template:
Poly-dA (Amersham), SEQ ID NO: 6, average length 270 nucleotides.
Oligo-dA50-3'-TEG-biotin (MWG Biotech), (SEQ ID NO: 7)
Nucleotides: (dUTP-AA-SS-PEG-biotin)4-SA, (dU-AA-PEG-biotin)4-SA Streptavidin polystyrene particles, 2.17μ, Spherotech Inc, Preparation of Streptavidin Polystyrene Particles (Solid Phase).

Three aliquots were prepared in the same way.

A solution with beads (0.5 ml in the manufacturer's buffer) was briefly centrifuged and bead-pellet was re-suspended in 100 μl of incorporation buffer (20 mmol/l Tris, pH 8.5, 5 mmol/l $MgCl_2$). Next, oligo-dA50-3'-TEG-biotin (100 μl, 50 μmol/l) was added and stirred at RT for 1 h. Oligo-dA molecules bind to the beads during this time. Next, the beads were briefly centrifuged and washed three times with the incorporation buffer. The final volume of the solid phase amounted 100 μl. This quantity of oligo-dA50-solid-phase can hybridize primer-dT-35-Cy3 (2 μmol/l).

The hybridization of primer-dT-35-Cy3 was undertaken for 10 min at 40° C., followed by cooling to RT within 10 min. All other steps were carried out in identical way for all aliquots.

Legend:
Traces 1-10:
1) Ladder: dT35-Cy3, dT40-Cy3,
Reactions in the Liquid Phase:
2) (dUTP-AA-PEG-biotin)4-SA+dT35-Cy3+poly-dA+polymerase
3) (dUTP-AA-PEG-biotin)4-SA+dT35-Cy3+poly-dA
4) (dUTP-AA-SS-PEG-biotin)4-SA+dT35-Cy3+poly-dA+polymerase, incubation at 37° C. for 1 h, then+EDTA
5) (dUTP-AA-SS-PEG-biotin)4-SA+dT35-Cy3+poly-dA+polymerase, incubation at 37° C. for 1 h, then+EDTA, followed by +Mercaptoethanol up to 200 mmol/l (final concentration) for 30 min.
6) (dUTP-AA-SS-PEG-biotin)4-SA+dT35-Cy3+Poly-dA+EDTA
Reactions on Solid Phase:
7) (dUTP-AA-SS-PEG-biotin)4-SA+dT35-Cy3+oligo-dA50-solid-phase+polymerase, incubation at 37° C. for 1 h, then+EDTA,
8) (dUTP-AA-SS-PEG-biotin)4-SA+dT35-Cy3+oligo-dA50-solid-phase+polymerase, incubation at 37° C. for 1 h, then+EDTA, followed by +mercaptoethanol up to 200 mmol/l (final concentration) for 30 min.
9) (dUTP-AA-SS-PEG-biotin)4-SA+dT35-Cy3+oligo-dA50 solid phase, prior to electrophoresis+EDTA
10) Ladder: dT35-Cy3, dT40-Cy3, The result of the incorporation reaction of nuc-macromolecules is clearly seen in traces 2, 4, 5, 7, 8. The enzymatic labeling reaction works well both in the solution and on the solid phase.

The cleavage of linker components with the bound streptavidin from the primers takes place after mercaptoethanol is added to reactions that have been stopped with EDTA. This leads to recovery of the electrophoretic properties of the primers. The shifting of the primer bands in traces 5 and 8 can be explained by multiple incorporation of nuc-macromolecules into the primer. In fact, the primer bands appear at the level of dT40-Cy3 (see ladder) following the cleavage. This means that up to 5 nuc-macromolecules were incorporated into the primer during the reaction.

Figure 41:
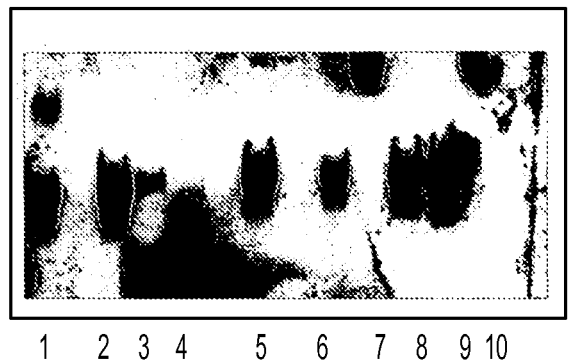
FIG. 41 shows the substrate properties of the Nuc-Macromolecules and conventionally modified nucleotides for Terminal Transferase (TDT), as described in Example 35.

Example 35, FIG. 41

Substrate Properties of the Nuc-Macromolecules and Conventionally Modified Nucleotides for Terminal Transferase (TDT)

The reaction was carried out according to the instructions of the kit manufacturer (Roche): For each 50 μl volume, the following was added: 10 µl 5× reaction buffer, 1 µl TdT (25 units), 5 µl 25 mmol/l CoCl2. The primer concentration and nucleotide concentrations were same as in reactions with the polymerase. The reaction was carried out at 37° C. for 2 h.

Primer: Primer-dT$_{35}$-5'-Cy3 (dT35-Cy3) SEQ ID NO : 3)
Primer-dT$_{35}$ (dT35) SEQ ID NO: 8).
Legend:
1) (dUTP-AA-PEG-biotin)4-SA+dT35-Cy3+TdT
2) (dUTP-AA-PEG-biotin)4-SA+dT35-Cy3
3) dUTP-Cy3 (Amersham)+dT35+TdT
4) dUTP-Cy3 (Amersham)+dT35
5) dUTP-16-biotin (Roche)+dT35-Cy3+TdT;
6) Mixture 5; after the stop+streptavidin
7) Streptavidin-Cy2
8) (dUTP-16-biotin)4-SA+dT35-Cy3+TdT
9) (dUTP-16-biotin)4-SA+dT35-Cy3
10) (dUTP-16-biotin)4-SA-Cy2

Two bands can clearly be seen in trace 1, the band in the middle corresponding to the dT35-Cy3, the upper band corresponding to the reaction product: nuc-macromolecule was incorporated into dT35 by TdT. Trace 2 is a negative control. In trace 3, it is possible to see the result of labeling dT35 with the conventional nucleotide dUTP-Cy3. Trace 4 is the negative control. In trace 5, the result of the coupling dUTP-16-biotin to the dT35-Cy3 can be poorly recognized. However, in trace 6, a weak band, which corresponds to the result of the reaction of the dUTP-16-biotin-modified primer with streptavidin, can be seen in the upper area. Trace 7 shows the position of the modified streptavidin. In traces 8 and 9, only one band, which corresponds to the dT35-Cy3, can be seen in the center of the gel; in the upper area of the gel, there is no visible band, clearly indicating that TdT does not incorporate conventionally modified nucleotides with a macromolecular marker. Trace 10 shows the position of the (dUTP-16 biotin) 4-SA-Cy2 in the gel.

Figure 42A:
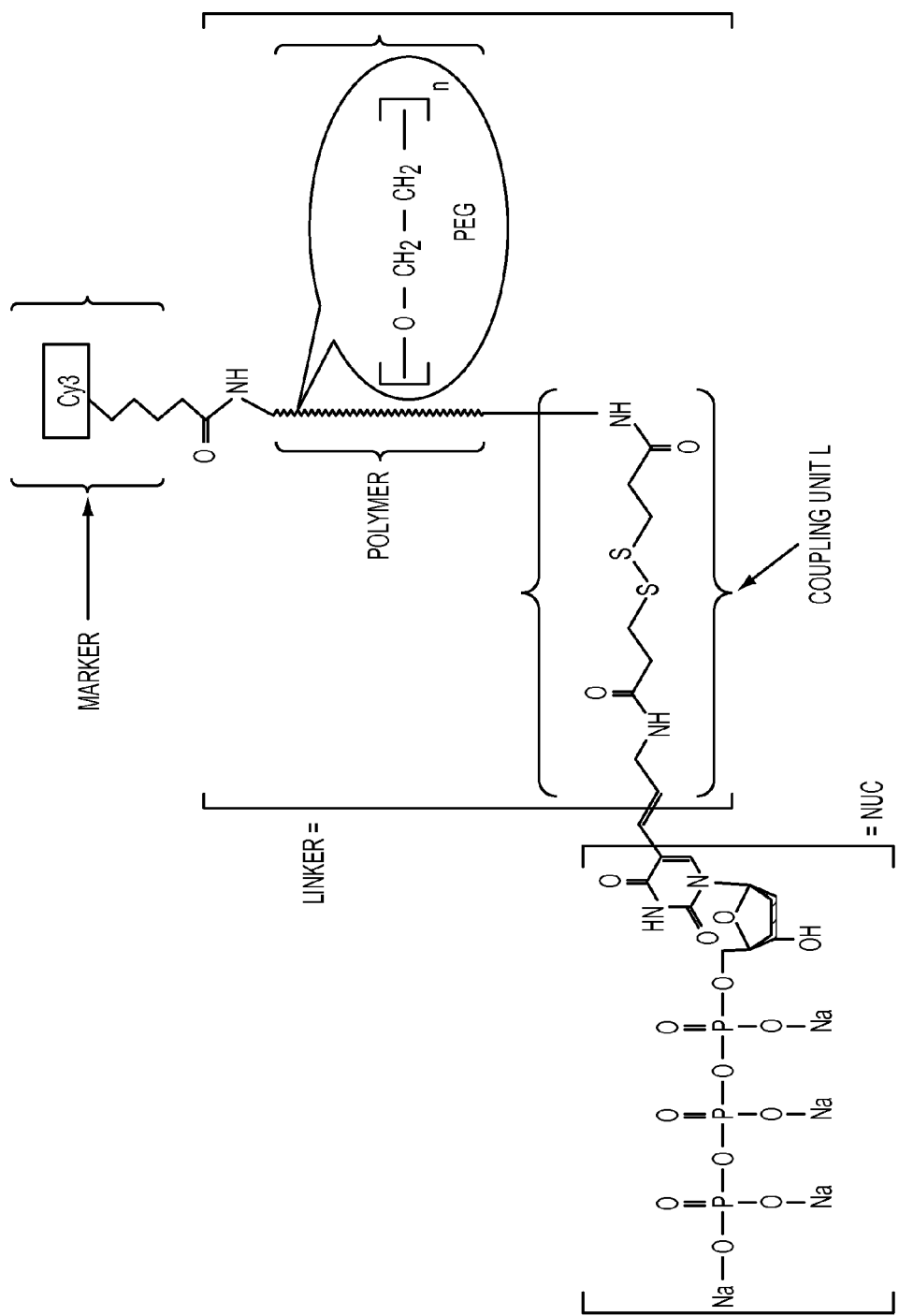
FIG. 42A shows dUTP-AA-SS-PEG-Cy3.

Example 36 dUTP-AA-SS-PEG-Cy3, FIG. 42A

Figure 42B:
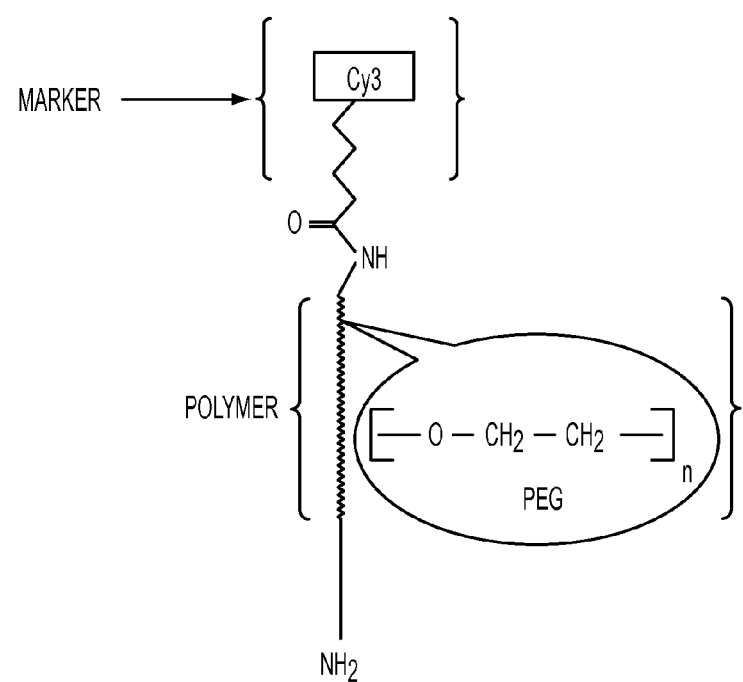
FIG. 42B shows an intermediate reaction product, as described in Example 36.

First, SH-PEG-Cy3 was synthesized. Cy3-NHS (Amersham-Bioscience) was added to a solution of diamine-PEG (6 kDa, Fluka) (200 µl, 10 mmol/l, in 50 mmol/l borate buffer, pH 8) up to final concentration of 15 mmol/l. The reaction was carried out at RT for 30 min. Next, NH$_2$—PEG-Cy3 (FIG. 42B) was separated from dye residues by ultrafiltration with MWCO 3000, washed 3 times with 1 ml 50 mmol/l borate buffer, pH 8, and dissolved in 200 µl of 50 mmol/l borate buffer, pH 8.

PDTP-NHS was added to this solution up to final concentration of 50 mmol/l. The reaction was carried out at RT for 30 min. Next, a solution of NH$_4$HCO$_3$ (50 µl, 1 mol/l, pH 8), was added, and the reaction mixture was incubated for another 60 min. A solution of TCEP (100 µl, 1 mol/l, pH 8) was added to the reaction mixture to reduce the disulfide bonds. After 5 min at RT, the product of the reaction, the SH-PEG-Cy3, was separated from the low-molecular compounds by ultrafiltration with MWCO 3000, was washed 5 times with 1 ml 50 mmol/l Tris-HCl buffer, pH 7, and dissolved in 200 µl of 50 mmol/l Tris-HCl, pH 7. The pH value was adjusted to 9.0 with 1 mol/l NaOH immediately before the coupling of the nucleotide part.

Coupling of the SH-PEG-Cy3 to the Nucleotide Part:

A solution of SH-PEG-Cy3 (100 µl, in 50 mmol/l Tris-HCl, pH 9.0) was added to 100 µl of 20 mmol/l dUTP-AA-PDTP in 50 mmol/l borate buffer, pH 9. The reaction was allowed to proceed at RT for more than 30 min. The product of the reaction was separated from low-molecular components by ultrafiltration with MWCO 3000, was washed 5 times with 1 ml of 50 mmol/l Tris-HCl buffer, pH 7, and was dissolved in 200 µl of 50 mmol/l Tris-HCl, pH 7.

The dUTP-AA-SS-PEG-Cy3 obtained in this manner can be incorporated into the growing strand of nucleic acids by polymerases, e.g. Klenow fragment exo minus or Taq-polymerase.

The dUTP-AA-SS-PEG-Cy3 contains a group that is cleavable under mild conditions, so that the linker with the dye can be cleaved off from the nucleotide. This is, for instance, of particular interest for processes for sequencing by synthesis (Balasubramanian WO 03048387, Tcherkassov WO 02088382, Quake WO0132930, Kartalov WO02072892).

This example shows a general possibility for making further modifications to nucleotides. Further base-modified nucleotide analogs, e.g., 5-propargylamino-dCTP, 5-propargylamino-dUTP, 7-deaza-aminopropargyl-dGTP and 7-deaza-aminopropargyl-dATP can also be modified as described above. Ribonucleotides, 2'-deoxyribonucleotides as well as 2',3'-Dideoxyribonucletide can be used, FIGS. 11 to 14.

Figure 43:
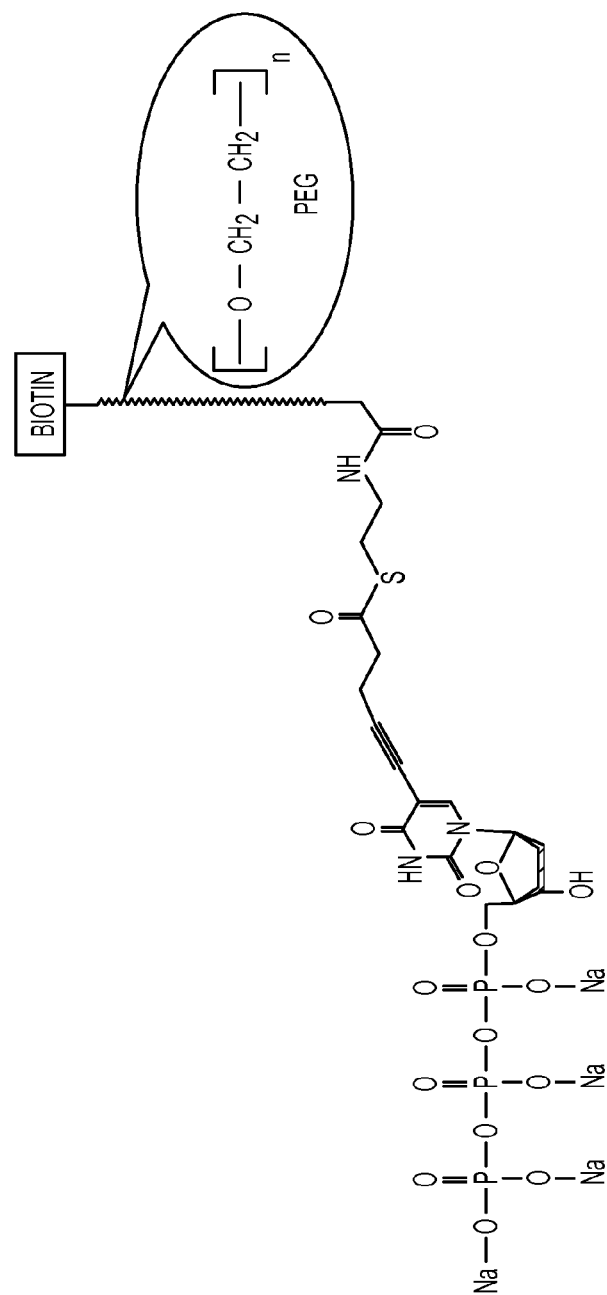
FIG. 43 shows dUTP-AA-SS-PEG-Cy3, as described in Example 37.

Example 37 dUTP-R—CO—S-PEG-Biotin FIG. 43

Figure 44:
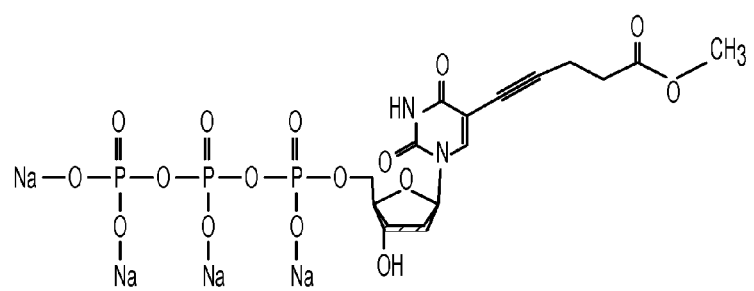
FIG. 44 shows dUTP-R—COOCH$_3$, as described in Example 37.

The dUTP-R—COOCH$_3$ (FIG. 44) was synthesized in similar way as specified (Heike A. Held, Abhijit Roychowdhury, and Steven A. Benner, Nucleosides, Nucleotides & Nucleic Acids, v. 22, p. 391-404 (2003)). The Triphosphate synthesis was conducted according to T. Kovacs, L. Ötvös, Tetrahedron Letters, v. 29, p. 4525-4588 (1988)).

5-iodo-2'-deoxyuridine (500 mg, 1.41 mmol) was suspended in 10 ml of anhydrous DMF in a nitrogen atmosphere at RT and was stirred for 10 min. Then, tetrakis(triphenylphosphine)palladium (0) (160 mg, 0.14 mmol) was added. After another 10 min, 400 µl triethylamine, (480 mg, 4.28 mmol) pent-1-in acid methylester and copper (I) iodide (55 mg, 0.29 mmol) were added successively. After 15 h, the reaction mixture was concentrated in the rotation evaporator and the red oil obtained was separated by means of silica gel chromatography (dichloromethane:methanol=20:1). This produces 400 mg (84%) of product. After triphosphorylation, dUTP-R—COOCH$_3$, was obtained.

Other bases, like cytosine, adenosine and guanosine derivatives, can be also modified in a similar way using the Pent-1-in acid methylester (dissertation "Synthese basenmodifizierter Nukleosidtriphosphate und ihre enzymatische Polymerisation zu funktionalierter DNA", Oliver Thum, Bonn in 2002).

Figure 45:
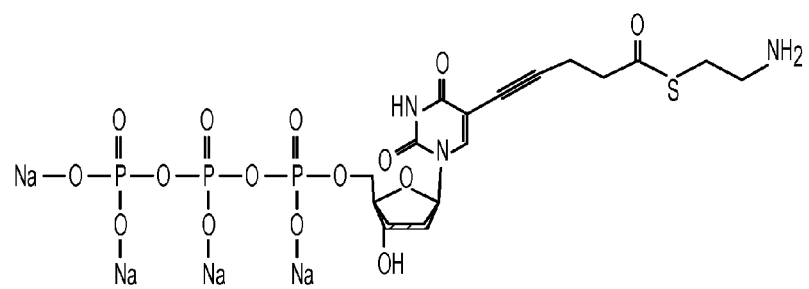
FIG. 45 shows dUTP-R—CO—S—CH2-CH2-NH2, as described in Example 37.

Further modification is performed on the dUTP-R—COOCH3:

A solution of the mercaptoethanolamine (100 µl, 1 mol/l, pH 9) is added to 100 µl of a solution of dUTP-R—COOCH3 (50 mmol/l, in 50 mmol/l borate buffer, pH 9) and is stirred at 40° C. for 3 h. The product of the reaction, the dUTP-R—CO—S—CH2-CH2-NH2 (FIG. 45), is separated from the excess of mercaptoethanolamine on DEAE-cellulose in the borate buffer 10 mmol/l and eluted from the column with 0.3 mol/l of NaCl.

This nucleotide has a thioester group that is cleavable under mild conditions and can be modified on the amino group of the linker.

Figure 46:
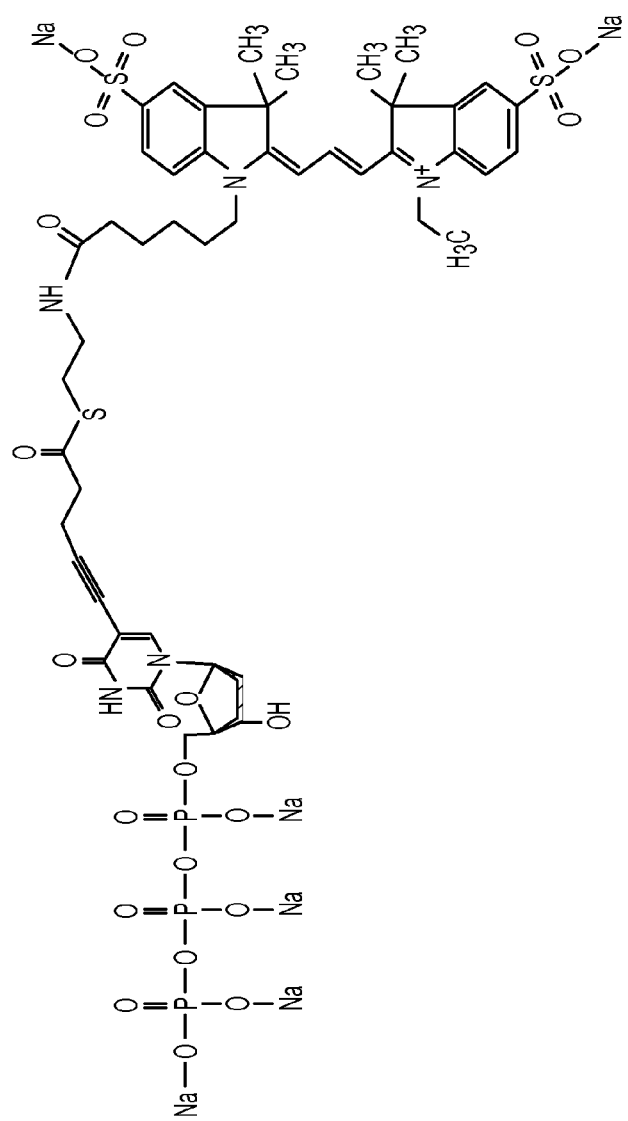
FIG. 46 shows dUTP-R—CO—S—CH$_2$—CH$_2$—NH—R-Cy3, as described in Example 37.

Further modifications can be carried out on this amino group. For instance, a dye can be coupled to it: Synthesis of dUTP-R—CO—S—CH$_2$—CH$_2$—NH—R-Cy3 (FIG. 46)

Cy3-NHS was added to a solution of the dUTP-R—CO—S—CH$_2$—CH$_2$—NH$_2$ (100 µl, 10 mmol/l, in 50 mmol/l borate buffer, pH 9) up to a concentration of 15 mmol/l. The reaction was allowed to proceed at RT for more than 30 min. Next, the Cy3-modified nucleotide was purified on a silica gel plate and RP-18 column similarly as described in Example 15.

Such a nucleotide can be used as a reversible terminator in a method for sequencing nucleic acids (Tcherkassov WO 02088382). The cleavage of the thioester bond can be accomplished, for instance, by adding 100 mmol/l of mercaptoethanol in 50 mmol/l borate buffer, pH 9.

A long linker with a low molecular marker can be also coupled to the amino group of the dUTP-R—CO—S—CH$_2$—CH$_2$—NH$_2$, similarly as in example 19. The obtained dUTP-R—CO—S—CH$_2$—CH$_2$—NH-PEG-biotin can serve as an intermediate product for a nuc-macromolecule.

Figure 47:
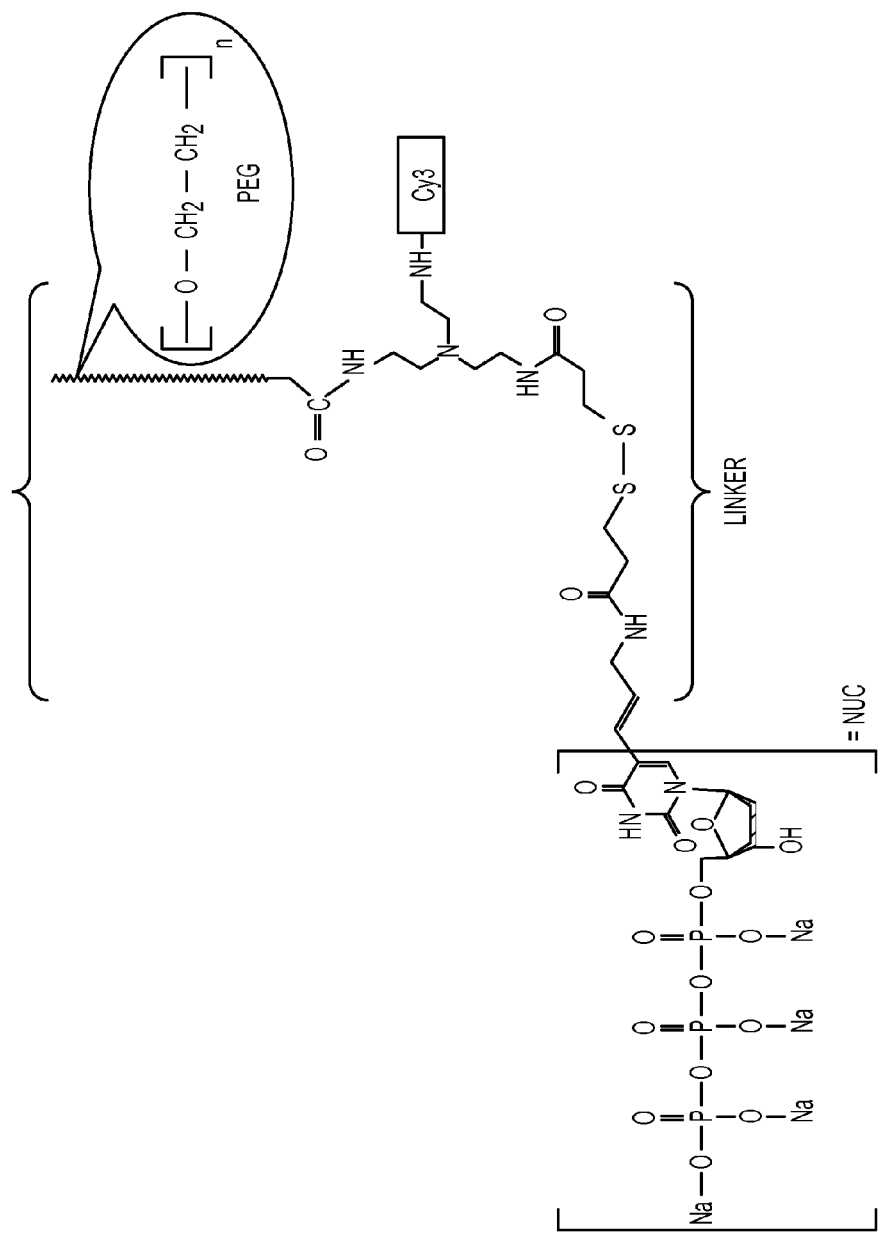
FIG. 47 shows dUTP-AA-SS-Propionate-TEAE-Cy3-PEG, as described in Example 38.

Example 38 dUTP-AA-SS-Propionate-TEAE-Cy3-PEG (FIG. 47)

This derivative can be obtained from dUTP-AA-SS-propionate-TEAE-Cy3 (see example 17) by modifying the amino group in the linker with an mPEG-SPA, e.g., 5000 Da. The modification conditions are similar to those in example 19. This molecule comprises a long linker and can be used in the method according to the invention for rapid purification of the modified nucleotides prior to their use in labeling reactions. A filter with MWCO of 3000 can be used to separate labeled nucleotides from unlabeled nucleotides.

Example 39

Figure 48:
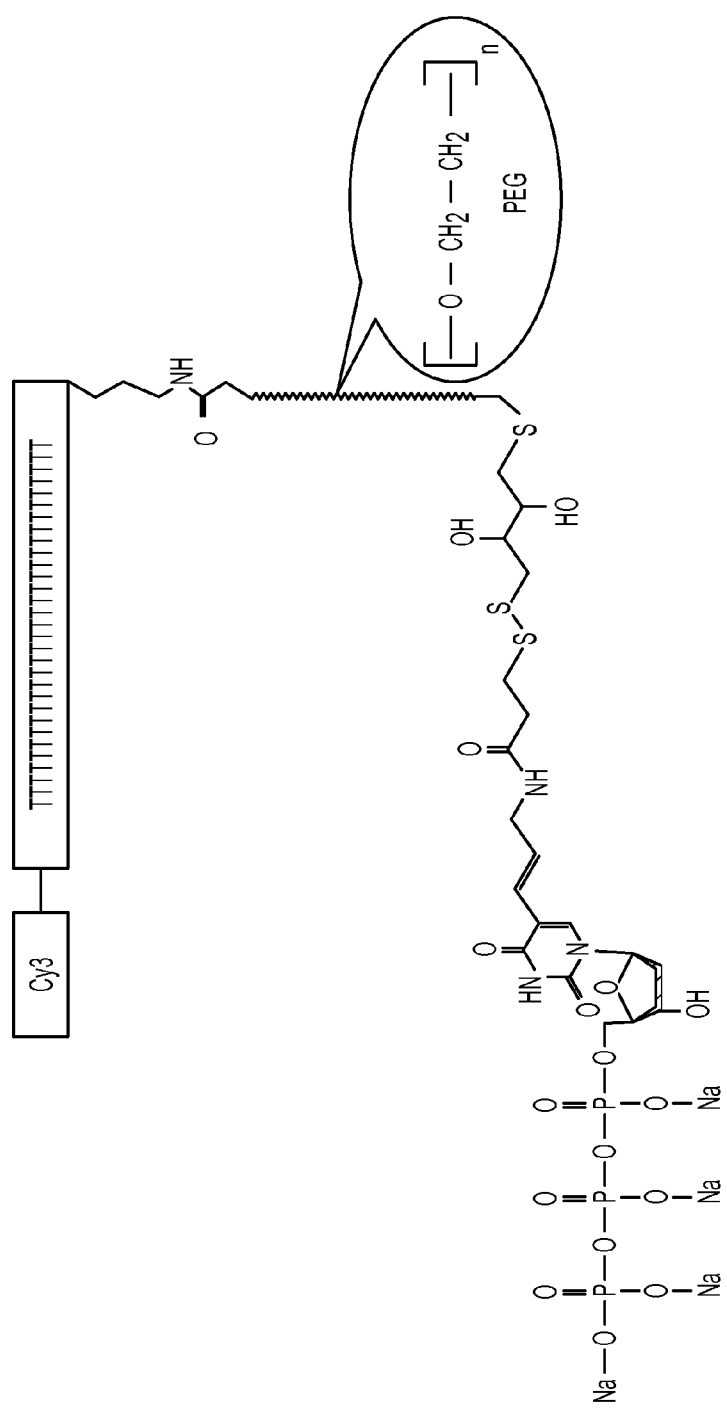
FIG. 48 shows dUTP-AA-SS—R-PEG-Oligo-dT31-Cy3, as described in Example 39.

Synthesis of dUTP-AA-SS—R-PEG-Oligo-dT31-Cy3 (FIG. 48)

Figure 49:
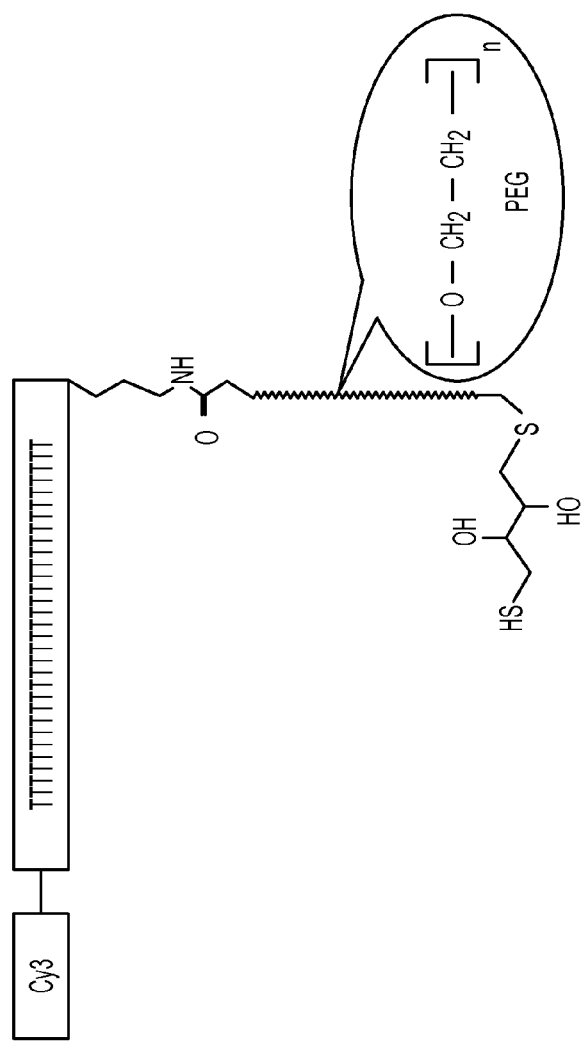
FIG. 49 shows SH—R-PEG-Oligo-dT31-Cy3, as described in Example 39.

Synthesis of SH—R-PEG-Oligo-dT$_{31}$-Cy3 (FIG. 49) (SEQ ID NO:9).

NHS-PEG-maleimide was added to 200 µl of 100 µmol/l solution of 3'-amino-oligo-dT$_{31}$-Cy3 in 50 mmol/l borate buffer, pH 9, until the concentration of 20% (w/v) was reached. The mixture was stirred vigorously at 40° C. for 2 h. The maleimide-PEG-oligo-dT$_{31}$-Cy3 was separated from the excess PEG derivative using DEAE-cellulose column chromatography: The reaction mixture was applied to the column in 10 mmol/l borate, pH 9, and was washed with 20 column volumes of 50 mmol/l borate, pH 9.

The maleimide-PEG-Oligo-dT$_{31}$-Cy3 was eluted from the column 1 M NaCl in 50 mmol/l borate, pH 9. The eluate was first concentrated by ultrafiltration (MWCO 3,000) and the product was rebuffered in 20 mmol/l borate buffer, pH 9.0. The maleimide-PEG-oligo-dT$_{31}$-Cy3 was separated from oligo-dT$_{31}$-Cy3 on preparative polyacrylic gel (15%) by the electrophoresis and was isolated from the gel and dissolved in 50 mmol/l borate buffer, pH 9.0. Yield: 55%.

DTT was to the solution of maleimide-PEG-Oligo-dT$_{31}$-Cy3 up to a concentration 0.5 mol/l and the mixture was stirred for 16 h at RT. SH—R-PEG-Oligo-dT$_{31}$-Cy3 is obtained from the reaction of DTT with maleimide. This substance was separated from the excess DTT on the DEAE column: The reaction mixture was applied to the column in 50 mmol/l Na-acetate, pH 6.0, and was washed with 20 column volumes of 50 mmol/l Na-acetate, pH 6.0. A solution of NaCl (1 mol/l in 50 mmol/l Na-acetate, pH 6.0) was used to elute SH—R-PEG-oligo-dT$_{31}$-Cy3 from the column. The eluate was first concentrated by ultrafiltration (MWCO 3,000) and the product, SH—R-PEG-oligo-dT$_{31}$-Cy3, was rebuffered in 50 mmol/l borate buffer, pH 9.0. The concentration of SH—R-PEG-oligo-dT$_{31}$-Cy3 amounted to 100 µmol/l.

Fifty equivalents of dUTP-AA-PDTP (synthesized as described in the example 1) were added to this solution. After 3 h at RT, separation was conducted on DEAE-cellulose: The mixture was applied to the column in 50 mmol/l Na-acetate buffer, pH 6.0, and was washed with 20 column volumes of 50 mmol/l Na-acetate, pH 6.0. The dUTP-AA-PDTP was eluted using 0.3 mol/l NaCl in 50 mmol/l Na-acetate, pH 6.0; the dUTP-AA-SS—R-PEG-oligo-dT31-Cy3 was eluted using 0.8 mol/l NaCl in 50 mmol/l Na-acetate, pH 6.0. The eluate was first concentrated by ultrafiltration (MWCO 3,000) and the product was rebuffered in 50 mmol/l Na-acetate buffer, pH 6.0.

The substance comprises a nucleoside triphosphate functionality and macromolecular marker functionalities (oligo-dT31). The Oligo-dT31 consists of nucleoside monophosphates which, however, do not take part in the enzymatic reaction and have only a signal-transmitting function. Complementary nucleic acid chains having a signal-giving function can be hybridized to such an oligonucleotide (FIG. 37B). General rules to the hybridization of nucleic acids are known to the person skilled in the art, Anderson "Nucleic Acid Hybridization", 1999.

Polymerases (e.g., Klenow-exo minus polymerase and terminal transferase) accept this compound as a substrate.

Other oligonucleotides can be also coupled to the dUTP derivative in a similar manner. In one embodiment of the invention, other homopolymer oligonucleotides, such as poly-dC, poly-dG or poly-dU or poly-dA, are suitable. In another embodiment, it is also possible to use oligonucleotides with specific sequences. By using specific sequences of oligonucleotides, it is possible to hybridize nucleic acid chains specifically to these sequences. Oligonucleotides comprising hairpin structures (stemloops) can be used for the synthesis of nuc-macromolecules.

In this example, the oligonucleotide comprises one amino group and the Cy3-fluorescence dye, the amino group acting as a coupling position for maleimide-PEG-NHS and being coupled at the 3'-end by a linker. Other coupling groups, like SH—, carboxy-, and aldehyde groups can also be used.

The position of the coupling group can be at one of the ends of the oligonucleotide, or can also be located in the middle of the sequence. Such oligonucleotides can be synthesized by MWG Biotech, Germany.

Oligonucleotides can comprise fluorescence dyes or other reporter groups, like biotin or digoxigenin, as modifications. Several modifications per oligonucleotide are also possible. For instance, FRET pairs or a fluorescent-dye/quencher-molecule pair can be introduced into an oligonucleotide.

This example shows a general possibility for making further modifications to nucleotides. Other base-modified nucleotide analogs, e.g., 5-propargylamino-dCTP, 5-aminopropargyl-dUTP, 7-deaza-aminopropargyl-dGTP and 7-deaza-aminopropargyl-dATP can be also modified in a manner similar to that described above. Ribonucleotides, 2'-deoxyribonucleotides as well as 2',3'-dideoxyribonucletide can be used, FIGS. 11 to 14. Other bases-modified nucleotides can also be used in similar way.

Several dUTP-AA-SS—R-PEG-Oligo-dT31-Cy3, e.g., 10-20, can be coupled to one nuc-macromolecule by adding poly-dA or poly-A. A nuc-macromolecule with linearly arranged nuc-linker-components is thereby obtained (FIG. 37C).

Further modifications, e.g., fluorescence labeling, can be also introduced by adding other modified oligonucleotides that can bind to poly-dA or poly-A.

Example 40

Synthesis of (dATP-PA-PEG)$_n$-PAS-(Cy3)$_m$

The synthesis of dATP-PA-PEG-NH$_2$ was described in the example 19. EDA-Cy3 was synthesized as follows: Cy3-NHS (0.1 mg) was added to 1 ml of solution of EDA (400 mmol/l, in water, pH 8.5 adjusted by HCl). The reaction was stirred for 30 min at RT. The product was separated on RP-18 (water methanol gradient) and the volume was condensed to 0.2 ml.

PAS 100 kDa (35% solution in water) was repeatedly co-evaporated with DMF in a rotary evaporator until a water-free DMF solution was obtained. CDI (3 mg) was added to the resulting solution of PAS (200 μl, 0.1 mmol/l, 2 mg in 200 μl DMF). Reaction was allowed to proceed for 30 min at RT. Next, a solution of EDA-Cy3 (0.2 ml, 0.7 mmol/l) and dATP-PA-PEG-NH$_2$ (0.2 ml, 0.5 mmol/l) were simultaneously added to this solution. The reaction was carried out at RT for 1 h. The product (dATP-PA-PEG)$_n$-PAS-(Cy3)$_m$ was then separated from EDA-Cy3 and dATP-PA-PEG-NH$_2$ by ultrafiltration with 100 kDa MWCO. The average number of the Cy3 derivatives amounts to five per PAS molecule and the average number of nuc-units (dATP) per PAS molecule amounts to two. A nuc-macromolecule comprising several marker units and several nuc-units was synthesized in this manner.

(dATP-PA-PEG)$_n$-PAS-(Cy3)$_m$ acts as a substrate for the DNA polymerases and can be used in the labeling reactions.

Example 41

Nuc-Macromolecules as Monomer Constituents of an Oligonucleotide

For examples of the enzymatic incorporation of nuc-macromolecules into the nucleic acid, see examples 34 and 35.

Couplings of a long linker and a marker to the nucleotide monomers comprising a reactive group were described above. A nucleotide monomer that is part of a polymer, e.g., of a nucleic acid chain, and comprises a reactive group can be modified in a similar way. A long, linear, unbranched linker, like PEG, is preferably used. Nucleotide monomers with a reactive group, such as an amino group or mercapto group, can be coupled into a nucleic acid chain by means of conventional oligonucleotide synthesis. Many modifications can be introduced into an oligonucleotide by custom synthesis, by MWG Biotech for instance.

Synthesis of a Modified Oligonucleotide:

MWG Biotech synthesized an oligonucleotide with 31 dT monomers and an amino group coupled at 5' ends (5'-amino-dT31). It is possible to couple a Fmoc-PEG-NHS linker, for example, to such an oligonucleotide:

Fmoc-PEG-NHS (1 mg of Fmoc-protected NH$_2$—PEG-NHS) was added to 100 μl of a solution of 5'-amino-dT31 (0.5 mmol/l, pH 8.0, in water) and stirred at 30° C. for 8 h. The pH-value was then raised to 11 and the reaction mixture was stirred for another 2 hours at RT. Next, the modified oligonucleotide was separated from unmodified oligonucleotide by electrophoresis in a 15% of polyacrylic gel and isolated. The product of the reaction, NH$_2$—PEG-dT31, was dissolved in 50 μl of 50 mmol hydrogen carbonate buffer, pH 8.0, to a concentration of 0.3 mmol/l. It is possible to couple a macromolecular marker to the terminal amino group. It is possible to synthesize an oligonucleotide modified with a macromolecular marker using a reaction similar to that described in Example 40. EDA-Cy3 was synthesized as in Example 40.

PAS 100 kDa (35% solution in water) was repeatedly co-evaporated with DMF in a rotary evaporator until a water-free solution was obtained. Next, CDI (1 mg, as concentrated solution in DMF) was added to the resulting solution of PAS (50 μl, 0.1 mmol/l, in DMF). Reaction was allowed to proceed for 30 min at RT. Next, a solution of EDA-Cy3 (50 μl, 1.5 mmol/l) and NH$_2$—PEG-dT31 (50 μl, 0.3 mmol/l) were simultaneously added to this solution. The reaction was carried out at RT for 1 h. The product (dT31-PEG)n—PAS-(Cy3)m was then separated from EDA-Cy3 and NH$_2$—PEG-dT31 by ultrafiltration with 100 kDa MWCO. The average number of the Cy3 derivatives per PAS molecule amounts to seven, and the average number of the coupled oligonucleotides per PAS molecule amounts to 1. An oligonucleotide modified by a polymer and comprising a nuc-macromolecule was synthesized in this manner.

Example 42

Synthesis of a Nuc-Macromolecule with a Linker at the Phosphate Group

A linker can be also coupled to phosphate groups of a nucleotide. A coupling of a reactive group, of an amino group to the terminal phosphate group for instance is already known (Jameson et al. Method in Enzymology, 1997, V. 278, p. 363-, A. Draganescu et al. J. Biol. Chem. 2000 V. 275, 4555-). It is possible to couple the linker component to the nucleotide in a manner analogous to the syntheses in other examples.

Synthesis of a nucleotide analog with a modified 3'-phosphate group will be described here. A linker can be coupled to such a modified phosphate group.

First, 3'-O-[(2-cyanoethoxy)-(4-N-Fmoc-aminobutoxy)phosphoryl]-2'-deoxythymidin is synthesized. A 5'-triphosphate is obtained from this via phosphorylation. After the Fmoc protective group is removed, a linker can be coupled to the terminal amino-function Synthesis of 3'-O-[(2-cyanoethoxy)-(4-N-Fmoc-aminobutoxy)phosphoryl]-2'-deoxythymidin

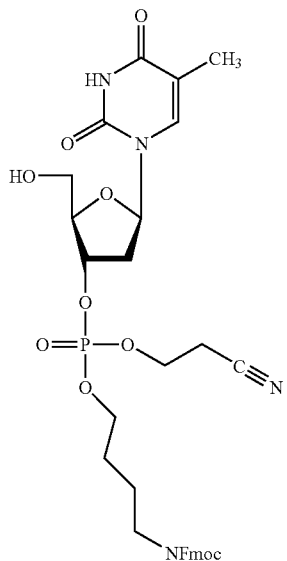

5'-O-DMT-deoxythymidin-3'-O-(2-cyanoethyl)-(N,N-diisopropyl)-phosphoramidite (530 mg) and 4-(Fmoc-amino)-1-butanol (633 mg) were dissolved at RT in 8 ml of anhydrous acetonitril under protective gas (nitrogen). Within 5 min, a tetrazol solution (4.0 ml, 0.45 mol/l, in acetonitrile) was added. After 12 h, cumol-hydroperoxide (135 mg) was added for the oxidation of the phosphoramidites. After 30 min, the excess cumol-hydroperoxide was neutralized with 150 µl of isopropanol. After that, solvents were removed on a rotation evaporator.

To cleave off the DTM protective group, the solid residue was dissolved in 20 ml of a mixture of acetic acid/water (8/2) and was stirred at ambient temperature. After approx. 2 h, a reaction control analysis (TLC silica gel 60; dichlormethane/methanol mixture 95/5) showed that no educt was preset anymore, and 20 ml of toluene was added to the mixture and the mixture was condensed via rotation evaporator. To remove the acetic acid and water completely, five repeated coevaporations using 20 ml of toluene were carried out. The obtained weak-red oil was separated by chromatography on silica gel (PSC plates Merck, 2 mm; dichlormethane/methanol, 9/1).

The triphosphate synthesis was conducted according to T. Kovacs, L. Ötvös, Tetrahedron Letters, Vol 29, 4525-4588 (1988).

3'-O-[(2-cyanoethoxy)-(4-N-Fmoc-aminobutoxy)phosphoryl]-2'-deoxythymidin (150 mg) and a "Protonenschwam" (proton-absorber), 74 mg, were dissolved in trimethylphosphate (0.8 ml). After that, $POCl_3$ was added (100 mg) and mixture was stirred for 1 h at RT. After that, the reaction mixture was cooled down to 4° C. and a solution of pyrophosphate (2.5 ml, 0.5 mol/l, in DMF:tributylamine, 8:1) was added. After 20 min, TEAB buffer (10 ml, 0.2 mol/l, pH 8) was added for the hydrolysis. The nucleoside triphosphate was precipitated with ethanol and purified on DEAE cellulose and RP-18.

For the coupling of a linker, the Fmoc-protective group was removed by incubation with 0.1 mol/l NaOH (30 min at ambient temperature).

Example 43

Synthesis of a Nuc-Macromolecule with a Linker of 4 Chain Atoms and a Water-Soluble Linear Polymer EDC (5 mg) was added to a solution of PAS (100 kD) (50 µl, 5% in water, pH 6.0) and, directly afterwards, AA-dUTP (20 µl, 100 mmol/l, pH 8) was added. After 30 min at RT, the product was separated from low-molecular-weight substances by ultrafiltration using a 50 kDa MWCO filter. On average, approximately 4 nucleotides were coupled per polymer molecule. These nucleotides can be incorporated into the nucleic acid chains in a primer dependent reaction by Klenow fragment.

In this example, the short linker can be also considered as a coupling unit (L) of a long linker, PAS being a part of the linker.

Example 44

Synthesis of a Nuc-Macromolecule with a Linker of 25 Chain Atoms and a Water-Soluble Linear Polymer First, dCTP-PA was reacted with Fmoc-NH-$(PEG)_2$-COOH to yield dCTP-PA-$(PEG)_2$-$NH_2$.

Fmoc-NH-$(PEG)_2$-COON was activated with CDI.

Activated Fmoc-NH-$(PEG)_2$-COOH (200 µl, 40 mmol/l, in DMF) was added to a solution of dCTP-PA (200 µl, 20 mmol/l, in 100 mmol/l borate, pH 8.0). After 30 min, NaOH was added until the pH was raised to 12, and the mixture was incubated for another 30 min at RT. After that, the product was purified on silica gel and RP-18. Yield 15%.

EDC (5 mg) was added to a solution of PAS (100 kD) (50 µl, 5%, pH 6.0) and directly afterwards a solution of dCTP-PA-$(PEG)_2$-$NH_2$ (30 µl, 10 mmol/l, pH 7) was added. After 30 min at RT, the product was separated from low-molecular-weight substances by ultrafiltration using a 50 kDa MWCO filter.

These nucleotides are incorporated into the nucleic acid chains in a primer-dependent reaction by Klenow fragment.

Marker units, for instance, dyes, can be coupled to the polymer.

Example 45

Synthesis of a Nuc-Macromolecule with a Linker of 34 Chain Atoms and a Water-Soluble Linear Polymer Synthesis of dCTP-PA-$(PEG)_2$-$NH_2$ see example 44.

The amino group on PEG was modified with PDTP-NHS as in example 1, so that dCTP-PA-$(PEG)_2$-NH-PDTP resulted.

Aminodextran 70,000 was modified by the reaction with PDTP-NHS, so that on average one dextran molecule was modified with 1.4 PDTP groups. Free SH groups were generated by the following reduction with TCEP, so that aminodextran-SH resulted. The purification was accomplished using a 10 kD MWCO filter.

dCTP-PA-$(PEG)_2$-NH-PDTP (10 µl, 10 mmol/l) was added to a solution of amino-dextran-SH (70 kD) (200 µl, 2.5%, in 50 mmol/l borate buffer, pH 9.0). After 120 min at RT, the product was separated from the low-molecular-weight substances by ultrafiltration using a 10 kDa MWCO filter. The result is aminodextran-SS—R-dCTP, where (R) amounts to 34 chain atoms.

These nucleotides are incorporated into the nucleic acid chains in a primer-dependent reaction by Klenow fragment.

Marker units, for instance, dyes, can be coupled to the aminodextran.

Example 46

Producing a Modified Klenow Fragment Exo Minus of the DNA Polymerase I of *E. coli* (Hereinafter Called Klenow Fragment Exo Minus)

In one embodiment of the modification, a buffer solution (100 µl, 200 mmol/l Tris HCl buffer, pH 10.0, 60% of glycerol) is added to a buffer solution with Klenow fragment exo minus of the DNA polymerase (70 µl, 750 units-vial of Amersham Bioscience, dissolved in the manufacturer's buffer: 50 mmol/l potassium phosphate buffer, pH 7, 1.0 mmol/l DTT, 50% glycerol), the pH value of the solution with the polymerase thus amounting to 9.0. Next, a solution of iodoacetamide (30 µl, 1 mol/l in water) are added. The reaction is carried out for 30 min at RT. A selective modification of the polymerase thereby occurs at the SH group of the cysteine.

In another embodiment of the modification, a solution of TCEP—NaOH (10 µl, 50 mmol/l, pH 8) is first added to a buffer solution with Klenow fragment exo minus of the DNA polymerase (70 µl, 750 units-vial of Amersham Bioscience, dissolved in the manufacturer's buffer, see above). After 10 min at RT, a buffer solution (100 µl, 200 mmol/l Tris HCl buffer, pH 10.0, 60% of glycerin) is added to the solution with polymerase. Next, a solution of iodoacetamide (30 µl, 1 mol/l in water) is added. The reaction is carried out for 30 min at RT. A selective modification of the polymerase thereby occurs on the SH group.

It is possible to purify the modified polymerase, for instance, via ultrafiltration or by an ionic exchanger or dialysis.

It is possible to store the modified polymerase, for instance, in a glycerin-containing buffer. Tris-HCl, borate, and phosphate buffers are suitable as buffers, for example. The pH value of these buffers ranges, for instance, between 5 and 10. The concentration of the glycerin can range, for instance, between 10 and 70%.

It is also possible to add other reagents, for instance PEG or salts like NaCl, $NH_4Cl$, to the polymerase solution. It is preferred that no reductive agents, e.g., DTT, be added to the polymerase solution.

In one embodiment, the storage buffer additionally contains a reagent which can react with SH groups selectively, for instance, iodoacetamide in a concentration between 1 mmol/l and 500 mmol/l.

A polymerase modified in this manner can be used in reactions with nuc-macromolecules instead of Klenow fragment exo minus of the DNA polymerase.

The invention claimed is:

1. A nucleotide conjugate (nuc-macromolecule) having the structure

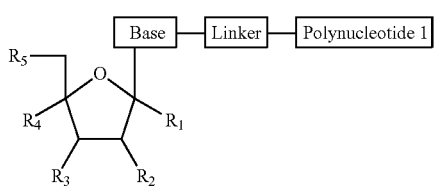

wherein:

Base is selected independently from the group consisting of purine nucleobases, pyrimidine nucleobases and analogs of purine or pyrimidine nucleobases capable of forming Watson-Crick-base pairing, $R_1$—is H, $R_2$—is selected independently from the group consisting of H, OH, halogen, $NH_2$ and SH, $R_3$—is selected independently from the group consisting of H, OH, halogen,—O—$PO_3H$, SH, $N_3$, $NH_2$, O—$CH_3$, O—$CH_2$—O—$CH_3$ and O—$CH_2$—CH=$CH_2$, $R_4$—is H or OH, $R_5$—is selected independently from the group consisting of a monophosphate group, a triphosphate group, a tetraphosphate group, and an alpha thiotriphosphate group; and a pharmaceutically acceptable salt thereof, and Linker is a linker component, which connects said Base and Polynucleotide 1, wherein the length of the Linker is in the range of from 5 to 100 chain atoms, and said Linker is attached covalently to the Base at one of the positions $N^4$ or C-5 when the Base is a pyrimidine nucleobase, or at one of the positions $N^6$ or C-8 when the Base is a purine nucleobase, or at position C-7 when the Base is a 7-deaza-purine nucleobase, and is attached covalently to said Polynucleotide 1, and wherein said Polynucleotide 1 is selected from the group consisting of at least one nucleic acid chain having a length of at least 10 nucleotide monomers, and at least one nucleic acid chain having a length of at least 10 nucleotide monomers wherein said nucleic acid chain is labeled with at least one Detectable Marker Unit.

2. The nucleotide conjugate (nuc-macromolecule) according to claim 1 wherein the purine nucleobase or its analog is selected from the group consisting of adenin-9-yl; 7-deazaadenin-9-yl; guanin-9-yl; 7-deaza-guanin-9-yl;

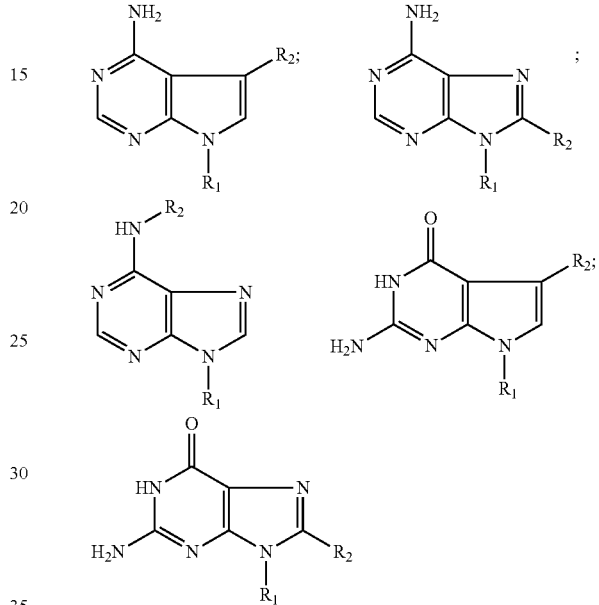

wherein:

$R_1$—is a sugar moiety of the nucleotide conjugate, and
$R_2$—is the linker moiety of the nucleotide conjugate.

3. The nucleotide conjugate (nuc-macromolecule) according to claim 1 wherein the pyrimidine nucleobase or its analog is uracil-1-yl; or cytosin-1-yl;

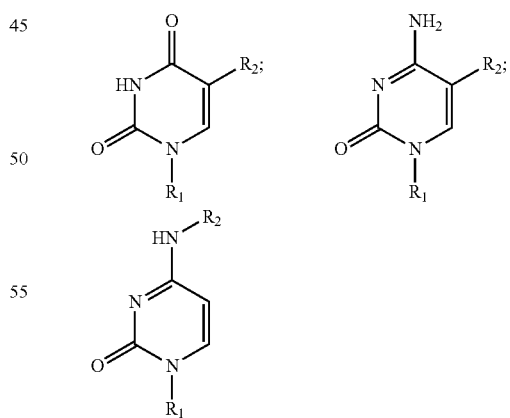

wherein:

$R_1$—is a sugar moiety of the nucleotide conjugate, and
$R_2$—is the linker moiety of the nucleotide conjugate.

4. The nucleotide conjugate (nuc-macromolecule) according to claim 1, wherein the Linker has at least one cleavable bond.

5. The nucleotide conjugate (nuc-macromolecule) according to claim 4, wherein the cleavable bond is a disulfide bond.

6. The nucleotide conjugate (nuc-macromolecule) according to claim 1, wherein the length of the Linker ranges from 5 to 50 chain atoms.

7. The nucleotide conjugate (nuc-macromolecule) according to claim 1, wherein the length of the Linker ranges from 20 to 50 chain atoms.

8. The nucleotide conjugate (nuc-macromolecule) according to claim 1, wherein the length of the Linker ranges from 20 to 100 chain atoms.

9. The nucleotide conjugate (nuc-macromolecule) according to claim 1, wherein the length of the linker ranges from 30 to 100 chain atoms.

10. The nucleotide conjugate (nuc-macromolecule) according to claim 1, wherein the linker is in the range of from 5 to 100 chain atoms and has the structure:
L-Polymer-T,
wherein (L) is a linkage moiety attached covalently at one end to the nucleobase at position $N^4$ or C-5 when the Base is a pyrimidine nucleobase, at position $N^6$ or C-8 when the Base is a purine nucleobase, or at position C-7 when the Base is a 7-deaza-purine nucleobase, and is attached covalently on the other end to the Polymer, and linkage moiety (T) has two ends, one of which is attached covalently to the Polymer and the other end of which is attached covalently to the Polynucleotide, and wherein the Polymer is a water soluble polymer.

11. The nucleotide conjugate (nuc-macromolecule) according to claim 10, having a linker which is bound to the nucleobase of the nuc-component via linkage moiety (L) selected from the group: 3-amino-allyl and 3-amino-propargyl, wherein remaining linker is bound to amino-group of the said linkage moiety (L).

12. The nucleotide conjugate (nuc-macromolecule) according to claim 10 wherein the structure of the Base and linkage moiety (L) is selected from the group consisting of:
$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—$R_7$,
$R_6$—(CH$_2$)$_n$—$R_7$, $R_6$-A-(CH$_2$)$_n$—$R_7$, $R_6$—(CH$_2$)$_n$—B—$R_7$,
$R_6$—(CH=CH—)$_n$—$R_7$, $R_6$-(A-CH=CH—)$_n$—$R_7$, $R_6$—(CH=CH—B—)$_n$—$R_7$,
$R_6$-A-CH=CH—(CH$_2$—)$_n$—$R_7$, $R_6$—(—CH=CH—CH$_2$)$_n$—B—$R_7$,
$R_6$—(C≡C—)$_n$—$R_7$, $R_6$-(A-C≡C—)$_n$—$R_7$, $R_6$—(C≡C—B—)$_n$—$R_7$,
$R_6$-A-C≡C—(CH$_2$—)$_n$—$R_7$, $R_6$—(—C≡C—CH$_2$)$_n$—B—$R_7$, and $R_6$—(—C≡C—CH$_2$—CH$_2$—)$_n$—B—$R_7$; and
$R_6$ is the $N^4$ or C-5 position when the Base is a pyrimidine nucleobase, or the $N^6$ or C-8 position when the Base is a purine nucleobase, or the C-7 position when the Base is a 7-deaza-purine nucleobase, and
$R_7$ is the remaining Linker connected to the polynucleotide 1 moiety, and A and B are selected from the group consisting of —NH—, —O—, —S—, —SS—, —CO—NH—, —NH—CO—, —CO—O—, —O—CO—, —CO—S—, —S—CO—, —P(O)$_2$—, —Si(CH$_3$)$_2$—and —(CH$_2$)$_n$—, wherein n ranges from 1 to 5.

13. The nucleotide conjugate (nuc-macromolecule) according to claim 10, wherein said Polymer is selected independently from the group consisting of:

polyethylene glycol (PEG), polysaccharides, dextran, polyamides, polypeptides, polyphosphates, polyalkylene glycols, copolymers from ethylene glycol and propylene glycol, polyolefinic alcohols, polyvinyl pyrrolidones, poly(hydroxyalkylmethacrylamides), polyhydroxyalkylmethacrylates, polyacrylic acid, polyacrylamide, and polyvinyl alcohol.

14. The nucleotide conjugate (nuc-macromolecule) according to claim 10, wherein said Polymer consists of identical monomers.

15. The nucleotide conjugate (nuc-macromolecule) according to claim 10, wherein said polymer consists of two different kinds of monomers.

16. The nucleotide conjugate (nuc-macromolecule) according to claim 10, linkage moiety (T) is bound to the Polynucleotide 1 and wherein linkage moiety (T) is selected from the group consisting of —O—, —NH—, —CONH—, —NHCO—, and —S—.

17. The nucleotide conjugate (nuc-macromolecule) according to claim 1 wherein the Polynucleotide 1 is an oligonucleotide with a length of from about 10 to about 100 nucleotides.

18. The nucleotide conjugate (nuc-macromolecule) according to claim 1 wherein the Polynucleotide 1 has a length of about 20 to 100000 nucleotides.

19. The nucleotide conjugate (nuc-macromolecule) according to claim 1 wherein the Polynucleotide 1 is single stranded.

20. The nucleotide conjugate (nuc-macromolecule) according to claim 1 wherein the Polynucleotide 1 is double stranded.

21. The nucleotide conjugate (nuc-macromolecule) according to claim 1 wherein the Polynucleotide 1 is selected from the group consisting of DNA, RNA, modified DNA, modified RNA and PNA.

22. The nucleotide conjugate (nuc-macromolecule) according to claim 1, wherein the Base is coupled via said Linker to the 3'-position of said Polynucleotide 1.

23. The nucleotide conjugate (nuc-macromolecule) according to claim 1, wherein the Base is coupled via said linker to the 5'-position of said Polynucleotide 1.

24. The nucleotide conjugate (nuc-macromolecule) according to claim 1, wherein the Base is coupled via said Linker to an internal position of said Polynucleotide 1.

25. A nucleotide conjugate (nuc-macromolecule) according to claim 1, wherein Polynucleotide 1 is labeled with at least one Detectable Marker Unit.

26. The nucleotide conjugate (nuc-macromolecule) according to claim 25, wherein the said Detactable Marker Unit is selected from the group consisting of a dye, fluorescent dye, protein, polynucleotide, dendrimer, quantum dot, nanoparticle, microparticle and water soluble polymer.

27. The nucleotide conjugate (nuc-macromolecule) according to claim 25 consisting of multiple Detectable Marker Units of number (N), wherein (N) is a positive integer of from 2 to 100.

28. A composition comprising a compound having the structure of claim 1 and at least one further chemical ingredient selected from the group consisting of buffer, at least one DNA polymerase, at least one primer, and at least one 2'-deoxynucleoside 5'-triphosphate.

29. A polynucleotide (polynucleotide 4) consisting of at least one nucleotide conjugate having the structure according to claim 1, wherein said nucleotide conjugate is connected via its 5'-monophosphate diester group to the 3'-OH— terminal group of said polynucleotide 4

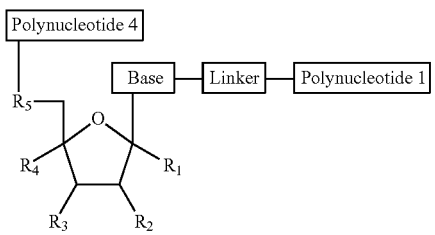

and wherein:
Base is selected independently from the group consisting of purine nucleobases, pyrimidine nucleobases and analogs of purine or pyrimidine nucleobases capable of forming Watson-Crick-base pairing,
$R_1$—is H,
$R_2$—is selected independently from the group consisting of H, OH, halogen, $NH_2$ and SH,
$R_3$—is selected independently from the group consisting of H, OH, halogen, —O—$PO_3H$, SH, $N_3$, $NH_2$, O—$CH_3$, O—$CH_2$—O—$CH_3$ and O—$CH_2$—CH=$CH_2$,
$R_4$—is H,
$R_5$—is a monophosphate diester group or a pharmaceutically acceptable salt thereof, and
Linker is a linker component, which connects said Base and Polynucleotide 1, and
wherein the length of the Linker is in the range of from 5 to 100 chain atoms, and said Linker is attached covalently to the Base at one of the positions $N^4$ or C-5 when the Base is a pyrimidine nucleobase, or at one of the positions $N^6$ or C-8 when the Base is a purine nucleobase, or at position C-7 when the Base is a 7-deaza-purine nucleobase, and is attached covalently to said Polynucleotide 1, and
wherein said Polynucleotide 1 consists of at least one nucleic acid chain having a length of at least 10 nucleotides, and Polynucleotide 4 is a nucleic acid.

30. A polynucleotide (polynucleotide 4) consisting of at least one nucleotide conjugate having the structure according to claim 1, wherein said nucleotide conjugate is connected via its 5'-monophosphate diester group to the 3'-OH— terminal group of said Polynucleotide 4, and a further Polynucleotide 5 connected via its 5'-monophosphate diester group to the 3'-position of the said nucleotide conjugate

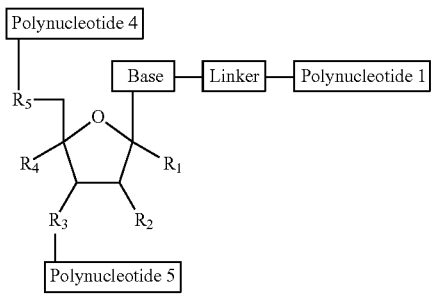

and wherein:
Base is selected independently from the group consisting of purine nucleobases, pyrimidine nucleobases and analogs of purine or pyrimidine nucleobases capable of forming Watson-Crick-base pairing,
$R_1$—is H,
$R_2$—is selected independently from the group consisting of H, —OH, halogen, —$NH_2$ and —SH,
$R_3$—is selected independently from the group consisting of —O— and —O—($PO_2$)—O—; wherein Polynucleotide 5 is a nucleic acid,
$R_4$—is H,
$R_5$—is a monophosphate diester group or a pharmaceutically acceptable salt thereof, and
Linker is a linker component, which connects said Base and Polynucleotide 1, and
wherein the length of the Linker is in the range of from 5 to 100 chain atoms, and said Linker is attached covalently to the Base at one of the positions $N^4$ or C-5 when the Base is a pyrimidine nucleobase, or at one of the positions $N^6$ or C-8 when the Base is a purine nucleobase, or at position C-7 when the Base is a 7-deaza-purine nucleobase, and is attached covalently to said Polynucleotide 1, and
wherein said Polynucleotide 1 consists of at least one nucleic acid chain having a length of at least 10 nucleotides, and Polynucleotide 4 is a nucleic acid.

31. A nucleotide conjugate (nuc-macromolecule) having the structure:

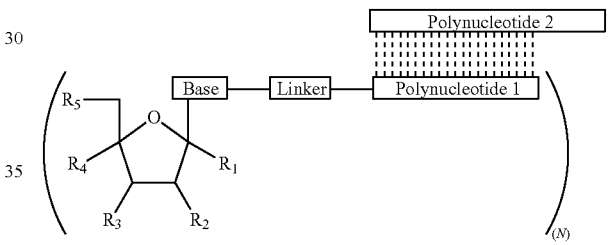

wherein:
Polynucleotide 1 is selected from the group consisting of at least one nucleic acid chain having a length of at least 10 nucleotides, and at least one nucleic acid chain having a length of at least 10 nucleotide monomers wherein said nucleic acid chain is labeled with at least one Detectable Marker Unit, and
Polynucleotide 2 is selected from the group consisting of at least one nucleic acid chain having a length of between 10 and 10000 nucleotide monomers, at least one nucleic acid chain having a length between 10 and 10000 nucleotide monomers and said nucleic acid chain is labeled with at least one Detectable Marker Unit, and
Polynucleotide 1 is attached to Polynucleotide 2 via complementary base pairing, and
Base is selected independently from the group consisting of purine nucleobases, pyrimidine nucleobases and analogs of purine or pyrimidine nucleobases capable of forming Watson-Crick-base pairing,
$R_1$—is H,
$R_2$—is selected independently from the group consisting of H, OH, halogen, $NH_2$ and SH,
$R_3$—is selected independently from the group consisting of H, OH, halogen, —O—$PO_3H$, SH, $N_3$, $NH_2$, O—$CH_3$, O—$CH_2$—O—$CH_3$ and O—$CH_2$—CH=$CH_2$, $R_4$—is H or OH, $R_5$—is selected independently from the group consisting of a triphosphate group, a tetraphosphate group, and an alpha thiotriphosphate group; or a pharmaceutically acceptable salt thereof, and Linker is a linker component, which connects said Base and Polynucleotide 1, and wherein the length of the Linker is in the range of from 5 to 100 chain atoms, and said Linker is attached covalently to the Base at one of the positions $N^4$ or C-5 when the Base is a pyrimidine nucleobase, or at one of the positions $N^6$ or C-8 when the Base is a purine nucleobase, or at position C-7 when the Base is a 7-deaza-purine nucleobase, and is attached covalently to said Polynucleotide 1, and (N) is a positive integer of 1 to 1000.

32. The nucleotide conjugate (nuc-macromolecule) according to claim 31 wherein (N) is a positive integer ranging from 2 to 10.

33. The nucleotide conjugate (nuc-macromolecule) according to claim 31 wherein (N) is a positive integer ranging from 10 to 1000.

34. The nucleotide conjugate (nuc-macromolecule) according to claim 31 wherein (N) is 1.

35. The nucleotide conjugate (nuc-macromolecule) according to claim 31 wherein the Polynucleotide 2 is selected from the group consisting of DNA, RNA, and PNA.

36. The nucleotide conjugate (nuc-macromolecule) according to claim 31 wherein said Polynucleotide 2 is labeled with 1 to 1000 Detectable Marker Units.

37. The nucleotide conjugate (nuc-macromolecule) according to claim 35, wherein the Detectable Marker Unit is selected from the group consisting of dye, fluorescent dye, protein, polynucleotide, dendrimers, quantum dot, nanoparticles and microparticles.

38. A nucleotide conjugate (nuc-macromolecule) having the structure:

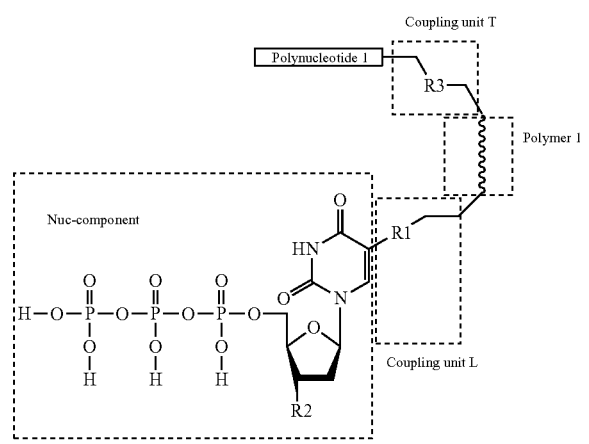

wherein:

Nuc-component consists of a 2'-deoxyuridine-5'-triphosphate substituent attached at its 5-position to the coupling unit; or a pharmaceutically acceptable salt thereof, and Linker consists of Coupling unit L, Polymer 1 and Coupling unit T and connects the nucleobase of the nuc-component and a Polynucleotide 1, and the length of the Linker is in the range of from 10 to 100 chain atoms, and said Linker is attached covalently to the nucleobase at the C-5 position of the uracil-1-yl nucleobase, and is attached covalently to said Polynucleotide 1, and Polynucleotide 1 is a nucleic acid chain with the length ranging from 10 to 100000 nucleotides, and Coupling unit L consists of R1 which is selected from the group consisting of:

$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—$R_7$, $R_6$—(CH$_2$)$_n$—$R_7$, $R_6$-A-(CH$_2$)$_n$—$R_7$, $R_6$—(CH$_2$)$_n$—B—$R_7$, $R_6$—(CH=CH—)$_n$—$R_7$, $R_6$-(A-CH=CH—)$_n$—$R_7$, $R_6$—(CH=CH—B—)$_n$—$R_7$, $R_6$-A-CH=CH—(CH$_2$—)$_n$—$R_7$, $R_6$—(—CH=CH—CH$_2$)$_n$—B—$R_7$, $R_6$—(C≡C—)$_n$—$R_7$, $R_6$-(A-C≡C—)$_n$—$R_7$, $R_6$—(C≡C—B—)$_n$—$R_7$, $R_6$-A-C≡C—(CH$_2$—)$_n$—$R_7$, $R_6$—(—C≡C—CH$_2$)$_n$—B—$R_7$; and $R_6$—(—C≡C—CH$_2$—CH$_2$—)$_n$—B—$R_7$; and $R_6$ represents the attachment point at the C-5 position of a pyrimidine nucleobase, and $R_7$ is the remaining Linker connected to the Polynucleotide 1 moiety, and A and B are selected from the group consisting of —NH—, —O—, —S—, —SS—, —CO—NH—, —NH—CO—, —CO—O—, —O—CO—, —CO—S—, —S—CO—, —P(O)$_2$—, —Si(CH$_3$)$_2$—and —(CH$_2$)$_n$—, wherein n ranges from 1 to 5, and said Polymer 1 is selected independently from the group consisting of:

polyethylene glycol (PEG), polysaccharides, dextran, polyamides, polypeptides, polyphosphates, polyalkylene glycols, copolymers from ethylene glycol and propylene glycol, polyolefinic alcohols, polyvinyl pyrrolidones, poly(hydroxyalkylmethacrylamides), polyhydroxyalkylmethacrylates, polyacrylic acid, polyacrylamide, and polyvinyl alcohol, and coupling unit T connects the Polymer 1 and Polynucleotide 1 and consists of R3, which is a linkage selected from the group consisting of —O—, —NH—, —CONH—, —NHCO—, and —S—, and R2 is selected independently from the group consisting of H, OH, halogen, —O—PO$_3$H, SH, N$_3$, NH$_2$, O—CH$_3$, O—CH$_2$—O—CH$_3$ and O—CH$_2$—CH=CH$_2$.

39. A nucleotide conjugate (nuc-macromolecule) having the structure:

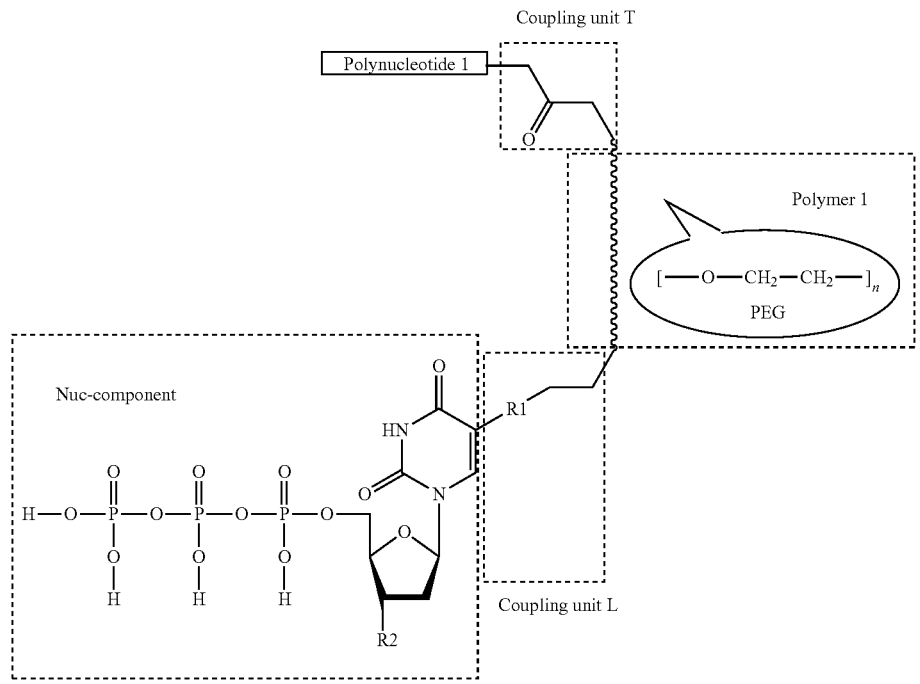

wherein:
Nuc-component consists of a 2'-deoxyuridine-5'-triphosphate substituent attached at its 5-position to the coupling unit; or a pharmaceutically acceptable salt thereof, and Linker consists of Coupling unit L, Polymer 1 and Coupling unit T and connects the nucleobase of the nuc-component and a Polynucleotide 1, and the length of the Linker is in the range of from 10 to 100 chain atoms, and said Linker is attached covalently to the nucleobase at the C-5 position of the uracil-1-yl nucleobase, and is attached covalently to said Polynucleotide 1, and Polynucleotide 1 is a nucleic acid chain with the length ranging from 10 to 100 nucleotides, and Coupling unit L consists of R1 which is selected from the group consisting of:

$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—$R_7$, $R_6$—(CH$_2$)$_n$—$R_7$, $R_6$-A-(CH$_2$)$_n$—$R_7$, $R_6$—(CH$_2$)$_n$—B—$R_7$, $R_6$—(CH=CH—)$_n$—$R_7$, $R_6$-(A-CH=CH—)$_n$—$R_7$, $R_6$—(CH=CH—B—)$_n$—$R_7$, $R_6$-A-CH=CH—(CH$_2$—)$_n$—$R_7$, $R_6$—(—CH=CH—CH$_2$)$_n$—B—$R_7$, $R_6$—(C≡C—)$_n$—$R_7$, $R_6$-(A-C≡C—)$_n$—$R_7$, $R_6$—(C≡C—B—)$_n$—$R_7$, $R_6$-A-C≡C—(CH$_2$—)$_n$—$R_7$, $R_6$—(—C≡C—CH$_2$)$_n$—B—$R_7$, and $R_6$—(—C≡C—C$_2$—CH$_2$—)$_n$—B—$R_7$; and $R_6$ represents the attachment point at the C-5 position of a pyrimidine nucleobase, and $R_7$ is the remaining Linker connected to the Polynucleotide 1 moiety, and A and B are selected from the group consisting of —NH—, —O—, —S—, —SS—, —CO—NH—, —NH—CO—, —CO—O—, —O—CO—, —CO—S—, —S—CO—, —P(O)$_2$,—Si(CH$_3$)$_2$— and —(CH$_2$)$_n$—, wherein n ranges from 1 to 5, and said Polymer 1 is a polyethylene glycol(PEG), and coupling unit T connects the Polymer 1 and Polynucleotide 1 and consists of R3, which is a linkage selected from the group consisting of —O—, —NH—, —CONH—, —NHCO—, and —S—, and R2 is selected independently from the group consisting of H, OH, halogen, —O—PO$_3$H, SH, N$_3$, NH$_2$, O—CH$_3$, O—CH$_2$—O—CH$_3$ and O—CH$_2$—CH=CH$_2$.

40. A nucleotide conjugate (nuc-macromolecule) having the structure:

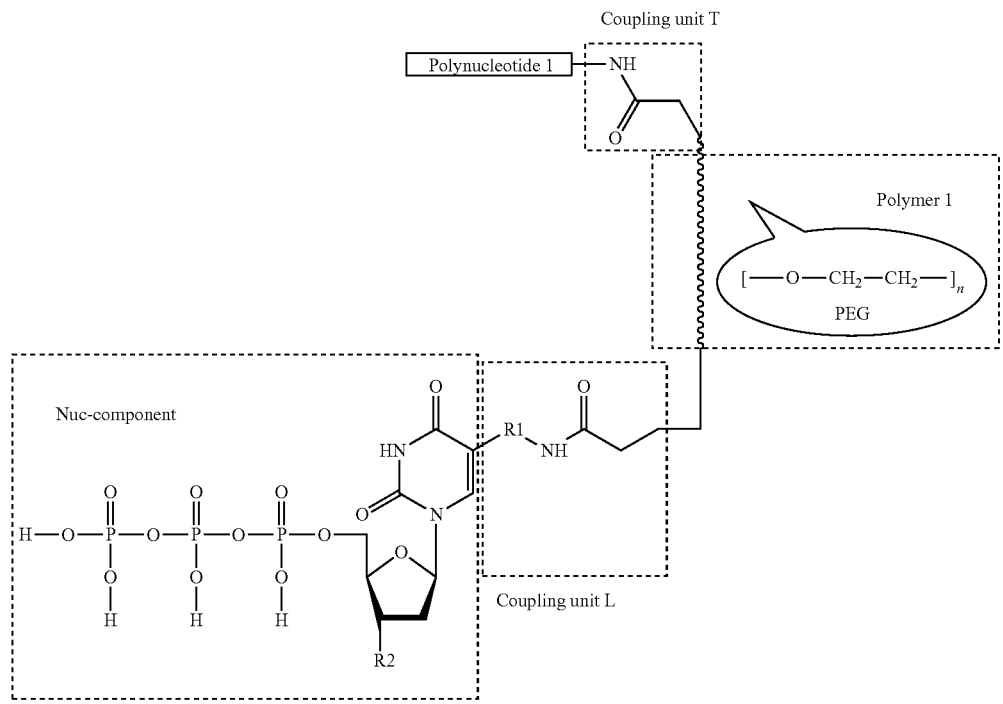

wherein:
Nuc-component consists a 2'-deoxyuridine-5'-triphosphate substituent attached at its 5-position to the coupling unit; or a pharmaceutically acceptable salt thereof, and
Linker connects the nucleobase of the nuc-component and a Polynucleotide 1, and
Linker consisting of Coupling unit L, Polymer 1 and Coupling unit T, and
the length of the Linker is in the range of from 10 to 100 chain atoms, and said Linker is attached covalently to the nucleobase at the C-5 position of the uracil-1-yl nucleobase, and is attached covalently to said Polynucleotide 1, and Polynucleotide 1 is a nucleic acid chain with the length ranging from 10 to 100 nucleotides, and
Coupling unit L is selected from the group consisting of 3-amino-allyl (R1) and 3-amino-propargyl (R1), wherein remaining linker is bound to amino-group of the said linkage moiety (R1), and
said Polymer 1 is a polyethylene glycol(PEG), and
Coupling unit T connects the linker to the polynucleotide 1 having the structure —CONH—, and
R2 is selected independently from the group consisting of H, OH, halogen, —O—PO$_3$H, SH, N$_3$, NH$_2$, O—CH$_3$, O—CH$_2$—O—CH$_3$ and O—CH$_2$—CH=CH$_2$.

41. A nucleotide conjugate (nuc-macromolecule) having the structure:

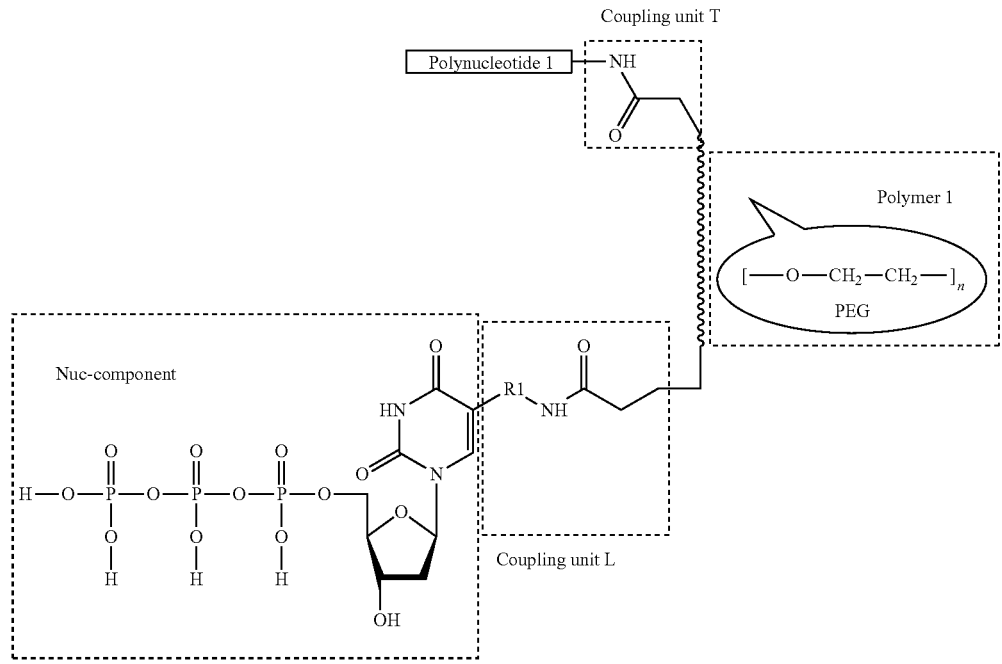

wherein:

Nuc-component consists of a 2'-deoxyuridine-5'-triphosphate substituent attached at its 5-position to the coupling unit; or a pharmaceutically acceptable salt thereof, and Linker connects the nucleobase of the nuc-component and a Polynucleotide 1, and Linker consists of Coupling unit L, Polymer 1 and Coupling unit T, and the length of the Linker is in the range of from 10 to 100 chain atoms, and said Linker is attached covalently to the nucleobase at the C-5 position of the uracil-1-yl nucleobase, and is attached covalently to said Polynucleotide 1, and Polynucleotide 1 is a nucleic acid chain with the length ranging from 10 to 100 nucleotides, and Coupling unit L consists of R1 which is selected from 3 aminoallyl and 3-aminopropargyl, wherein the remaining linker is bound to amino group of the linkage moiety (R1), and said Polymer 1 is a polyethylene glycol(PEG), and Coupling unit T connects the linker to the polynucleotide 1 having the structure —CONH—.

42. A nucleotide conjugate (nuc-macromolecule) having the structure:

wherein:

Nuc-component consists of a 2'-deoxyuridine-5'-triphosphate substituent attached at its 5-position to the coupling unit; or a pharmaceutically acceptable salt thereof, and Linker connects the nucleobase of the Nuc-component and a Polynucleotide 1, and Linker consists of Coupling unit L, Polymer 1 and Coupling unit T, and the length of the Linker is in the range of from 10 to 100 chain atoms, and said Linker is attached covalently to the nucleobase at the C-5 position of the uracil-1-yl nucleobase, and is attached covalently to said Polynucleotide 1, and Polynucleotide 1 is a nucleic acid chain with the length ranging from 10 to 100 nucleotides, and Coupling unit L consists of 3-amino-propargyl, wherein the remaining linker is bound to the amino group of the 3aminopropargyl moiety and said Polymer 1 is a polyethylene glycol(PEG), and Coupling unit T connects the linker to the polynucleotide 1 having the structure —CONH—.

43. A nucleotide conjugate (nuc-macromolecule) having the structure

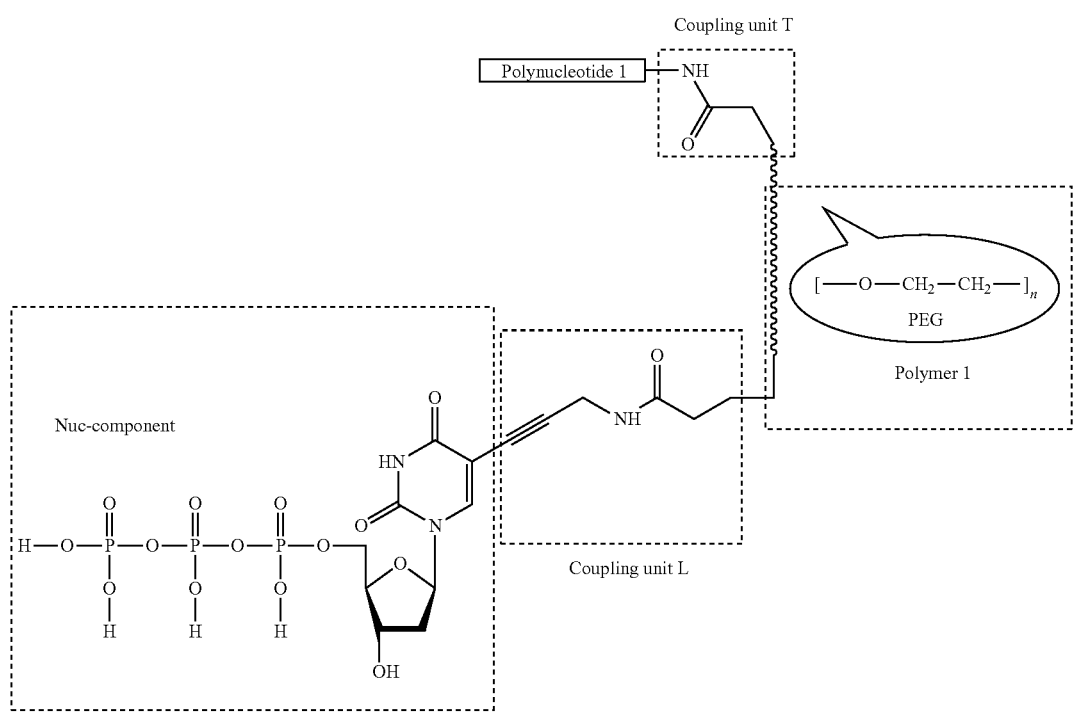

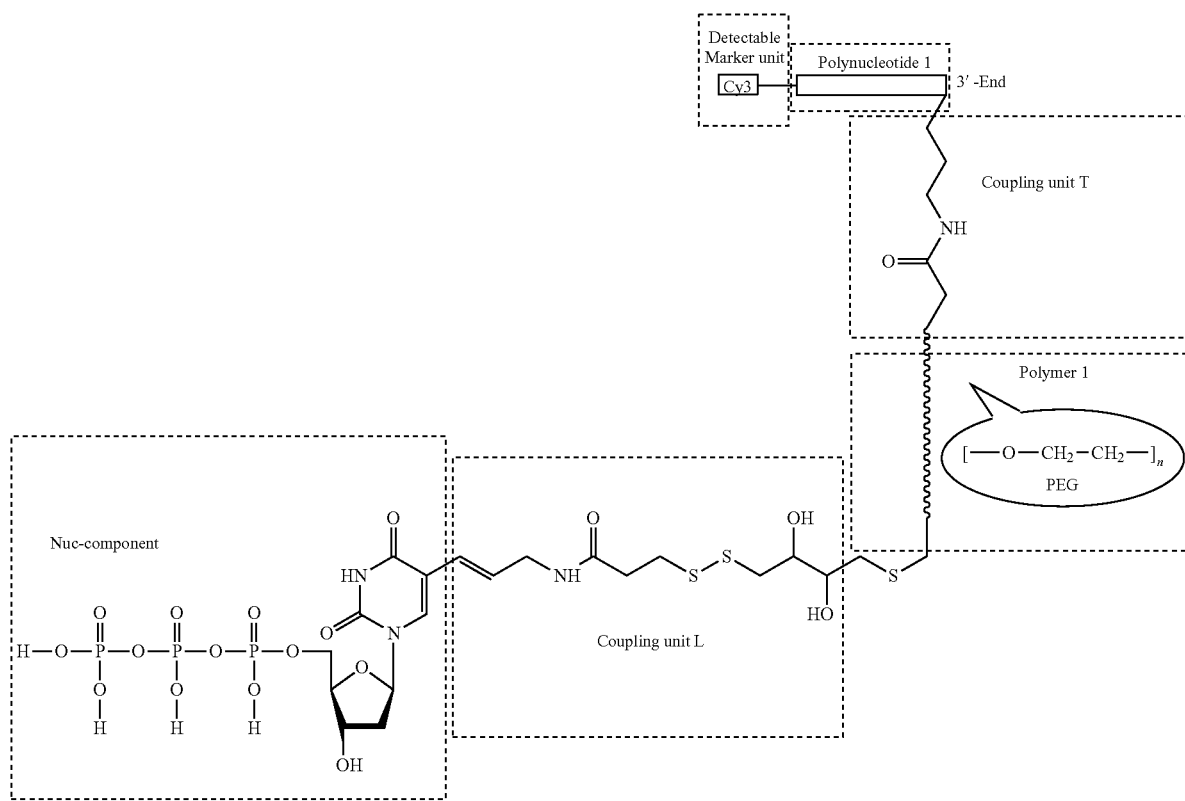

wherein:
Nuc-component consists of a 2'-deoxyuridine-5'-triphosphate substituent attached at its 5-position to the Coupling unit; or a pharmaceutically acceptable salt thereof, and Linker is a cleavable linker component, which connects the nucleobase of the nuc-component and a Polynucleotide 1 of the Marker,
wherein the length of the Linker is in the range of from 20 to 1000 chain atoms, and said Linker is attached covalently to the nucleobase at the C-5 position of the uracil-1-yl nucleobase, and is attached covalently to said Polynucleotide 1 of the Marker at the 3'-end of said Polynucleotide 1, and Polynucleotide 1 of is an oligonucleotide consisting of 10 to 100 nucleotide monophosphate moieties, and Detectable Marker Unit is Cy3-fluorescent dye attached to the 5'-end of said oligonucleotide.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: Primer, example 34A, modified on 5 prime-end by
      Cy3

<400> SEQUENCE: 1
taatacgact cactataggg                                                   20

<210> SEQ ID NO 2
<211> LENGTH: 33
<212> TYPE: DNA
<213> ORGANISM: Artificial
<220> FEATURE:
<223> OTHER INFORMATION: Template, example 34A

<400> SEQUENCE: 2
agttttagtt ttaccctata gtgagtcgta tta                                    33

<210> SEQ ID NO 3
<211> LENGTH: 35
<212> TYPE: DNA
<213> ORGANISM: Artificial
<220> FEATURE:
<223> OTHER INFORMATION: Primer, example 34B, modified at 5 prime -end
      by Cy3

<400> SEQUENCE: 3
tttttttttt tttttttttt tttttttttt ttttt                                  35

<210> SEQ ID NO 4
<211> LENGTH: 40
<212> TYPE: DNA
<213> ORGANISM: Artificial
<220> FEATURE:
<223> OTHER INFORMATION: Oligonucleotide, modified at 5 prime -end by
      Cy3

<400> SEQUENCE: 4
tttttttttt tttttttttt tttttttttt tttttttttt                             40

<210> SEQ ID NO 5
<211> LENGTH: 50
<212> TYPE: DNA
<213> ORGANISM: Artificial
<220> FEATURE:
<223> OTHER INFORMATION: Oligonucleotide, example 34B, modified at 5
      prime -end by Cy3

<400> SEQUENCE: 5

```
tttttttttt tttttttttt tttttttttt tttttttttt tttttttttt      50
```

<210> SEQ ID NO 6
<211> LENGTH: 270
<212> TYPE: DNA
<213> ORGANISM: Artificial
<220> FEATURE:
<223> OTHER INFORMATION: Polynucleotide with an average length of 270
      nucleotides, example 34B

<400> SEQUENCE: 6

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa                                     270
```

<210> SEQ ID NO 7
<211> LENGTH: 50
<212> TYPE: DNA
<213> ORGANISM: Artificial
<220> FEATURE:
<223> OTHER INFORMATION: Oligonucleotide, example 34C, modiified at 3
      prime- end by biotin, attached via a TEG-linker

<400> SEQUENCE: 7

```
aaaaaaaaaa aaaaaaaaaa aaaaaaaaaa aaaaaaaaaa aaaaaaaaaa      50
```

<210> SEQ ID NO 8
<211> LENGTH: 35
<212> TYPE: DNA
<213> ORGANISM: Artificial
<220> FEATURE:
<223> OTHER INFORMATION: Primer, example 35

<400> SEQUENCE: 8

```
tttttttttt tttttttttt tttttttttt ttttt                       35
```

<210> SEQ ID NO 9
<211> LENGTH: 31
<212> TYPE: DNA
<213> ORGANISM: Artificial
<220> FEATURE:
<223> OTHER INFORMATION: Oligonucleotide, example 39, modified at 3
      prime- end by an amino-group, at 5 prime- end by Cy3

<400> SEQUENCE: 9

```
tttttttttt tttttttttt tttttttttt t                           31
```

<210> SEQ ID NO 10
<211> LENGTH: 31
<212> TYPE: DNA
<213> ORGANISM: Artificial
<220> FEATURE:
<223> OTHER INFORMATION: Oligonucleotide, example 30, modified at 3
      prime- end by biotin, coupled via TEG-spacer

<400> SEQUENCE: 10

```
tttttttttt tttttttttt tttttttttt t                           31
```

<210> SEQ ID NO 11
<211> LENGTH: 30
<212> TYPE: DNA

```
<213> ORGANISM: Artificial
<220> FEATURE:
<223> OTHER INFORMATION: Oligonucleotide, examples 27 and 32, modified
      at 3 prime- end by SH-group

<400> SEQUENCE: 11
tttttttttt tttttttttt tttttttttt                                           30
```